US008653262B2

(12) United States Patent
Ebel et al.

(10) Patent No.: US 8,653,262 B2
(45) Date of Patent: Feb. 18, 2014

(54) CCR2 RECEPTOR ANTAGONISTS AND USES THEREOF

(75) Inventors: Heiner Ebel, Biberach an der Riss (DE); Silke Hobbie, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 604 days.

(21) Appl. No.: 12/602,274

(22) PCT Filed: May 29, 2008

(86) PCT No.: PCT/EP2008/056573
§ 371 (c)(1),
(2), (4) Date: Apr. 13, 2010

(87) PCT Pub. No.: WO2008/145681
PCT Pub. Date: Dec. 4, 2008

(65) Prior Publication Data
US 2010/0204209 A1    Aug. 12, 2010

(30) Foreign Application Priority Data

May 31, 2007  (EP) .................................... 07109376

(51) Int. Cl.
*C07D 403/04*    (2006.01)
*C07D 413/14*    (2006.01)
*C07D 401/14*    (2006.01)
*A61P 11/06*     (2006.01)

(52) U.S. Cl.
USPC .......................... 544/121; 544/371; 544/364

(58) Field of Classification Search
USPC ................. 544/362, 121, 238, 295, 371, 364;
514/253.04, 234.5, 252.02
See application file for complete search history.

(56) References Cited

U.S. PATENT DOCUMENTS

| | | | |
|---|---|---|---|
| 4,032,526 A | | 6/1977 | Cross et al. |
| 5,631,269 A | | 5/1997 | Broughton et al. |
| 6,127,386 A | | 10/2000 | Lin et al. |
| 6,143,892 A | * | 11/2000 | Graneto et al. ............... 544/364 |
| 6,423,713 B1 | * | 7/2002 | Anantanarayan et al. . 514/235.8 |
| 6,514,977 B1 | | 2/2003 | Anantanarayan et al. |
| 6,806,279 B2 | * | 10/2004 | McDowell et al. ........... 514/326 |
| 6,979,686 B1 | * | 12/2005 | Naraian et al. ............. 514/235.8 |
| 7,504,511 B2 | | 3/2009 | Carayon et al. |
| 7,507,740 B2 | | 3/2009 | Ishikawa et al. |
| 7,612,201 B2 | * | 11/2009 | Beswick et al. ............. 544/121 |
| 7,777,041 B2 | | 8/2010 | Carayon et al. |
| 7,807,671 B2 | * | 10/2010 | Wang et al. ................. 514/234.5 |
| 7,915,261 B2 | | 3/2011 | Ishii et al. |
| 7,919,494 B2 | | 4/2011 | Ishii et al. |
| 7,919,495 B2 | | 4/2011 | Ishii et al. |
| 8,110,575 B2 | | 2/2012 | Gottschling et al. |
| 2004/0014744 A1 | | 1/2004 | Haviv et al. |
| 2005/0192302 A1 | | 9/2005 | Xue et al. |
| 2005/0222151 A1 | | 10/2005 | Carruthers et al. |
| 2006/0004049 A1 | | 1/2006 | Yao et al. |
| 2006/0173012 A1 | | 8/2006 | Hohlweg |
| 2007/0032475 A1 | | 2/2007 | Ye et al. |
| 2007/0244132 A1 | | 10/2007 | Ishikawa et al. |
| 2008/0161280 A1 | | 7/2008 | Gandhi et al. |
| 2008/0306046 A1 | | 12/2008 | Ishii et al. |
| 2009/0048238 A1 | | 2/2009 | Aebi et al. |
| 2009/0131417 A1 | | 5/2009 | Letavic et al. |
| 2009/0318467 A1 | | 12/2009 | Adam et al. |
| 2010/0009971 A1 | | 1/2010 | Ishii et al. |
| 2010/0009972 A1 | | 1/2010 | Ishii et al. |
| 2010/0204209 A1 | | 8/2010 | Ebel et al. |
| 2010/0204230 A1 | * | 8/2010 | Blurton et al. ............. 514/235.8 |
| 2011/0021500 A1 | | 1/2011 | Gottschling et al. |
| 2011/0183957 A1 | | 7/2011 | Wityak et al. |
| 2011/0301143 A1 | * | 12/2011 | Isabel et al. ............. 514/210.18 |
| 2012/0004252 A1 | | 1/2012 | Ebel et al. |
| 2012/0053164 A1 | | 3/2012 | Ebel et al. |
| 2012/0088754 A1 | * | 4/2012 | Van Emelen et al. ......... 514/218 |
| 2012/0108572 A1 | | 5/2012 | Wagner et al. |
| 2013/0090338 A1 | | 4/2013 | Ebel et al. |
| 2013/0123241 A1 | | 5/2013 | Ebel et al. |
| 2013/0150354 A1 | | 6/2013 | Ebel et al. |
| 2013/0172348 A1 | | 7/2013 | Ebel et al. |
| 2013/0184299 A1 | | 7/2013 | Ebel et al. |
| 2013/0217728 A1 | | 8/2013 | Ebel et al. |

FOREIGN PATENT DOCUMENTS

| | | |
|---|---|---|
| CA | 2687931 A1 | 12/2008 |
| CA | 2704883 A1 | 5/2009 |
| CA | 2705405 A1 | 5/2009 |
| FR | 2854158 A1 | 10/2004 |
| GB | 2068961 A | 8/1981 |
| JP | 6229575 | 8/1994 |
| JP | 2008239617 A | 10/2008 |
| JP | 2007500135 | 1/2011 |
| WO | 86/06719 A1 | 11/1986 |

(Continued)

OTHER PUBLICATIONS

Barril, et al., Bioorg. & Med. Chem. Lett. (2006), 16(9), 2543-2548.*
Donnelly, et al., Trends in Pharmacological Sciences, 27, 10, 2006, 546-553.*
Lagu, et al., Bioorg. Med. Chem. Lett., 17 (2007), 4382-4386.*
Kuettel, et al., J. Med. Chem. (2007), 50(23), 5833-5839.*
Xu, Ping, et al., Synthesis and Anticonvulsant Activity of 3-(substituted piperazino)-6-(substituted phenyl)pyridazines, Chemical Abstracts Service, 1991, 23(6), 477-480.
International Search Report for PCT/EP2008/056573; mailed Jan. 14, 2009.
Hu, Wenhui, et al; Development of a novel therapeutic suppressor of brain proinflammatory cytokine up-regulation that attenuates synaptic dysfunction and behavioral deficits; Science Direct; Bioorganic & Medicinal Chemistry Letters 17 (2007) 414-418.

(Continued)

*Primary Examiner* — Emily Bernhardt
*Assistant Examiner* — Cecilia M Jaisle
(74) *Attorney, Agent, or Firm* — Michael P. Morris; Edward S. Lazer

(57) ABSTRACT

The present invention relates to novel antagonists for CCR2 (CC chemokine receptor 2) and their use for providing medicaments for treating conditions and diseases, especially pulmonary diseases like asthma and COPD.

4 Claims, No Drawings

(56) References Cited

FOREIGN PATENT DOCUMENTS

| | | | |
|---|---|---|---|
| WO | 8606719 | A1 | 11/1986 |
| WO | 99/21834 | A1 | 5/1999 |
| WO | 00/59502 | A1 | 10/2000 |
| WO | 0066558 | A1 | 11/2000 |
| WO | 0190101 | A1 | 11/2001 |
| WO | 03037271 | A2 | 5/2003 |
| WO | 03/051797 | A2 | 6/2003 |
| WO | 03/066604 | A2 | 8/2003 |
| WO | 03/074500 | A2 | 9/2003 |
| WO | 03/104223 | A1 | 12/2003 |
| WO | 2004/024710 | A1 | 3/2004 |
| WO | 2004074438 | A2 | 9/2004 |
| WO | 2004080976 | A1 | 9/2004 |
| WO | 2004/101546 | A1 | 11/2004 |
| WO | 2005/009976 | A1 | 2/2005 |
| WO | 2005/014571 | A1 | 2/2005 |
| WO | 2005060665 | A2 | 7/2005 |
| WO | 2005/084667 | A1 | 9/2005 |
| WO | 2005097751 | A2 | 10/2005 |
| WO | 2005117909 | A2 | 12/2005 |
| WO | 2005118588 | A1 | 12/2005 |
| WO | 2006/001958 | A2 | 1/2006 |
| WO | 2006004741 | A2 | 1/2006 |
| WO | 2006012135 | A1 | 2/2006 |
| WO | 2006/029906 | A1 | 3/2006 |
| WO | 2006021801 | A1 | 3/2006 |
| WO | 2006034440 | A2 | 3/2006 |
| WO | 2006034833 | A1 | 4/2006 |
| WO | WO 2006038734 | * | 4/2006 |
| WO | 2006/050389 | A2 | 5/2006 |
| WO | 2006073592 | A2 | 7/2006 |
| WO | WO 2006072350 | * | 7/2006 |
| WO | 2006088075 | A1 | 8/2006 |
| WO | 2006/113704 | A2 | 10/2006 |
| WO | 2007/003604 | A2 | 1/2007 |
| WO | 2007/016496 | A2 | 2/2007 |
| WO | 2007/022937 | A1 | 3/2007 |
| WO | 2007026959 | A2 | 3/2007 |
| WO | WO 2007105058 | * | 3/2007 |
| WO | 2007038669 | A2 | 4/2007 |
| WO | 2007/053495 | A2 | 5/2007 |
| WO | 2007/053498 | A1 | 5/2007 |
| WO | 2007048779 | A1 | 5/2007 |
| WO | 2007/084868 | A2 | 7/2007 |
| WO | 2007084786 | A1 | 7/2007 |
| WO | 2007092065 | A2 | 8/2007 |
| WO | 2007/100851 | A1 | 9/2007 |
| WO | 2007120574 | A2 | 10/2007 |
| WO | 2007/127448 | A2 | 11/2007 |
| WO | 2007147874 | A1 | 12/2007 |
| WO | 2008083027 | A1 | 7/2008 |
| WO | 2008145681 | A2 | 12/2008 |
| WO | 2009026204 | A1 | 2/2009 |
| WO | 2009043747 | A2 | 4/2009 |
| WO | 2009065919 | A2 | 5/2009 |
| WO | 2009065920 | A2 | 5/2009 |
| WO | 2010017179 | A1 | 2/2010 |
| WO | 2010020432 | A2 | 2/2010 |
| WO | 2010070032 | A1 | 6/2010 |
| WO | 2011073154 | A1 | 6/2011 |
| WO | 2011073155 | A1 | 6/2011 |
| WO | 2011141474 | A1 | 11/2011 |
| WO | 2011141477 | A1 | 11/2011 |
| WO | 2011144501 | A1 | 11/2011 |
| WO | 2011147772 | A1 | 12/2011 |
| WO | 2011151251 | A1 | 12/2011 |
| WO | 2012171863 | A1 | 12/2012 |
| WO | 2013010839 | A1 | 1/2013 |

OTHER PUBLICATIONS

Rowley, Michael, et al; 4 Heterocyclylpiperidines as Selective High-Affinity Ligands at the Human Dopamine D4 Receptor, J. Med. Chemistry 1997, 40, 2374-2385.

Carter, Percy, H., et al; Advances in the Discovery of CC Chemokine Receptor 2 Antagonists; Annual Reports in Medicinal Chemistry (2007) vol. 42 pp. 211-228.

Chabner, Bruce, A., et al; Chemotherapy of Neoplastic Diseases: Antineoplastic Agents: Goodman & Gilman's: The Pharmacological Basis of Therapeutics by Laurence L. Brunton et al (2006) 11th Ed. pp. 1315-1403.

Chemical Abstracts Service, Columbus, OH, US, STN Database, accession No. 837395-83-2, compounds 837395-83-2, date Feb. 25, 2005.

Chemical Abstracts Service, Columbus, OH, US, STN Database, accession No. 837396-471 compounds 837396-471, dated Feb. 25, 2005.

International Preliminary Report on Patentability for PCT/EP2009/067378 Issued Jun. 21, 2011.

International Preliminary Report on Patentability for PCT/EP2010/069549 Issued Jun. 19, 2012.

International Search Report for PCT/EP2009/067378 mailed Apr. 16, 2010.

International Search Report for PCT/EP2010/069549 mailed Feb. 23, 2011.

International Search Report for PCT/EP2010/069550 mailed Feb. 23, 2010.

International Search Report for PCT/EP2011/057539 mailed Jul. 20, 2011.

International Search Report for PCT/EP2011/057545 mailed Jul. 4, 2011.

International Search Report for PCT/EP2011/057550 mailed Jun. 28, 2011.

International Search Report for PCT/EP2011/058355 mailed Aug. 9, 2011.

International Search Report for PCT/EP2011/058668 mailed Jun. 28, 2011.

Poupaert, Jacques, H; Drug Design: Basic Principles and Applications; Encyclopedia of Pharmaceutical Technology (2007) 3rd edition pp. 1362-1369.

U.S. Appl. No. 13/696,859, filed Nov. 8, 2012.
U.S. Appl. No. 13/696,860, filed Nov. 8, 2012.
U.S. Appl. No. 13/699,325, filed Nov. 21, 2012.
U.S. Appl. No. 13/700,752, filed Nov. 29, 2012.

Chemical Abstracts Service, Columbus, OH, US, Yamashita, Hiroshi et al: "Preparation of benzothiophenylpiperazine derivatives for treatment of central nervous system diseases", XP002528684 retrieved from STN. Database accession No. 2008:1217060, Compound RN: 928251-63-2 *abstract* & JP 2008 239617 A (Ohtsuka Pharmaceutical Co., Ltd, Japan) Oct. 9, 2008.

Chemical Abstracts Service, Columbus, OH; US; Ledeboer; Mark W. et al: "Pyrrolopyridines useful as inhibitors of protein kinase and their prepration, pharmaceutical compositions, and use in the treatment of various diseases", XP002528685 retrieved from STN, Database accession No. 2006:1252802 Compounds RN: 916172-93-5, 916172-95-7 *abstract* & WO 2006/127587 A1 (Vertex Pharmaceuticals Incorporated; USA) Nov. 30, 2006.

Cuzzocrea, Salvstore; Shock, Inflammation and PARP; Pharmacological Research (2005) vol. 52 pp. 72-82.

U.S. Appl. No. 13/523,220, filed Jun. 14, 2012.
U.S. Appl. No. 13/548,321, filed Jul. 13, 2012.
U.S. Appl. No. 13/698,065, filed Nov. 15, 2012.
U.S. Appl. No. 13/949,696, filed Jul. 24, 2013, Inventor: Heiner Ebel.
Notice of Abandonment mailed Aug. 16, 2013, for U.S. Appl. No. 13/140,591, filed Aug. 10, 2011. Inventor: Heiner Ebel.

Cannon, J.G., et al., Chapter Nineteen in Burger's Medicinal Chemistry and Drug Discovery, Fifth Edition, vol. 1., Principals and Practice, Wiley-Interscience 1995, p. 783-802, 784.

Sheridan, R.P., et al., "The Most Common Chemical Replacements in drug-like compounds", J. Chem. Inf. Comp. Sci., 2002, V. 42, p. 103-108.

Rival, Y. et al., "5-HT3 Antagonists Derived from Aminopyridazine-type Muscarinic M1 Agonists", Journal of Medicinal Chemistry, 1998, V.41, p. 311-317.

Wenhui, Hu. et al., "Development of a novel therapeutic suppressor of brain proinflammatory cytokine up-regulation that attenuates synaptic dysfunction and behavioural deficits", Bioorg. Medicine Chem. Letter, 2007, v. 17, p. 414-418.

(56) References Cited

OTHER PUBLICATIONS

Castro, ME, et al., "Prridazine derivatives XII. Synthesis and antipsychotic-antidepressant activity of some butyrophenone derivatives of 6-phenylpyridazine", European Journal of Medicinal Chemistry, 1994, v. 29, p. 831-839.

E.A. Steck et al., "Some 6-Aryl-3-(basically-substituted) Pyridazines", Journal of Heterocyclic Chemistry, 1975, v. 12, No. 5, p. 1009-1013.

Refaat, Hanan, et al., "Bulletin of the Faculty of Pharmacy", (Cair University) Database Caplus on STN, Entered STN 2005, vol. 42, No. 2, p. 415-423.

* cited by examiner

CCR2 RECEPTOR ANTAGONISTS AND USES THEREOF

RELATED APPLICATIONS

This application is a 371 of International Application No. PCT/EP2008/056573, filed May 29, 2008, which claims priority to European Patent Application No 07109376.9, filed May 31 2007, the contents of which are incorporated herein by reference in their entirety.

FIELD OF INVENTION

The present invention relates to novel antagonists for CCR2 (CC chemokine receptor 2) and their use for providing medicaments for treating conditions and diseases, especially pulmonary diseases like asthma and COPD.

BACKGROUND OF THE INVENTION

It is widely accepted that numerous conditions and diseases involve inflammatory processes. Such inflammations are critically triggered and/or promoted by the activity of macrophages, which are formed by differentiation out of monocytes. It has further been found that monocytes are characterized by, e.g., a high expression of membrane-resident CCR2, whereas the CCR2 expression in macrophages is lower. CCR2 is a critical regulator of monocytes trafficking, which can be described as the movement of the monocytes towards an inflammation along a gradient of monocyte chemoattractant proteins (MCP-1, MCP-2, MCP-3, MCP-4).

Therefore, in order to reduce macrophage-induced inflammation, it would be desirable to block the monocyte CCR2 by an antagonist, so that the monocytes can be less triggered to move towards an inflammation area for conversion into macrophages.

Based on the aforesaid there is a need for providing effective antagonists for CCR2, which are pharmacologically acceptable.

DESCRIPTION OF THE INVENTION

The present inventors have found that such effective CCR2 inhibitors can be provided by compounds according to general formula (I),

A-L-D-L'-E-G wherein

A is a group selected from a branched or unbranched, saturated or unsaturated $C_1$-$C_6$ carbon chain, optionally comprising one or more heteroatoms selected from N, O and S and optionally being substituted by one or more groups selected from halogen, —$CF_3$, —$OCF_3$, =O, —OH, —O—$C_1$-$C_6$-alkyl, —C(O)—$C_1$-$C_6$-alkyl, —$C_1$-$C_4$-alkylene-C(O)—$C_1$-$C_4$-alkylene-, —$C_1$-$C_4$-alkylene-O—$C_1$-$C_4$— alkyl, —C(O)—N($R^1$,$R^{1'}$) and —N($R^2$,$R^{2'}$), with $R^1$ and $R^{1'}$ and $R^2$ and $R^{2'}$ being independently selected from —H or substituted or unsubstituted-$C_1$-$C_6$-alkyl, —$C_2$-$C_6$-alkenyl, —$C_2$-$C_6$-alkynyl, or wherein $R^1$ and $R^{1'}$ and $R^2$ and $R^{2'}$, respectively, are bridged via a substituted or unsubstituted —$C_2$-$C_8$-alkylene- by forming a ring, or —N($R^3$,$R^{3'}$) with $R^3$ and $R^{3'}$ being independently selected from —H and —$C_1$-$C_4$-alkyl, —$C_0$-$C_4$-alkylene-$C_3$-$C_8$-cycloalkyl, —$C_1$-$C_6$-alkyl-N($R^4$,$R^{4'}$) with $R^4$ and $R^{4'}$ independently being selected from H and —$C_1$-$C_6$-alkyl, or $R^4$ and $R^{4'}$ being bridged via a —$C_2$-$C_8$-alkylene-, thereby forming a ring, or a 4-8-membered aromatic or aliphatic ring optionally comprising one or more hetero atoms selected from N, O and S and being optionally substituted by one or more $R^5$ being selected from —$C_1$-$C_6$-alkyl, —$C_3$-$C_8$-cycloalkyl, —$C_0$-$C_4$-alkylene-$C_5$-$C_{10}$-aryl, —$C_0$-$C_4$-alkylene-$C_5$-$C_{10}$-heteroaryl, —$C_0$-$C_4$-alkylene-$C_5$-$C_{10}$-cycloalkyl, —$C_0$-$C_4$-alkylene-$C_5$-$C_{10}$-heterocyclyl, —$C_1$-$C_4$-alkylene-O—$C_1$-$C_4$-alkyl, —$C_3$-$C_8$-cycloalkyl-$C_5$-$C_{10}$-aryl, —$C_3$-$C_8$-cycloalkyl-$C_5$-$C_{10}$-heteroaryl, and saturated, unsaturated or aromatic 3-10 membered rings optionally comprising one or more heteroatoms selected from N, O and S, wherein $R^5$ is optionally substituted by one or more -halogen, —$CF_3$, —$OCF_3$, =O, —OH, —O—$C_1$-$C_4$-alkyl, —$C_1$-$C_4$-alkyl, —$C_5$-$C_{10}$-aryl, —$C_5$-$C_{10}$-heteroaryl, or —$C_0$-$C_4$-alkyl-N($R^6$,$R^{6'}$) with $R^6$ and $R^{6'}$ independently selected from —H and —$C_1$-$C_4$-alkyl, L is a linker selected from a single bond, —NH—, —$SO_2$—, or M, with M being selected from —$C_1$-$C_8$-alkylene-, —$C_2$-$C_8$-alkenylen-, —$C_2$-$C_8$-alkynylen-, and M optionally comprising one or more —NH—, —N($C_1$-$C_4$-alkylene)- groups, —$C_1$-$C_4$-alkylene-O—$C_1$-$C_4$-alkylene-, and M optionally being substituted by one or more =O groups, D is a 4-8-membered ring optionally comprising 1 to 3 hetero atoms selected from N, O and S, D further comprising atoms Z and Z', wherein Z and Z' are independently selected from C and N, and wherein D is bonded to L via Z and to L' via Z', respectively, wherein D is optionally substituted by one or more groups selected from —$C_1$-$C_4$-alkyl, =O, —OH, —F, —$CF_3$, L' is a group selected from a single bond, —$C_1$-$C_4$-alkylene-, —NH—, —N($C_1$-$C_4$-alkyl)-, —N($C_3$-$C_6$-cycloalkyl)-, —N(—$C_1$-$C_3$-alkylene-$C_3$-$C_6$-cycloalkyl)-, —O—, —S—, E is an unsaturated or aromatic 4- to 8-membered heterocycle comprising two neighbouring N atoms, which do not form bonds to L' or G, and E being optionally substituted by one or more —$C_1$-$C_4$-alkyl, halogen, —$CF_3$, —$CCl_3$, —$CBr_3$, —CN, OH and —$OCF_3$; or —$C_3$-$C_8$-cycloalkyl optionally substituted by one or more halogen; or —$C_3$-$C_8$-cycloalkenyl optionally being substituted by one or more halogen; or —$C_5$-$C_{10}$-aryl, optionally comprising one or more hetero atoms selected from N, O, S, and optionally substituted by one or more substituent selected from halogen; or —$C_1$-$C_4$-alkyl-$C_3$-$C_8$-cycloalkyl, —$C_1$-$C_4$-alkyl-$C_5$-$C_{10}$-aryl and —$C_1$-$C_4$-alkyl-$C_5$-$C_{10}$-heteroaryl, G is a group selected from —$CF_3$, —$CCl_3$, —$CBr_3$, halogen; or —$C_5$-$C_{10}$-aryl, optionally comprising one or more hetero atoms selected from N, O, S, and optionally substituted with one or more groups selected from -halogen, —$CF_3$, —$CBr_3$, —$CCl_3$, —$C_1$-$C_4$-alkyl, —$C_2$-$C_4$-alkenyl, —$C_2$-$C_4$-alkynyl, —O—$C_1$-$C_4$-alkyl, —OH, —S—$C_1$-$C_4$-alkyl, —CN, —$OCF_3$, or —X—$C_1$-$C_4$-alkylene-X'—, wherein X and X' bond to neighbouring atoms of G for ring closure, and wherein X and X' are independently selected from, —$CH_2$—, —O—, —N—, —S—, —C(O)—, —C(O)—NH—, —C(O)—O—; or —$C_5$-$C_{10}$-heteroaryl, —$C_3$-$C_8$-cycloalkenyl, —$C_3$-$C_8$-cycloalkyl, optionally in form of their individual optical isomers, mixtures of their individual optical isomers, or racemates, as well as in form of their acid addition salts with pharmacologically acceptable acids, as well as in form of their solvates and/or hydrates.

In a preferred embodiment the present invention provides compounds according to formula (I), wherein A is a group selected from a branched or unbranched, saturated or unsaturated $C_1$-$C_6$ carbon chain, optionally comprising one or more heteroatoms selected from N, O and S and optionally being substituted by one or more groups selected from halogen, —$CF_3$, —$OCF_3$, =O, —OH, —O—$C_1$-$C_6$-alkyl, —C(O)—$C_1$-$C_6$-alkyl, —$C_1$-$C_4$-alkylene-C(O)—$C_1$-$C_4$-alkylene-, —C(O)—N($R^1$,$R^{1'}$), —N($R^2$,$R^{2'}$) with $R^1$ and $R^{1'}$ and $R^2$ and $R^{2'}$ being independently selected from —H or substituted or unsubstituted-$C_1$-$C_6$-alkyl, —$C_2$-$C_6$-alkenyl, —$C_2$-$C_6$-alkynyl, or wherein $R^1$ and $R^{1'}$ and $R^2$ and $R^{2'}$, respectively, are bridged via a substituted or unsubstituted —$C_2$-$C_8$-alkylene- by forming a ring, or —N($R^3$,$R^{3'}$) with $R^3$ and $R^{3'}$ being independently selected from —H and —$C_1$-$C_4$-alkyl, —$C_0$-$C_4$-alkyl-$C_3$-$C_8$-cycloalkyl, —$C_1$-$C_6$-alkyl-N($R^4$,$R^{4'}$) with $R^4$ and $R^{4'}$ independently being selected from H and —$C_1$-$C_6$-alkyl, or $R^4$ and $R^{4'}$ being bridged via a —$C_2$-$C_8$-alkylene-, thereby forming a ring, or a 4-8-membered aromatic or aliphatic ring optionally comprising one or more heteroatoms selected from N, O and S and being optionally substituted by one or more $R^5$ being selected from —F, —Cl, —Br, —OH, —$CF_3$, =O, —$C_1$-$C_6$-alkyl, —$C_3$-$C_6$-cycloalkyl, -benzyl, 2-Ethoxy-ethyl, dimethyl-amino-methyl, 2-dimethyl-amino-ethyl, 3-dimethyl-amino-propyl, —N($CH_3$)$_2$, —N($C_2H_5$)$_2$,

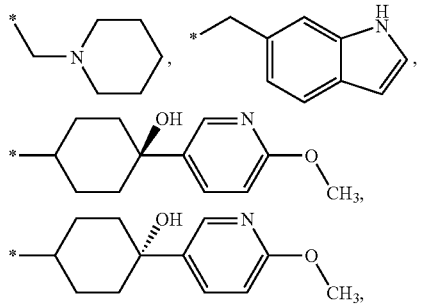

wherein $R^5$ is optionally substituted by one or more —$C_1$-$C_4$-alkyl or —$C_1$-$C_4$—N($R^6$,$R^{6'}$) with $R^6$ and $R^{6'}$ independently selected from —H and —$C_1$-$C_4$-alkyl, L is a linker selected from a single bond, —NH—, —$SO_2$—, or M, with M being selected from —$C_1$-$C_6$-alkylene-, —$C_2$-$C_6$-alkenylen-, —$C_2$-$C_6$-alkynylen-, and M optionally comprising one or more —NH—, —N($C_1$-$C_4$-alkylene)- groups, and M optionally being substituted by one or more =O groups, D is a 4-8-membered ring optionally comprising 1 to 3 hetero atoms selected from N, O and S, D further comprising atoms Z and Z', wherein Z and Z' are independently selected from C and N, and wherein D is bonded to L via Z and to L' via Z', respectively, L' is a group selected from a single bond, —$C_1$-$C_4$-alkylene-, —NH—, —N($C_1$-$C_4$-alkyl)-, —O—, —S—, E is an unsaturated or aromatic 4- to 8-membered heterocycle comprising two neighbouring N atoms, which do not form bonds to L' or G, E being optionally substituted by one or more —$C_1$-$C_4$-alkyl, -halogen, —$CF_3$, —$CBr_3$, —$CCl_3$; or —$C_5$-$C_{10}$-aryl optionally comprising one or more hetero atoms selected from N, O, S and optionally substituted by one or more substituents selected from halogen; or —$C_3$-$C_8$-cycloalkyl, —$C_1$-$C_4$-alkyl-$C_3$-$C_8$-cycloalkyl, —$C_1$-$C_4$-alkyl-$C_5$-$C_{10}$-aryl, —$C_1$-$C_4$-alkyl-$C_5$-$C_{10}$-heteroaryl, G is a group selected from —$CF_3$, —$CCl_3$, —$CBr_3$, halogen, —$C_5$-$C_{10}$-aryl, optionally comprising one or more hetero atoms selected from N, O, S, and optionally substituted with one or more groups selected from -halogen, —$CF_3$, —$CBr_3$, —$CCl_3$, —$C_1$-$C_4$-alkyl, —O—$C_1$-$C_4$-alkyl, —OH, —S -$C_1$-$C_4$— alkyl, —CN, —$OCF_3$, optionally in form of their individual optical isomers, mixtures of their individual optical isomers, or racemates, as well as in form of their acid addition salts with pharmacologically acceptable acids, as well as in form of their solvates and/or hydrates.

In another preferred embodiment the present invention provides compounds according to formula (I), wherein A is a group selected from —$C_1$-$C_6$-alkyl, —$C_2$-$C_6$-alkenyl, —$C_2$-$C_6$-alkynyl, —N($CH_3$)$_2$, —N($C_2H_5$)$_2$, —$C_1$-$C_6$-alkyl-N($R^4$,$R^{4'}$) with $R^4$ and $R^{4'}$ independently being selected from H and —$C_1$-$C_6$-alkyl, or $R^4$ and $R^{4'}$ being bridged via a —$C_2$-$C_8$-alkylene-, by forming a ring, or a 5-7-membered aromatic or aliphatic ring optionally comprising one or two heteroatoms selected from N and O and being optionally substituted by one or more —F, —OH, —$CF_3$, —$C_1$-$C_4$-alkyl, -cyclopropyl, -cyclobutyl, -cyclopentyl, -cyclohexyl, -benzyl, -2-Ethoxy-ethyl, -dimethyl-amino-methyl, -2-dimethyl-amino-ethyl, -3-dimethyl-amino-propyl, —N($CH_3$)$_2$, —N($C_2H_5$)$_2$,

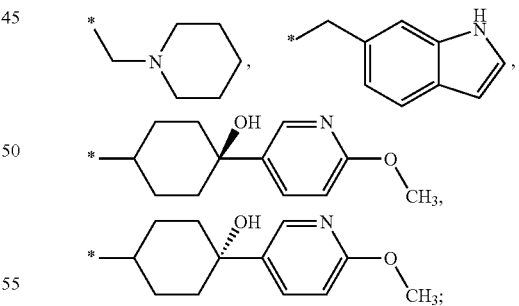

L is a linker selected from a single bond, —NH—, —($CH_2$)$_n$—, —NH—($CH_2$)$_m$—, —$NCH_3$—($CH_2$)$_o$—, —C(O)—NH—($CH_2$)$_p$—, with m, n, o and p being independently selected from 1 to 4, —$C_0$-$C_6$-alkylene-C(O)—$C_0$-$C_6$-alkylene-, —$SO_2$—, D is a 5-, 6- or 7-membered ring optionally comprising one or more N atoms, further comprising atoms Z and Z', wherein Z and Z' are independently selected from C and N, and wherein D is bonded to L via Z and to L' via Z', respectively, L' is a group selected from
a single bond, —$C_1$-$C_4$-alkylene-, —NH—, —N($C_1$-$C_4$-alkyl)-, —O—, —S—, E is an
unsaturated or aromatic 5- or 6-membered heterocycle comprising two neighbouring N atoms, which do not form bonds to L' or G, E being optionally substituted by one or more —$C_1$-$C_4$-alkyl, halogen, —$CF_3$, —$CCl_3$, —$CBr_3$, —$C_3$-$C_8$-cycloalkyl, or —$C_5$-$C_{10}$-aryl, optionally comprising one or more hetero atoms selected from N, O, S, and optionally substituted with one or more substituents selected from halogen; or
—$C_3$-$C_8$-cycloalkyl, —$C_1$-$C_4$-alkyl-$C_5$-$C_{10}$-aryl, —$C_1$-$C_4$-alkyl-$C_5$-$C_{10}$-heteroaryl, G is a group selected from
—$CF_3$ and
—phenyl optionally substituted with one or more groups selected from —F, —Br, —$C_1$, $CF_3$, —$CH_3$, —$OCH_3$, —CH($CH_3$)$_2$, optionally in form of their individual optical isomers, mixtures of their individual optical isomers, or racemates, as well as in form of their acid addition salts with pharmacologically acceptable acids, as well as in form of their solvates and/or hydrates.

In another preferred embodiment the present invention provides compounds according to formula (I), wherein
A is a group selected from
—$C_1$-$C_4$-alkyl, —N($CH_3$)$_2$, —N($C_2H_5$)$_2$, —$C_1$-$C_4$-alkyl-N($CH_3$)$_2$; or
—phenyl, optionally substituted by

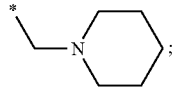

or
—piperidinyl, optionally substituted by one or more —$C_1$-$C_4$-alkyl, -cyclopropyl, -dimethyl-amino-methyl,

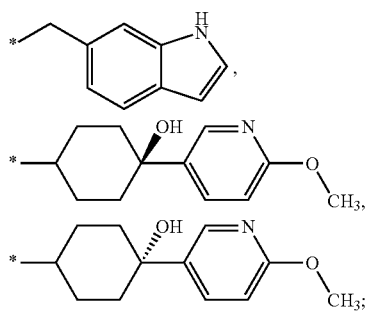

or
—morpholinyl, optionally substituted by one or more —$C_1$-$C_4$-alkyl, -cyclohexyl, -benzyl; or
—cyclohexyl, optionally substituted by one or more —$C_1$-$C_4$-alkyl, —N($CH_3$)$_2$, dimethyl-amino-methyl, 2-dimethyl-amino-ethyl, 3-dimethylamino-propyl; or
—pyrrolidinyl, optionally substituted by one or more —$C_1$-$C_4$-alkyl, 2-Ethoxy-ethyl, -cyclopentyl, -benzyl; or
—piperazinyl, optionally substituted by one or more —$C_1$-$C_4$-alkyl; or
—azepanyl, optionally substituted by one or more —$C_1$-$C_4$-alkyl, L is a linker selected from
a single bond, —NH—, —($CH_2$)—, —NH—($CH_2$)$_m$—, —$NCH_3$—($CH_2$)$_o$—, —C(O)—NH—($CH_2$)$_p$—, with m, n, o and p being independently selected from 1 to 4, —$C_0$-$C_4$-alkylene-C(O)—$C_0$-$C_4$-alkylene-, —$SO_2$—, D is a
5-, 6- or 7-membered saturated ring comprising atoms Z and Z', wherein Z and Z' are independently selected from C and N, and wherein D is bonded to L via Z and to L' via Z', respectively, L' is a group selected from
a single bond, —$C_1$-$C_4$-alkylene-, —NH—, —N($C_1$-$C_4$-alkyl)-, E is a group selected from
—pyrazolyl, -pyridazinyl, wherein the neighboring N atoms do not form bonds to L' or G, E optionally being substituted by one or more groups selected from —$CH_3$, —$CF_3$, -cyclohexyl, -phenyl, -3,4-dichloro-phenyl, -naphthyl, -benzyl, G is a group selected from
—$CF_3$,
—phenyl optionally substituted with one or more groups selected from —F, —Br, —Cl, —$CF_3$, —$CH_3$, —$OCH_3$, —CH($CH_3$)$_2$, optionally in form of their individual optical isomers, mixtures of their individual optical isomers, or racemates, as well as in form of their acid addition salts with pharmacologically acceptable acids, as well as in form of their solvates and/or hydrates.

In another preferred embodiment the present invention provides compounds according to formula (I), wherein
A is a group selected from
—methyl, —N($CH_3$)$_2$, —N($C_2H_5$)$_2$, —$CH_2$—N($CH_3$)$_2$, —CH($CH_3$)$_2$, -piperidin-1-yl, -piperidin-3-yl, -3-dimethylamino -methyl-piperidin-1-yl, -1-methyl-piperidin-2-yl, -1-methyl-piperidin-3-yl, -1-ethyl-piperidin-3-yl, -1-propyl-piperidin-3-yl, -1-i-propyl-piperidin-3-yl, -1-cyclopropyl-piperidin-3-yl, 1-methyl-piperidin-4-yl,

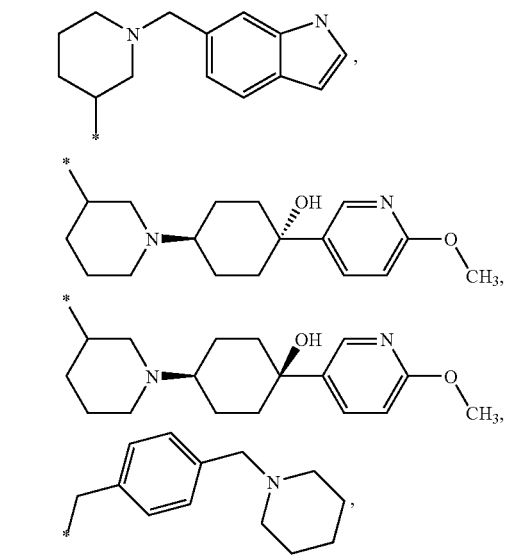

—morpholin-4-yl, -4-i-propyl-morpholin-2-yl, -4-cyclohexyl-morpholin-2-yl, -4-benzyl-morpholin-2-yl, -4-methyl-morpholin-2-yl, -4-methyl-morpholin-3-yl, -cyclohexyl, -3-methyl-cyclohex-1-yl, -4-(2-dimethyl-amino-ethyl)-cyclohex-1-yl, -4-(3-dimethyl-amino-propyl)-cyclohex-1-yl, -4-(dimethyl-amino-methyl)-cyclohex-1-yl, -3-dimethylamino-cyclohex-1-yl, —pyrrolidin-1-yl, -pyrrolidin-3-yl, -1-methyl-pyrrolidin-2-yl, -1-methyl-pyrrolidin-3-yl, -1-(2-Ethoxy-ethyl)-pyrrolidin-3-yl, -1-cyclopentyl-pyrrolidin-3-yl, -1-benzyl-pyrrolidin-3-yl, -1-methyl-piperazin-4-yl, -1-i-propyl-piperazin-3-yl, -1-i-propyl-4-methyl-piperazin-3-yl, -azepan-1-yl, -azepan-3-yl, -1-methyl-azepan-3-yl, L is a linker selected from a single bond, —$CH_2$—, —NH—, —NH—$CH_2$—, —NH—$(CH_2)_2$—, —$NCH_3$—$(CH_2)_2$—, —C(O)—NH—$(CH_2)_3$—, —C(O)—, —C(O)—$CH_2$—, —C(O)—$(CH_2)_2$—, —$SO_2$—, D is a group selected from —pyrrolidinyl, -piperazinyl, -piperidinyl, -1,4-diazepanyl, -cyclohexyl, L' is a group selected from a single bond, —NH—, —$N(CH_3)$—, E is a group selected from —1H-pyrazolyl, -1-methyl-1H-pyrazolyl, -1-cyclohexyl-1H-pyrazolyl, -1-benzyl-1H-pyrazolyl, -1-(naphth-2-yl)-1H-pyrazolyl, -4,4-dimethyl-4H-pyrazolyl, —pyridazinyl, -4-trifluoromethyl-pyridazinyl, -5-methyl-pyridazinyl, -5-phenyl-pyridazinyl, -4-(3,4-dichloro-phenyl)-pyridazinyl, G is a group selected from —$CF_3$, or —4-bromo-phenyl, -3-chloro-phenyl, -4-chloro-phenyl, -3,4-dichloro-phenyl, -3,5-dichloro-phenyl, -2,3-dichloro-phenyl, -2,4-dichloro-phenyl, -2,5-dichloro-phenyl, -3,5-di-trifluoromethyl-phenyl, -3-trifluoromethyl-phenyl, -3-fluoro-5-trifluoromethyl-phenyl, -3-chloro-5-trifluoromethyl-phenyl, -3-chloro-4-trifluoromethyl-phenyl, -3-isopropyl-phenyl, -4-isopropyl-phenyl, -3,5-dimethoxy-phenyl, -3-chloro-4-methoxy-phenyl, -2-methyl-4-chloro-phenyl, optionally in form of their individual optical isomers, mixtures of their individual optical isomers, or racemates, as well as in form of their acid addition salts with pharmacologically acceptable acids, as well as in form of their solvates and/or hydrates.

In another preferred embodiment the present invention provides compounds according to formula (I), wherein A is selected from a branched or unbranched, saturated or unsaturated $C_1$-$C_6$ carbon chain, optionally comprising one or more heteroatoms selected from N, O and S and optionally being substituted by one or more groups selected from halogen, —$CF_3$, —$OCF_3$, =O, —OH, —O—$C_1$-$C_6$-alkyl, —C(O)—$C_1$-$C_6$-alkyl, —$C_1$-$C_4$-alkylene-C(O)—$C_1$-$C_4$-alkylene-, —C(O)—$N(R^1,R^{1'})$, —$N(R^2,R^{2'})$ with $R^1$ and $R^{1'}$ and $R^2$ and $R^{2'}$ being independently selected from —H or substituted or unsubstituted —$C_1$-$C_6$-alkyl, —$C_2$-$C_6$-alkenyl, —$C_2$-$C_6$-alkynyl, or wherein $R^1$ and $R^{1'}$ and $R^2$ and $R^{2'}$, respectively, are bridged via a substituted or unsubstituted —$C_2$-$C_8$-alkylene- by forming a ring, or —$N(R^3,R^{3'})$ with $R^3$ and $R^{3'}$ being independently selected from —H and —$C_1$-$C_4$-alkyl, —$C_0$-$C_4$-alkyl-$C_3$-$C_8$-cycloalkyl, —$C_1$-$C_6$-alkyl-$N(R^4,R^{4'})$ with $R^4$ and $R^{4'}$ independently being selected from —H and —$C_1$-$C_6$-alkyl, or $R^4$ and $R^{4'}$ being bridged via a —$C_2$-$C_8$-alkylene-, thereby forming a ring, or a 4-8-membered aromatic or aliphatic ring optionally comprising one or more heteroatoms selected from N, O and S and being optionally substituted by one or more $R^5$ being selected from —F, —Cl, —Br, —OH, —$CF_3$, =O, —$C_1$-$C_6$-alkyl, —$C_3$-$C_6$-cycloalkyl, -benzyl, 2-Ethoxy-ethyl, dimethyl-amino-methyl, 2-dimethyl-amino-ethyl, 3-dimethyl-amino-propyl, —$N(CH_3)_2$, —$N(C_2H_5)_2$,

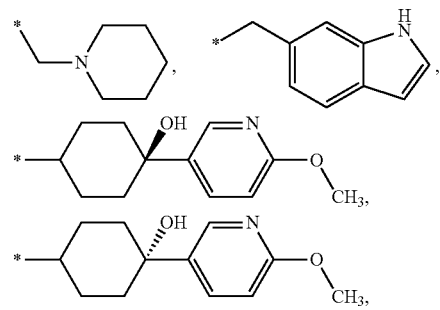

wherein $R^5$ is optionally substituted by one or more —$C_1$-$C_4$-alkyl or —$C_1$-$C_4$—$N(R^6,R^{6'})$ with $R^6$ and $R^{6'}$ independently selected from —H and —$C_1$-$C_4$-alkyl, optionally in form of their individual optical isomers, mixtures of their individual optical isomers, or racemates, as well as in form of their acid addition salts with pharmacologically acceptable acids, as well as in form of their solvates and/or hydrates, wherein L, D, L', E and G are as defined hereinabove or hereinbelow.

In another preferred embodiment the present invention provides compounds according to formula (I), wherein A is selected from —$C_1$-$C_6$-alkyl, —$C_2$-$C_6$-alkenyl, —$C_2$-$C_6$-alkynyl, —$N(CH_3)_2$, —$N(C_2H_5)_2$, —$C_1$-$C_6$-alkyl-$N(R^4,R^{4'})$ with $R^4$ and $R^{4'}$ independently being selected from H and —$C_1$-$C_6$-alkyl, or $R^4$ and $R^{4'}$ being bridged via a —$C_2$-$C_8$-alkylene-, by forming a ring; or a 5-7-membered aromatic or aliphatic ring optionally comprising one or two heteroatoms selected from N and O and being optionally substituted by one or more —F, —OH, —$CF_3$, —$C_1$-$C_4$-alkyl, -cyclopropyl, -cyclobutyl, -cyclopentyl, -cyclohexyl, -benzyl, -2-Ethoxy-ethyl, -dimethyl-amino-methyl, -2-dimethyl-amino-ethyl, -3-dimethyl-amino-propyl, —$N(CH_3)_2$, —$N(C_2H_5)_2$,

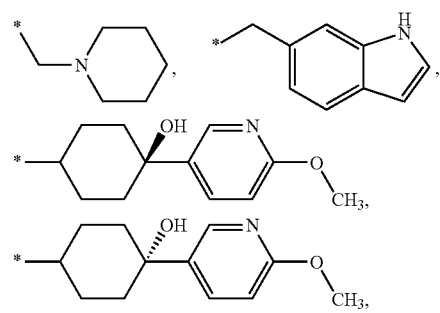

optionally in form of their individual optical isomers, mixtures of their individual optical isomers, or racemates, as well as in form of their acid addition salts with pharmacologically acceptable acids, as well as in form of their solvates and/or hydrates, wherein L, D, L', E and G are as defined hereinabove or hereinbelow.

In another preferred embodiment the present invention provides compounds according to formula (I), wherein A is selected from —$C_1$-$C_4$-alkyl, —$N(CH_3)_2$, —$N(C_2H_5)_2$, —$C_1$-$C_4$-alkyl-$N(CH_3)_2$; or —phenyl, optionally substituted by

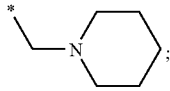

or

—piperidinyl, optionally substituted by one or more —$C_1$-$C_4$-alkyl, -cyclopropyl, -dimethyl-amino-methyl, -dimethyl-amino-methyl,

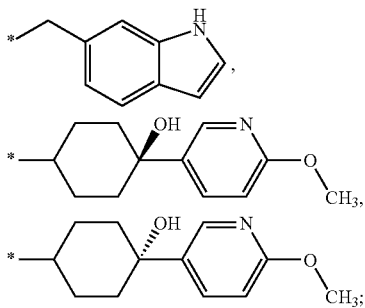

or

—morpholinyl, optionally substituted by one or more —$C_1$-$C_4$-alkyl, -cyclohexyl, -benzyl; or —cyclohexyl, optionally substituted by one or more —$C_1$-$C_4$-alkyl, —$N(CH_3)_2$, dimethyl-amino-methyl, 2-dimethyl-amino-ethyl, 3-dimethylamino-propyl; or —pyrrolidinyl, optionally substituted by one or more —$C_1$-$C_4$-alkyl, 2-Ethoxy-ethyl, -cyclopentyl, -benzyl; or —piperazinyl, optionally substituted by one or more —$C_1$-$C_4$-alkyl; or —azepanyl, optionally substituted by one or more —$C_1$-$C_4$-alkyl, optionally in form of their individual optical isomers, mixtures of their individual optical isomers, or racemates, as well as in form of their acid addition salts with pharmacologically acceptable acids, as well as in form of their solvates and/or hydrates, wherein L, D, L', E and G are as defined hereinabove or hereinbelow.

In another preferred embodiment the present invention provides compounds according to formula (I), wherein A is selected from —methyl, —$N(CH_3)_2$, —$N(C_2H_5)_2$, —$CH_2$—$_{N(CH3)}$$_2$, —$CH(CH_3)_2$, —piperidin-1-yl, -piperidin-3-yl, -3-dimethylamino -methyl-piperidin-1-yl, -1-methyl-piperidin-2-yl, -1-methyl-piperidin-3-yl, -1-ethyl-piperidin-3-yl, -1-propyl-piperidin-3-yl, -1-i-propyl-piperidin-3-yl, -1-cyclopropyl-piperidin-3-yl, -1-methyl-piperidin-4-yl,

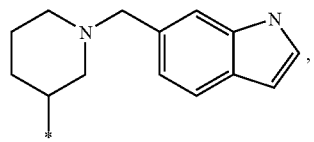

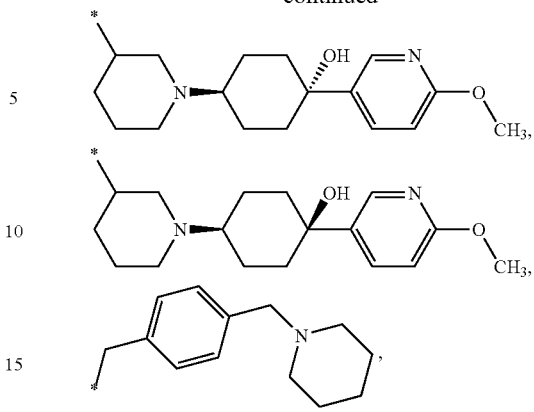

—morpholin-4-yl, -4-i-propyl-morpholin-2-yl, -4-cyclohexyl-morpholin-2-yl, -4-benzyl-morpholin-2-yl, -4-methyl-morpholin-2-yl, -4-methyl-morpholin-3-yl, -cyclohexyl, -3-methyl-cyclohex-1-yl, -4-(2-dimethyl-amino-ethyl)-cyclohex-1-yl, -4-(3-dimethyl- amino-propyl)-cyclohex-1-yl, -4-(dimethyl- amino-methyl)-cyclohex-1-yl, -3-dimethylamino-cyclohex-1-yl, —pyrrolidin-1-yl, -pyrrolidin-3-yl, -1-methyl-pyrrolidin-2-yl, -1-methyl-pyrrolidin-3-yl, -1-(2-Ethoxy-ethyl)-pyrrolidin-3-yl, -1-cyclopentyl-pyrrolidin-3-yl, -1-benzyl-pyrrolidin-3-yl, -1-methyl-piperazin-4-yl, -1-i-propyl-piperazin-3-yl, -1-i-propyl-4-methyl-piperazin-3-yl, -azepan-1-yl, -azepan-3-yl, -1-methyl-azepan-3-yl, optionally in form of their individual optical isomers, mixtures of their individual optical isomers, or racemates, as well as in form of their acid addition salts with pharmacologically acceptable acids, as well as in form of their solvates and/or hydrates, wherein L, D, L', E and G are as defined hereinabove or hereinbelow.

In another preferred embodiment the present invention provides compounds according to formula (I), wherein L is a linker selected from a single bond, —NH—, —$SO_2$—, or M, with M being selected from —$C_1$-$C_6$-alkylene-, —$C_2$-$C_6$-alkenylen-, —$C_2$-$C_6$-alkynylen-, and M optionally comprising one or more —NH—, —$N(C_1$-$C_4$-alkylene)- groups, and M optionally being substituted by one or more =O groups, optionally in form of their individual optical isomers, mixtures of their individual optical isomers, or racemates, as well as in form of their acid addition salts with pharmacologically acceptable acids, as well as in form of their solvates and/or hydrates, wherein A, D, L', E and G are as defined hereinabove or hereinbelow.

In another preferred embodiment the present invention provides compounds according to formula (I), wherein L is a linker selected from a single bond, —NH—, —$(CH_2)_n$—, —NH—$(CH_2)_m$—, —$NCH_3$—$(CH_2)_o$—, —C(O)—NH—$(CH_2)_p$—, with m, n, o and p being independently selected from 1 to 4, —$C_0$-$C_6$-alkylene-C(O)—$C_0$-$C_6$-alkylene-, —$SO_2$—, optionally in form of their individual optical isomers, mixtures of their individual optical isomers, or racemates, as well as in form of their acid addition salts with pharmacologically acceptable acids, as well as in form of their solvates and/or hydrates, wherein A, D, L', E and G are as defined hereinabove or hereinbelow.

In another preferred embodiment the present invention provides compounds according to formula (I), wherein L is a linker selected from a single bond, —CH$_2$—, —NH—, —NH—CH$_2$—, —NH—(CH$_2$)$_2$—, —NCH$_3$—(CH$_2$)$_2$—, —C(O)—NH—(CH$_2$)$_3$—, —C(O)—, —C(O)—CH$_2$—, —C(O)—(CH$_2$)$_2$—, —SO$_2$—, optionally in form of their individual optical isomers, mixtures of their individual optical isomers, or racemates, as well as in form of their acid addition salts with pharmacologically acceptable acids, as well as in form of their solvates and/or hydrates, wherein A, D, L', E and G are as defined hereinabove or hereinbelow.

In another preferred embodiment the present invention provides compounds according to formula (I), wherein D is selected from 4-8-membered ring optionally comprising 1 to 3 hetero atoms selected from N, O and S, D further comprising atoms Z and Z', wherein Z and Z' are independently selected from C and N, and wherein D is bonded to L via Z and to L' via Z', respectively, optionally in form of their individual optical isomers, mixtures of their individual optical isomers, or racemates, as well as in form of their acid addition salts with pharmacologically acceptable acids, as well as in form of their solvates and/or hydrates, wherein A, L, L', E and G are as defined hereinabove or hereinbelow.

In another preferred embodiment the present invention provides compounds according to formula (I), wherein D is selected from 5-, 6- or 7-membered rings optionally comprising one or more N atoms, further comprising atoms Z and Z', wherein Z and Z' are independently selected from C and N, and wherein D is bonded to L via Z and to L' via Z', respectively, optionally in form of their individual optical isomers, mixtures of their individual optical isomers, or racemates, as well as in form of their acid addition salts with pharmacologically acceptable acids, as well as in form of their solvates and/or hydrates, wherein A, L, L', E and G are as defined hereinabove or hereinbelow.

In another preferred embodiment the present invention provides compounds according to formula (I), wherein D is selected from 5-, 6- or 7-membered saturated rings comprising atoms Z and Z', wherein Z and Z' are independently selected from C and N, and wherein D is bonded to L via Z and to L' via Z', respectively, optionally in form of their individual optical isomers, mixtures of their individual optical isomers, or racemates, as well as in form of their acid addition salts with pharmacologically acceptable acids, as well as in form of their solvates and/or hydrates, wherein A, L, L', E and G are as defined hereinabove or hereinbelow.

In another preferred embodiment the present invention provides compounds according to formula (I), wherein D is selected from —pyrrolidinyl, -piperazinyl, -piperidinyl, -1,4-diazepanyl, -cyclohexyl, optionally in form of their individual optical isomers, mixtures of their individual optical isomers, or racemates, as well as in form of their acid addition salts with pharmacologically acceptable acids, as well as in form of their solvates and/or hydrates, wherein A, L, L', E and G are as defined hereinabove or hereinbelow.

In another preferred embodiment the present invention provides compounds according to formula (I), wherein L' is a linker selected from a single bond, —C$_1$-C$_4$-alkylene-, —NH—, —N(C$_1$-C$_4$-alkyl)-, —O—, —S—, optionally in form of their individual optical isomers, mixtures of their individual optical isomers, or racemates, as well as in form of their acid addition salts with pharmacologically acceptable acids, as well as in form of their solvates and/or hydrates, wherein A, L, D, E and G are as defined hereinabove or hereinbelow.

In another preferred embodiment the present invention provides compounds according to formula (I), wherein L' is a linker selected from a single bond, —C$_1$-C$_4$-alkylene-, —NH—, —N(C$_1$-C$_4$-alkyl)-, optionally in form of their individual optical isomers, mixtures of their individual optical isomers, or racemates, as well as in form of their acid addition salts with pharmacologically acceptable acids, as well as in form of their solvates and/or hydrates, wherein A, L, D, E and G are as defined hereinabove or hereinbelow.

In another preferred embodiment the present invention provides compounds according to formula (I), wherein L' is a linker selected from a single bond, —NH—, —N(CH$_3$)—, optionally in form of their individual optical isomers, mixtures of their individual optical isomers, or racemates, as well as in form of their acid addition salts with pharmacologically acceptable acids, as well as in form of their solvates and/or hydrates, wherein A, L, D, E and G are as defined hereinabove or hereinbelow.

In another preferred embodiment the present invention provides compounds according to formula (I), wherein E is an unsaturated or aromatic 4- to 8-membered heterocycle comprising two neighbouring N atoms, which do not form bonds to L' or G, E being optionally substituted by one or more —C$_1$-C$_4$-alkyl, -halogen, —CF$_3$, —CBr$_3$, —CCl$_3$; or —C$_5$-C$_{10}$-aryl optionally comprising one or more hetero atoms selected from N, O, S and optionally substituted by one or more substituents selected from halogen; or —C$_3$-C$_8$-cycloalkyl, —C$_1$-C$_4$-alkyl-C$_3$-C$_8$-cycloalkyl, —C$_1$-C$_4$-alkyl-C$_5$-C$_{10}$-aryl, —C$_1$-C$_4$-alkyl-C$_5$-C$_{10}$-heteroaryl, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (I), wherein E is an unsaturated or aromatic 5- or 6-membered heterocycle comprising two neighbouring N atoms, which do not form bonds to L' or G, E being optionally substituted by one or more —C$_1$-C$_4$-alkyl, halogen, —CF$_3$, —CCl$_3$, —CBr$_3$, —C$_3$-C$_8$-cycloalkyl, or —C$_5$-C$_{10}$-aryl, optionally comprising one or more hetero atoms selected from N, O, S, and optionally substituted with one or more substituents selected from halogen; or —C$_3$-C$_8$-cycloalkyl, —C$_1$-C$_4$-alkyl-C$_5$-C$_{10}$-aryl, —C$_1$-C$_4$-alkyl-C$_5$-C$_{10}$-heteroaryl, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (I), wherein E is selected from pyrazolyl, pyridazinyl, wherein the neighbouring N atoms do not form bonds to L' or G, E optionally being substituted by one or more groups selected from —CH$_3$, —CF$_3$, -cyclohexyl, -phenyl, -3,4-dichloro-phenyl, -naphthyl, -benzyl, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (I), wherein E is selected from —1H-pyrazolyl, -1-methyl-1H-pyrazolyl, -1-cyclohexyl-1H-pyrazolyl, -1-benzyl-1H-pyrazolyl, -1-(naphth-2-yl)-1H-pyrazolyl, -4,4-dimethyl-4H-pyrazolyl, —pyridazinyl, -4-trifluoromethyl-pyridazinyl, -5-methyl-pyridazinyl, -5-phenyl-pyridazinyl, -4-(3,4-dichloro-phenyl)-pyridazinyl, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (I), wherein G is selected from —CF$_3$, —CCl$_3$, —CBr$_3$, -halogen, —C$_5$-C$_{10}$-aryl, optionally comprising one or more hetero atoms selected from N, O, S, and optionally substituted with one or more groups selected from -halogen, —CF$_3$, —CBr$_3$, —CCl$_3$, —C$_1$-C$_4$-alkyl, —O—C$_1$-C$_4$-alkyl, —OH, —S—C$_1$-C$_4$-alkyl, —CN, —OCF$_3$, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and E are as defined hereinabove or hereinbelow.

In another preferred embodiment the present invention provides compounds according to formula (I), wherein G is selected from —CF$_3$ and —phenyl optionally substituted with one or more groups selected from —F, —Br, —Cl, —CF$_3$, —CH$_3$, —OCH$_3$, —CH(CH$_3$)$_2$, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and E are as defined hereinabove or hereinbelow.

In another preferred embodiment the present invention provides compounds according to formula (I), wherein G is selected from —CF$_3$, or —4-bromo-phenyl, -3-chloro-phenyl, -4-chloro-phenyl, -3,4-dichloro-phenyl, -3,5-dichloro-phenyl, -2,3-dichloro-phenyl, -2,4-dichloro-phenyl, -2,5-dichloro-phenyl, -3,5-di-trifluoromethyl-phenyl, -3-trifluoromethyl-phenyl, -3-fluoro-5-trifluoromethyl-phenyl, -3-chloro-5-trifluoromethyl-phenyl, -3-chloro-4-trifluoromethyl-phenyl, -3-isopropyl-phenyl, -4-isopropyl-phenyl, -3,5-dimethoxy-phenyl, -3-chloro-4-methoxy-phenyl, -2-methyl-4-chloro-phenyl, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and E are as defined hereinabove or hereinbelow.

In another preferred embodiment the present invention provides compounds according to formula (I), wherein E is substituted or unsubstituted pyrazole, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (Ia),

(Ia)

wherein R$^{het}$ and R$^{ring}$ are independently selected from H, —C$_1$-C$_4$-alkyl, -halogen, —CF$_3$, —CBr$_3$, —CCl$_3$; or —C$_5$-C$_{10}$-aryl optionally comprising one or more hetero atoms selected from N, O, S and optionally substituted by one or more substituents selected from halogen; or —C$_3$-C$_8$-cycloalkyl, —C$_1$-C$_4$-alkyl-C$_3$-C$_8$-cycloalkyl, —C$_1$-C$_4$-alkyl-C$_5$-C$_{10}$-aryl, —C$_1$-C$_4$-alkyl-C$_5$-C$_{10}$-heteroaryl, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (Ia'),

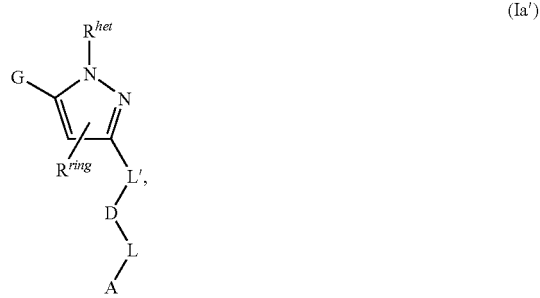

(Ia')

wherein R$^{het}$ and R$^{ring}$ are independently selected from H, —C$_1$-C$_4$-alkyl, -halogen, —CF$_3$, —CBr$_3$, —CCl$_3$; or —C$_5$-C$_{10}$-aryl optionally comprising one or more hetero atoms selected from N, O, S and optionally substituted by one or more substituents selected from halogen; or —$C_3$-$C_8$-cyclo alkyl, —$C_1$-$C_4$-alkyl-$C_3$-$C_8$-cyclo alkyl, —$C_1$-$C_4$-alkyl-$C_5$-$C_{10}$- aryl, —$C_1$-$C_4$— alkyl-$C_5$-$C_{10}$-hetero aryl, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (Ia) or (Ia'), wherein $R^{het}$ and $R^{ring}$ are independently selected from H, —$C_1$-$C_4$-alkyl, halogen, —$CF_3$, —$CCl_3$, —$CBr_3$; or —$C_3$-$C_8$-cycloalkyl, or —$C_5$-$C_{10}$-aryl, optionally comprising one or more hetero atoms selected from N, O, S, and optionally substituted with one or more substituents selected from halogen; or —$C_3$-$C_8$-cycloalkyl, —$C_1$-$C_4$-alkyl-$C_5$-$C_{10}$-aryl, —$C_1$-$C_4$-alkyl-$C_5$-$C_{10}$-heteroaryl, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (Ia) or (Ia'), wherein $R^{het}$ and $R^{ring}$ are independently selected from H, —$CH_3$, —$CF_3$, -cyclohexyl, -phenyl, -3,4-dichloro-phenyl, -naphthyl, —benzyl, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (I), wherein E is substituted or unsubstituted pyridazine, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (Ib),

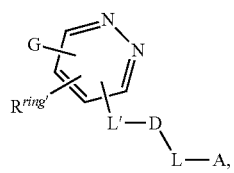

(Ib)

wherein $R^{ring'}$ is selected from H, —$C_1$-$C_4$-alkyl, -halogen, —$CF_3$, —$CBr_3$, —$CCl_3$; or —$C_5$-$C_{10}$-aryl optionally comprising one or more hetero atoms selected from N, O, S and optionally substituted by one or more substituents selected from halogen; or —$C_3$-$C_8$-cycloalkyl, —$C_1$-$C_4$-alkyl-$C_3$-$C_8$-cycloalkyl, $C_1$-$C_4$ alkyl-$C_5$-$C_{10}$-aryl, —$C_1$-$C_4$-alkyl-$C_5$-$C_{10}$-heteroaryl, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (Ib'),

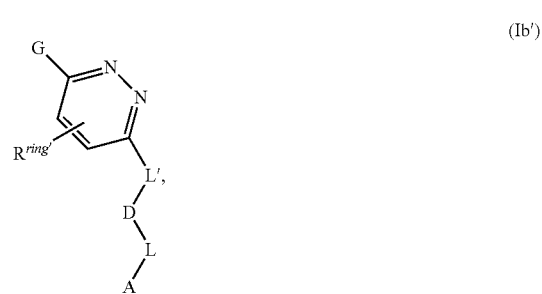

(Ib')

wherein $R^{ring'}$ is selected from H, —$C_1$-$C_4$-alkyl, -halogen, —$CF_3$, —$CBr_3$, —$CCl_3$; or —$C_5$-$C_{10}$-aryl optionally comprising one or more hetero atoms selected from N, O, S and optionally substituted by one or more substituents selected from halogen; or —$C_3$-$C_8$-cycloalkyl, —$C_1$-$C_4$-alkyl-$C_3$-$C_8$-cycloalkyl, —$C_1$-$C_4$-alkyl-$C_5$-$C_{10}$-aryl, —$C_1$-$C_4$-alkyl-$C_5$-$C_{10}$-heteroaryl, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (Ib) or (Ib'), wherein $R^{ring'}$ is selected from H, —$C_1$-$C_4$-alkyl, halogen, —$CF_3$, —$CCl_3$, —$CBr_3$; or —$C_3$-$C_8$-cycloalkyl, or —$C_5$-$C_{10}$-aryl, optionally comprising one or more hetero atoms selected from N, O, S, and optionally substituted with one or more substituents selected from halogen; or —$C_3$-$C_8$-cyclo alkyl, —$C_1$-$C_4$— alkyl-$C_5$-$C_{10}$-aryl, —$C_1$-$C_4$-alkyl-$C_5$-$C_{10}$-hetero aryl, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (Ib) or (Ib'), wherein $R^{ring'}$ is selected from —H, —$CH_3$, —$CF_3$, -cyclohexyl, -phenyl, -3,4-dichloro-phenyl, -naphthyl and -benzyl, optionally in form of their individual optical isomers, mixtures of their individual optical isomers, or racemates, as well as in form of their acid addition salts with pharmacologically acceptable acids, as well as in form of their solvates and/or hydrates, wherein A, L, D, L' and G are as defined hereinabove or hereinbelow.

In another preferred embodiment the present invention provides compounds according to formula (I), wherein Z' is nitrogen in case L' is a single bond, optionally in form of their individual optical isomers, mixtures of their individual optical isomers, or racemates, as well as in form of their acid addition salts with pharmacologically acceptable acids, as well as in form of their solvates and/or hydrates, wherein A, L, D, E and G are as defined hereinabove or hereinbelow.

In another preferred embodiment the present invention provides compounds according to formula (I), wherein Z' is carbon in case L' is not a single bond, optionally in form of their individual optical isomers, mixtures of their individual optical isomers, or racemates, as well as in form of their acid addition salts with pharmacologically acceptable acids, as well as in form of their solvates and/or hydrates, wherein A, L, D, E and G are as defined hereinabove or hereinbelow.

DEFINITIONS

Unless otherwise stated, all the substituents are independent of one another. If for example there might be a plurality of $C_{1-6}$-alkyl groups as substituents in one group, in the case of three substituents $C_{1-6}$-alkyl, one may represent methyl, one n-propyl and one tert-butyl.

Within the scope of this application, in the definition of possible substituents, these may also be represented in the form of a structural formula. An asterisk (*) in the structural formula of the substituent is to be understood as being the linking point to the rest of the molecule. Moreover, the atom of the substituent which follows the linking point is referred to as the atom in position number 1. Thus for example the groups piperidin-1-yl (I) and piperidin-4-yl (II) are shown as follows:

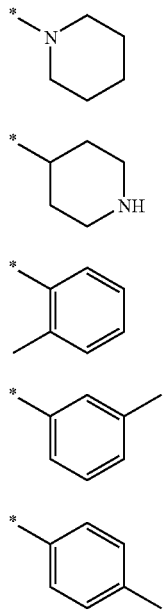

If there is no asterisk (*) in the structural formula of the substituent, each hydrogen atom may be removed at the substituent of each hydrogen atom and the valency thus freed may serve as a binding site to the rest of a molecule. Thus, for example, VI may represent 2-tolyl, 3-tolyl, 4-tolyl and benzyl.

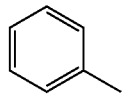

By the term "branched or unbranched, saturated or unsaturated $C_1$-$C_6$-carbon chain" it is meant a chain of carbon atoms, which is constituted by six carbon atoms arranged in a row and which can optionally further comprise branches or one or more hetero atoms selected from N, O or S. Said carbon chain can be saturated or unsaturated by comprising double or triple bonds.

By the term "$C_1$-$C_6$-alkyl" (including those which are part of other groups) are meant accordingly branched and unbranched alkyl groups with 1 to 6 carbon atoms. "$C_1$-$C_4$-alkyl" accordingly denotes branched and unbranched alkyl groups with 1 to 4 carbon atoms. Examples for alkyl groups with 1-6 carbon atoms include: methyl, ethyl, n-propyl, iso-propyl, n-butyl, iso-butyl, sec-butyl, tert-butyl, n-pentyl, iso-pentyl, neo-pentyl or hexyl. Optionally the abbreviations Me, Et, n-Pr, i-Pr, n-Bu, i-Bu, t-Bu, etc. may also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_1$-$C_8$-alkylene" (including those which are part of other groups) are meant branched and unbranched alkylene groups with 1 to 8 carbon atoms. By the term "$C_2$-$C_8$-alkylene" are meant branched and unbranched alkylene groups with 2 to 8 carbon atoms. By the term "$C_2$-$C_6$-alkylene" are meant branched and unbranched alkylene groups with 2 to 6 carbon atoms. By the term "$C_1$-$C_4$-alkylene" are meant branched and unbranched alkylene groups with 1 to 4 carbon atoms. By the term "$C_0$-$C_4$-alkylene" are meant branched and unbranched alkylene groups with 0 to 4 carbon atoms, thus also a single bond is encompassed. By the term "$C_1$-$C_3$-alkylene" are meant branched and unbranched alkylene groups with 1 to 3 carbon atoms. Examples for $C_1$-$C_8$-alkylene include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene, heptylene or octylene. Unless stated otherwise, the definitions propylene, butylene, pentylene, hexylene, heptylene and octylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

If the carbon chain is to be substituted by a group which together with one or two carbon atoms of the alkylene chain forms a carbocyclic ring with 3, 5 or 6 carbon atoms, this includes, inter alfa, the following examples of the rings:

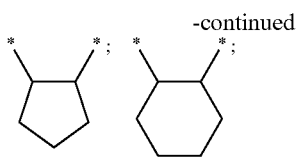

By the term "$C_2$-$C_6$-alkenyl" (including those which are part of other groups) are meant branched and unbranched alkenyl groups with 2 to 6 carbon atoms and by the term "$C_2$-$C_4$-alkenyl" are meant branched and unbranched alkenyl groups with 2 to 4 carbon atoms, provided that they have at least one double bond. Alkenyl groups with 2 to 4 carbon atoms are preferred. Examples for $C_2$-$C_6$-alkenyls include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_2$-$C_8$-alkenylene" (including those which are part of other groups) are meant branched and unbranched alkenylene groups with 2 to 8 carbon atoms and by the term "$C_2$-$C_6$-alkenylene" are meant branched and unbranched alkylene groups with 2 to 6 carbon atoms. Examples for $C_2$-$C_8$-alkenylenes include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene, heptenylene or octenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

By the term "$C_2$-$C_6$-alkynyl" (including those which are part of other groups) are meant branched and unbranched alkynyl groups with 2 to 6 carbon atoms and by the term "$C_2$-$C_4$-alkynyl" are meant branched and unbranched alkynyl groups with 2 to 4 carbon atoms, provided that they have at least one triple bond. Examples for $C_2$-$C_6$-alkynyls include: ethynyl, propynyl, butynyl, pentynyl or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1,2- and 3-butynyl, 1-methyl-1-propynyl, 1-methyl-2-propynyl etc.

By the term "$C_2$-$C_8$-alkynylene" (including those which are part of other groups) are meant branched and unbranched alkynylene groups with 2 to 8 carbon atoms and by the term "$C_2$-$C_6$-alkynylene" are meant branched and unbranched alkylene groups with 2 to 6 carbon atoms. Examples of $C_2$-$C_8$-alkynylenes include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene, heptynylene or octynylene. Unless stated otherwise, the definitions propynylene, butynylene, pentynylene and hexynylene include all the possible isomeric forms of the groups in question with the same number of carbons. Thus for example propynyl also includes 1-methylethynylene and butynylene includes 1-methylpropynylene, 1,1-dimethylethynylene, 1,2-dimethylethynylene.

By the term "ring" are meant carbon rings, which can be saturated, unsaturated or aromatic and which optionally can comprise one or more hetero atoms selected from N, O or S.

By the term "heterocycle" are meant carbon rings, which can be saturated, unsaturated or aromatic and which comprise one or more hetero atoms selected from N, O or S.

By the term "$C_3$-$C_8$-cycloalkyl" (including those which are part of other groups) are meant saturated carbon ring systems with 3 to 8 carbon atoms. Likewise, by the term "$C_3$-$C_6$-cycloalkyl" are meant saturated carbon ring systems with 3 to 6 carbon atoms. Examples of $C_3$-$C_8$-cycloalkyls include: cyclopropyl, cyclobutyl, cyclopentyl, cyclohexyl, cycloheptyl or cyclooctyl.

By the term "$C_5$-$C_{10}$-aryl" (including those which are part of other groups) are meant aromatic ring systems with 5 to 10 carbon atoms. Examples include: phenyl or naphthyl. Unless otherwise stated, the aromatic ring systems may be substituted by one or more groups selected from among methyl, ethyl, iso-propyl, tert-butyl, hydroxy, fluorine, chlorine, bromine and iodine.

By the term "$C_5$-$C_{10}$-heteroaryl" (including those which are part of other groups) are meant aromatic ring systems with 5 to 10 carbon atoms and further comprising 1 to 3 hetero atoms selected from N, O and S. Examples include: pyridinyl or quinolinyl. Unless otherwise stated, the aromatic ring systems may be substituted by one or more groups selected from among methyl, ethyl, iso-propyl, tert-butyl, hydroxy, fluorine, chlorine, bromine and iodine.

When a generic combined groups are used, for example —X—$C_1$-$C_4$-alkyl- with X being a functional group such as —CO—, —NH—, —C(OH)— and the like, the functional group X can be located at either of the ends of the —$C_1$-$C_4$-alkyl chain.

"Halogen" within the scope of the present invention denotes fluorine, chlorine, bromine or iodine. Unless stated to the contrary, fluorine, chlorine and bromine are regarded as preferred halogens.

The above listed groups and residues can be combined to form more complex structures composed from carbon chains and rings or the like.

Compounds of general formula 1 may have acid groups, chiefly carboxyl groups, and/or basic groups such as e.g. amino functions. Compounds of general formula 1 may therefore occur as internal salts, as salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically useable bases such as alkali or alklaline earth metal hydroxides or carbonates, zinc or ammonium hydroxides or organic amines such as e.g. diethylamine, triethylamine, triethanolamine inter alfa.

As mentioned hereinbefore, the compounds of formula 1 may be converted into the salts thereof, particularly for pharmaceutical use, into the physiologically and pharmacologically acceptable salts thereof. These salts may on the one hand be in the form of the physiologically and pharmacologically acceptable acid addition salts of the compounds of formula 1 with inorganic or organic acids. On the other hand, if R is hydrogen, the compound of formula 1 may also be converted by reaction with inorganic bases into physiologically and pharmacologically acceptable salts with alkali or alkaline earth metal cations as counter ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. The alkali and alkaline earth metal salts of the compound of formula 1 are preferably prepared using the alkali and alkaline earth metal hydroxides and hydrides thereof, of which the hydroxides and hydrides of the alkaline earth metals, particularly of sodium and potassium, are preferred and sodium and potassium hydroxide are particularly preferred.

If desired, the compounds of general formula (1) may be converted into the salts thereof, particularly, for pharmaceutical use, into the pharmacologically acceptable acid addition salts with an inorganic or organic acid. Suitable acids include for example succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid.

The compounds according to the invention may optionally occur as racemates, but they may also be obtained as pure enantiomers, i.e. in the (R) or (S) form. Preferred compounds are those which occur as racemates or as the (S) form.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid.

EXAMPLES

The following examples illustrate structures according to Formula (I) according to the present invention:

| Ex. # | structure | Synthetic route | Characterization (ESI-MS) |
|---|---|---|---|
| 1 | Br-phenyl-pyrazole-piperazine-N-CH$_3$ | A1 | m/z(+) 321/323 (M + H$^+$) |
| 2 | 3,4-diCl-phenyl-pyrazole-piperidine-piperidine | A1 | m/z(+) 379/381/383 (M + H$^+$) |
| 3 | 3,4-diCl-phenyl-pyrazole-piperazine-N-CH$_3$ | A1 | m/z(+) 311/313/315 (M + H$^+$) |
| 4 | 3,4-diCl-phenyl-pyrazole-piperazine-CH$_2$-morpholine-N-CH(CH$_3$)$_2$ | A1 | m/z(+) 438/440/442 (M + H$^+$) |

-continued

| Ex. # | structure | Synthetic route | Characterization (ESI-MS) |
|---|---|---|---|
| 5 | 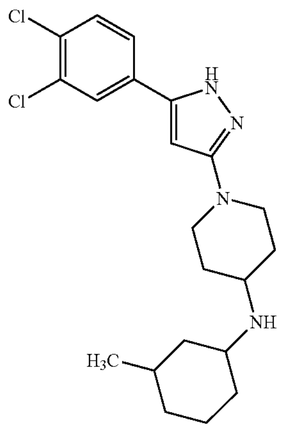 [SMILES: CC1CCCC(NC2CCN(c3cc(-c4ccc(Cl)c(Cl)c4)[nH]n3)CC2)C1] | A2 | m/z(+) 407/409/411 (M + H$^+$) |
| 6 | 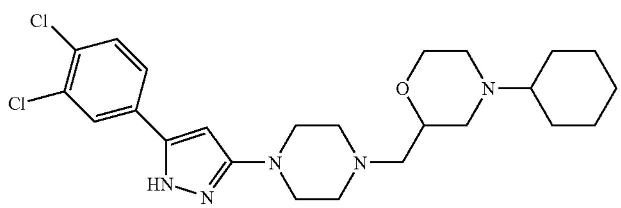 [SMILES: Clc1ccc(-c2cc(N3CCN(CC4CN(C5CCCCC5)CCO4)CC3)n[nH]2)cc1Cl] | A1 | m/z(+) 478/480/482 (M + H$^+$) |
| 7 | 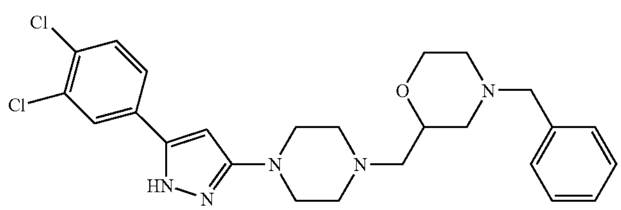 [SMILES: Clc1ccc(-c2cc(N3CCN(CC4CN(Cc5ccccc5)CCO4)CC3)n[nH]2)cc1Cl] | A1 | m/z(+) 486/488/490 (M + H) |
| 8 | 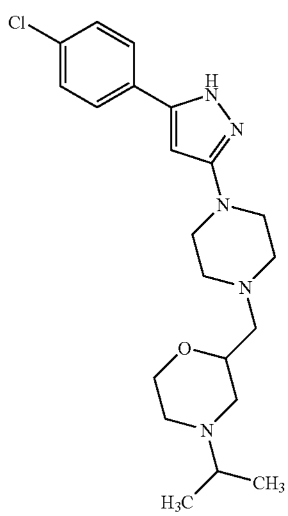 [SMILES: CC(C)N1CCOC(CN2CCN(c3cc(-c4ccc(Cl)cc4)[nH]n3)CC2)C1] | A1 | m/z(+) 404/406 (M + H) |

-continued
| Ex. # | structure | Synthetic route | Characterization (ESI-MS) |
|---|---|---|---|
| 9 | 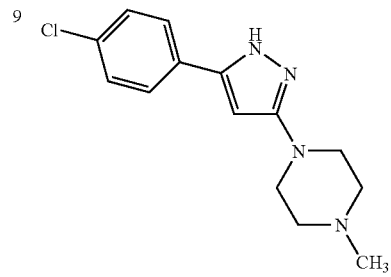 | A1 | m/z(+) 277/279 (M + H⁺) |
| 10 | 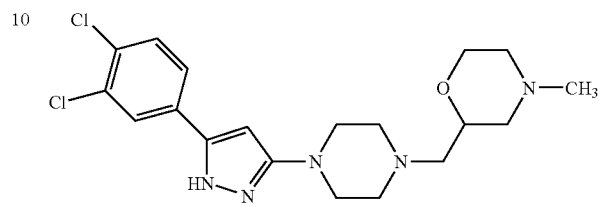 | A1 | m/z(+) 410/412/414 (M + H⁺) |
| 11 | 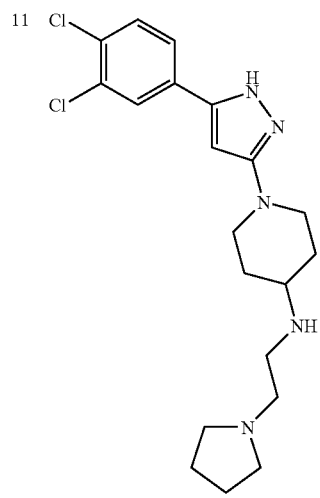 | A2 | m/z(+) 408/410/412 (M + H⁺) |
| 12 | 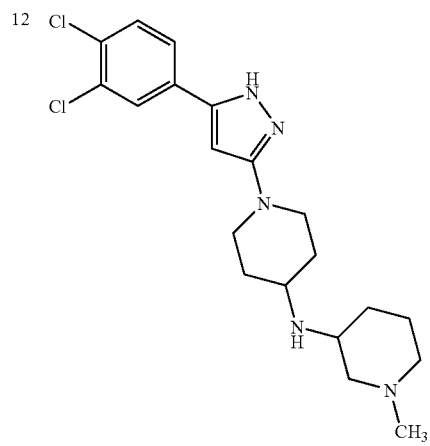 | A2 | m/z(+) 408/410/412 (M + H⁺) |

-continued
| Ex. # | structure | Synthetic route | Characterization (ESI-MS) |
|---|---|---|---|
| 13 | 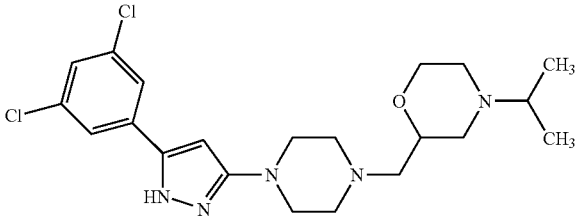 [SMILES: CC(C)N1CCOC(CN2CCN(c3cc(-c4cc(Cl)cc(Cl)c4)[nH]n3)CC2)C1] | A1 | m/z(+) 438/440/442 (M + H⁺) |
| 14 | 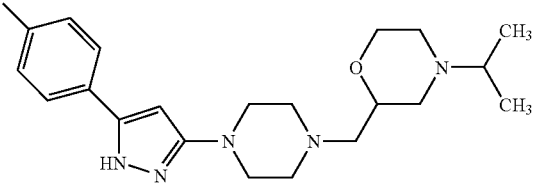 | A1 | m/z(+) 448/450 (M + H⁺) |
| 15 | 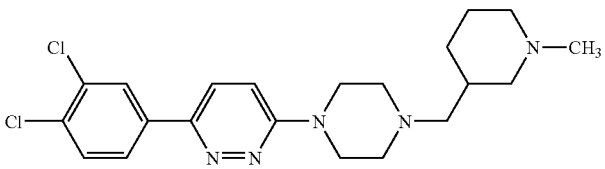 [SMILES: CN1CCCC(CN2CCN(c3ccc(-c4ccc(Cl)c(Cl)c4)nn3)CC2)C1] | B1 | m/z(+) 420/422/424 (M + H⁺) |
| 16 | 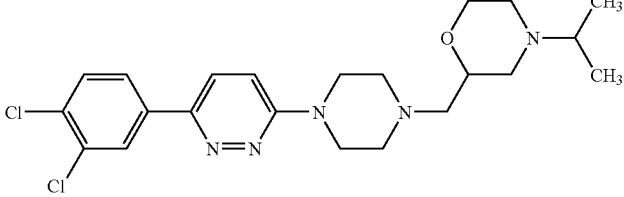 | B1 | m/z(+) 450/452/454 (M + H⁺) |
| 17 | 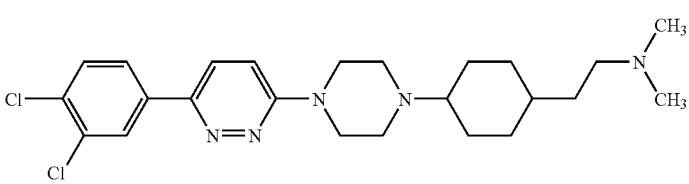 [SMILES: CN(C)CCC1CCC(N2CCN(c3ccc(-c4ccc(Cl)c(Cl)c4)nn3)CC2)CC1] | B1 | m/z(+) 462/464/466 (M + H⁺) |
| 18 | 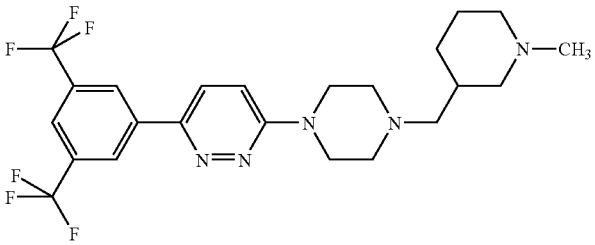 [SMILES: CN1CCCC(CN2CCN(c3ccc(-c4cc(C(F)(F)F)cc(C(F)(F)F)c4)nn3)CC2)C1] | B1 | m/z(+) 488 (M + H⁺) |
| 19 | 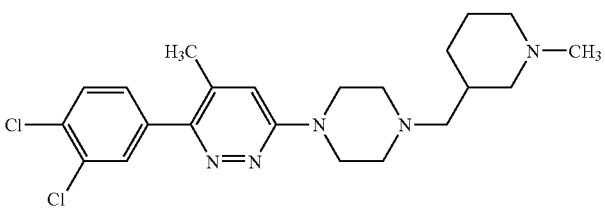 [SMILES: Cc1cc(N2CCN(CC3CCCN(C)C3)CC2)nnc1-c1ccc(Cl)c(Cl)c1] | B1 | m/z(+) 434/436/438 (M + H⁺) |

-continued

| Ex. # | structure | Synthetic route | Characterization (ESI-MS) |
|---|---|---|---|
| 20 | 3,5-dichlorophenyl-pyridazine-piperazine-CH2-(1-methylpiperidin-3-yl) | B1 | m/z(+) 420/422/424 (M + H+) |
| 21 | 3,4-dichlorophenyl-(4-methyl)pyridazine-piperazine-CH2-(4-isopropylmorpholin-2-yl) | B1 | m/z(+) 464/466/468 (M + H+) |
| 22 | 3-(trifluoromethyl)phenyl-pyridazine-piperazine-CH2-(1-methylpiperidin-3-yl) | B1 | m/z(+) 420 (M + H+) |
| 23 | 3,4-dichlorophenyl-pyridazine-piperidine-C(O)NH-(CH2)3-morpholine | B1 | m/z(+) 478/480/482 (M + H+) |
| 24 | 3,4-dichlorophenyl-pyridazine-piperazine-CH2CH2-(1-methylpiperidin-2-yl) | B1 | m/z(+) 434/436/438 (M + H) |
| 25 | 3,4-dichlorophenyl-pyridazine-piperazine-CH2CH2-pyrrolidine | B1 | m/z(+) 406/408/410 (M + H+) |
| 26 | 3,4-dichlorophenyl-pyridazine-piperazine-CH2CH2-morpholine | B1 | m/z(+) 422/424/426 (M + H+) |

-continued
| Ex. # | structure | Synthetic route | Characterization (ESI-MS) |
|---|---|---|---|
| 27 | 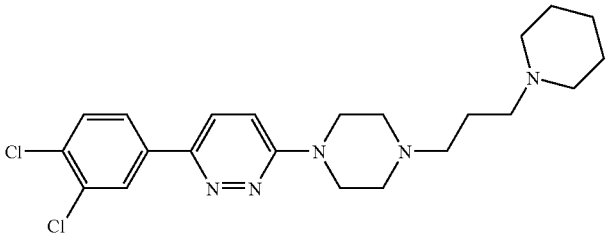 [SMILES: Clc1ccc(-c2ccc(N3CCN(CCCN4CCCCC4)CC3)nn2)cc1Cl] | B1 | m/z(+) 434/436/438 (M + H⁺) |
| 28 | 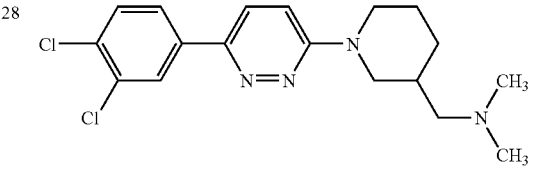 | B1 | m/z(+) 365/367/369 (M + H) |
| 29 | 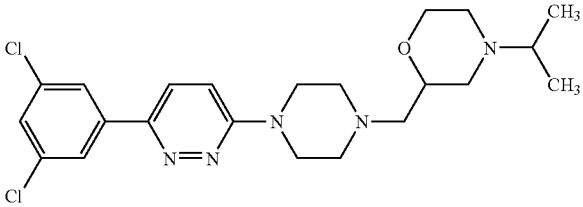 [SMILES: CC(C)N1CCOC(CN2CCN(c3ccc(-c4cc(Cl)cc(Cl)c4)nn3)CC2)C1] | B1 | m/z(+) 450/452/454 (M + H) |
| 30 | 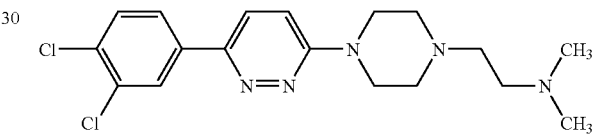 | B1 | m/z(+) 380/382/384 (M + H⁺) |
| 31 | 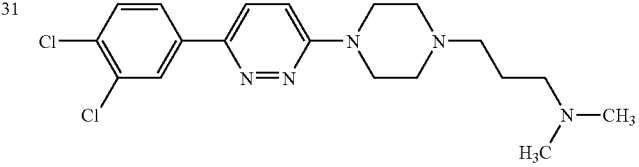 | B1 | m/z(+) 394/396/368 (M + H⁺) |
| 32 | 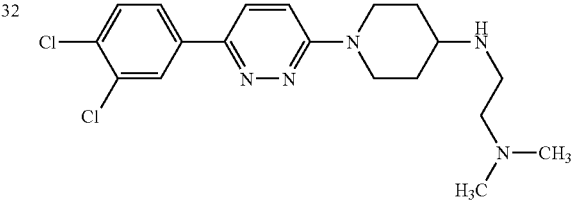 | B2 | m/z(+) 394/396/398 (M + H⁺) |
| 33 | 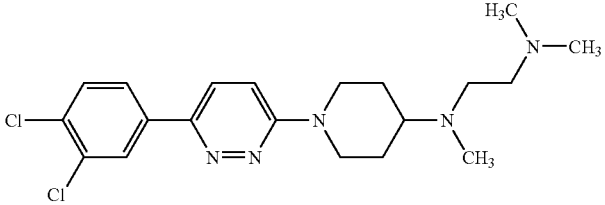 [SMILES: CN(C)CCN(C)C1CCN(c2ccc(-c3ccc(Cl)c(Cl)c3)nn2)CC1] | B2 | m/z(+) 408/410/412 (M + H⁺) |

-continued
| Ex. # | structure | | Synthetic route | Characterization (ESI-MS) |
|---|---|---|---|---|
| 34 | 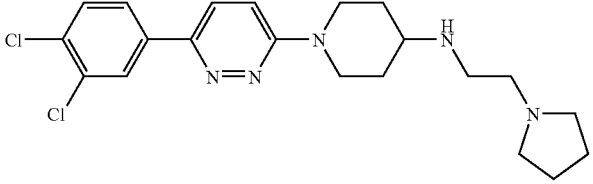 [SMILES: Clc1ccc(-c2ccc(N3CCC(NCCN4CCCC4)CC3)nn2)cc1Cl] | | B1 | m/z(+) 420/422/424 (M + H+) |
| 35 | 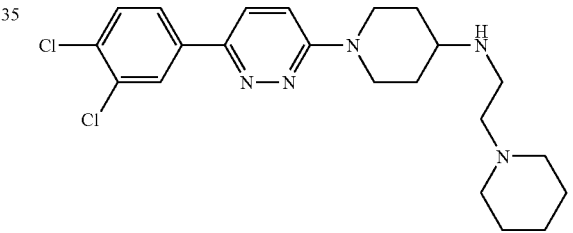 | | B2 | m/z(+) 434/436/438 (M + H+) |
| 36 | 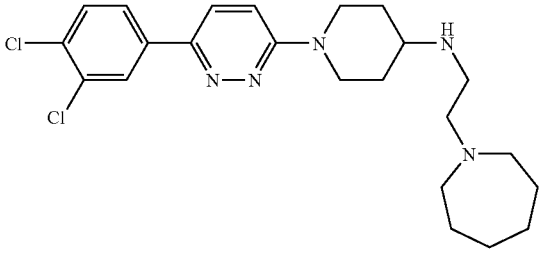 [SMILES: Clc1ccc(-c2ccc(N3CCC(NCCN4CCCCCC4)CC3)nn2)cc1Cl] | | B2 | m/z(+) 448/450/452 (M + H+) |
| 37 | 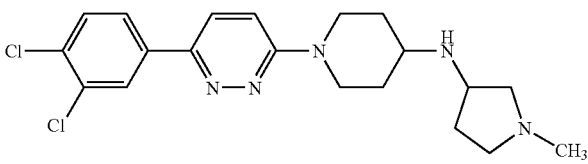 [SMILES: CN1CCC(NC2CCN(c3ccc(-c4ccc(Cl)c(Cl)c4)nn3)CC2)C1] | | B2 | m/z(+) 406/408/410 (M + H+) |
| 38 | 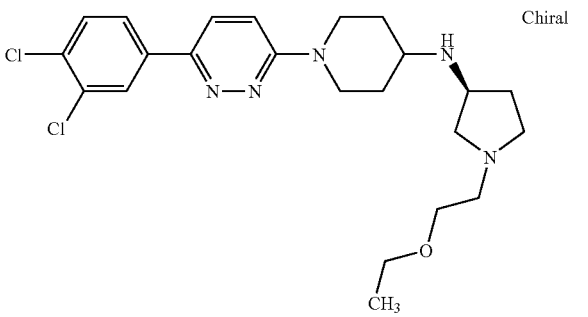 [SMILES: CCOCCN1CC[C@H](NC2CCN(c3ccc(-c4ccc(Cl)c(Cl)c4)nn3)CC2)C1] | Chiral | B2 | m/z(+) 464/466/468 (M + H+) |
| 39 | 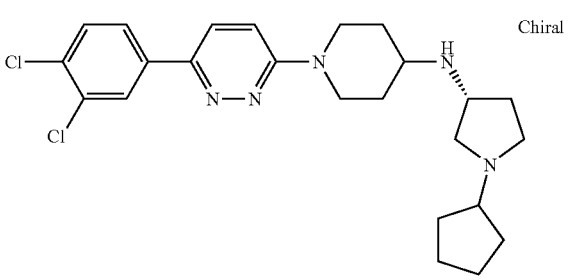 [SMILES: Clc1ccc(-c2ccc(N3CCC(N[C@@H]4CCN(C5CCCC5)C4)CC3)nn2)cc1Cl] | Chiral | B2 | m/z(+) 460/462/464 (M + H+) |

-continued
| Ex. # | structure | Synthetic route | Characterization (ESI-MS) |
|---|---|---|---|
| 40 | 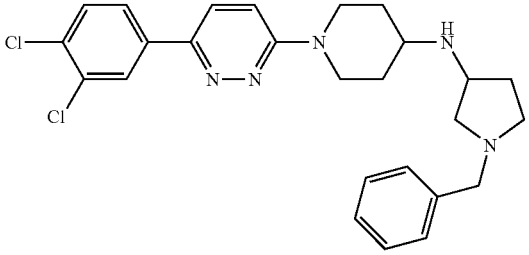 [SMILES: Clc1ccc(-c2ccc(N3CCC(NC4CCN(Cc5ccccc5)C4)CC3)nn2)cc1Cl] | B2 | m/z(+) 482/484/486 (M + H⁺) |
| 41 | 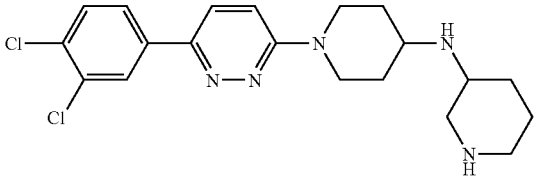 [SMILES: Clc1ccc(-c2ccc(N3CCC(NC4CCCNC4)CC3)nn2)cc1Cl] | B2 | m/z(+) 406/408/410 (M + H⁺) |
| 42 | 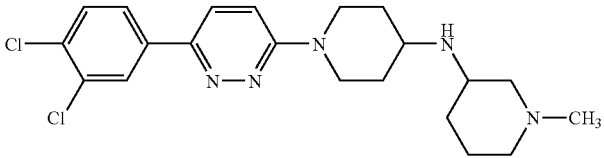 [SMILES: CN1CCCC(NC2CCN(c3ccc(-c4ccc(Cl)c(Cl)c4)nn3)CC2)C1] | B2 | m/z(+) 420/422/424 (M + H⁺) |
| 43 | 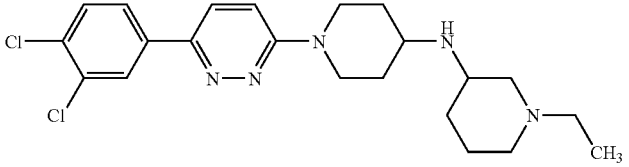 [SMILES: CCN1CCCC(NC2CCN(c3ccc(-c4ccc(Cl)c(Cl)c4)nn3)CC2)C1] | B2 | m/z(+) 434/436/438 (M + H⁺) |
| 44 | 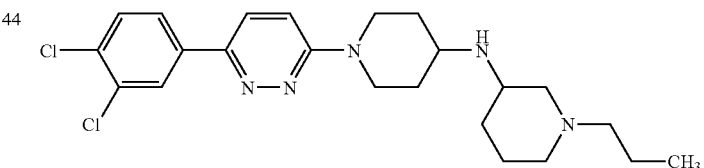 | B2 | m/z(+) 448/450/452 (M + H⁺) |
| 45 | 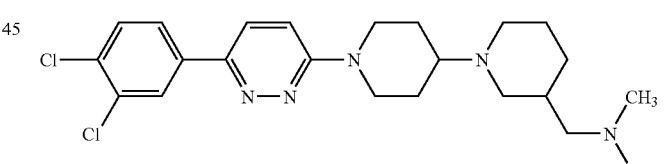 | B2 | m/z(+) 448/450/452 (M + H⁺) |
| 46 | 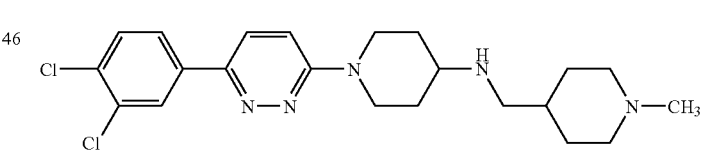 | B2 | m/z(+) 434/436/438 (M + H⁺) |
| 47 | 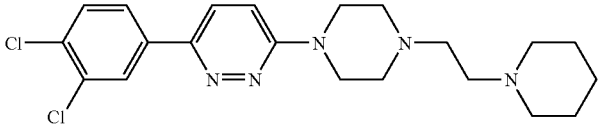 [SMILES: Clc1ccc(-c2ccc(N3CCN(CCN4CCCCC4)CC3)nn2)cc1Cl] | B1 | m/z(+) 420/422/424 (M + H⁺) |

| Ex. # | structure | Synthetic route | Characterization (ESI-MS) |
|---|---|---|---|
| 48 | (3,4-dichlorophenyl)-pyridazine-piperazine-CH₂CH₂CH₂-N(CH₂CH₃)₂ | B1 | m/z(+) 422/424/426 (M + H⁺) |
| 49 | (3-fluoro-5-trifluoromethylphenyl)-pyridazine-piperazine-CH₂-(1-methylpiperidin-3-yl) | B1 | m/z(+) 438 (M + H⁺), 219 (0.5 * M + H⁺) |
| 50 | (3,4-dichlorophenyl)-pyridazine-piperazine-(3-dimethylaminocyclohexyl) | B1 | m/z(+) 434/436/438 (M + H⁺) |
| 51 | (3,4-dichlorophenyl)-pyridazine-piperazine-(4-dimethylaminomethylcyclohexyl) | B1 | m/z(+) 448/450/452 (M + H⁺) |
| 52 | (3,4-dichlorophenyl)-pyridazine-[1,4]diazepane-(1-methylpiperidin-3-yl) | B1 | m/z(+) 420/422/424 (M + H⁺) |
| 53 | (3,4-dichlorophenyl)-pyridazine-NH-(1-methylpiperidin-4-yl) | B1 | m/z(+) 337/339/341 (M + H⁺) |
| 54 | (3,4-dichlorophenyl)-pyridazine-NH-(4-dimethylaminocyclohexyl) | B1 | m/z(+) 365/367/369 (M + H⁺), 183/184 (0.5 * M + H⁺) |

-continued

| Ex. # | structure | Synthetic route | Characterization (ESI-MS) |
|---|---|---|---|
| 55 | 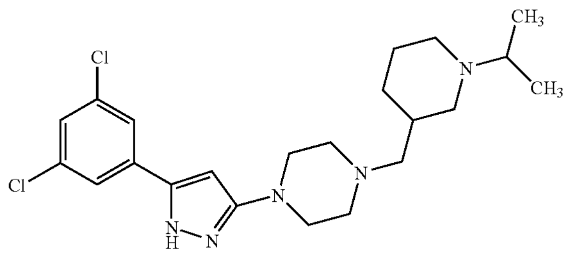 [SMILES: CC(C)N1CCCC(CN2CCN(c3cc(-c4cc(Cl)cc(Cl)c4)[nH]n3)CC2)C1] | A1 | m/z(+) 436/38/40 (2 Cl) |
| 56 | 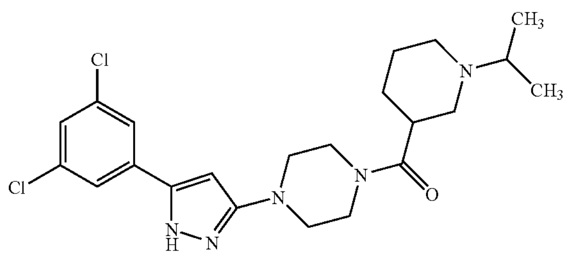 [SMILES: CC(C)N1CCCC(C(=O)N2CCN(c3cc(-c4cc(Cl)cc(Cl)c4)[nH]n3)CC2)C1] | A1 | m/z(+) 450/52/54 (2 Cl) |
| 57 | 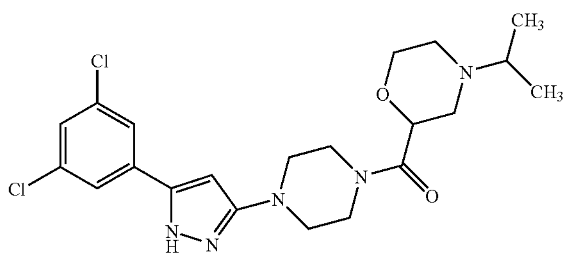 | A1 | m/z(+) 452/54/56 (2 Cl) |
| 58 | 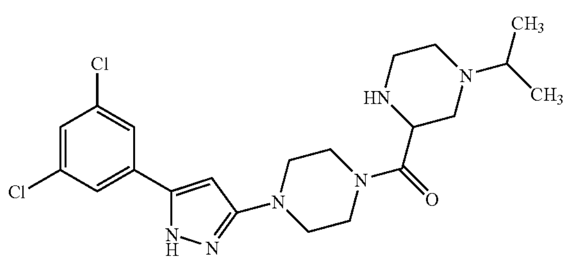 | A1 | m/z(+) 451/53/55 (2 Cl) |
| 59 | 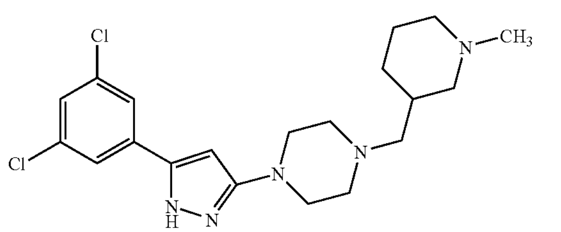 [SMILES: CN1CCCC(CN2CCN(c3cc(-c4cc(Cl)cc(Cl)c4)[nH]n3)CC2)C1] | A1 | m/z(+) 408/10/12 (2 Cl) |
| 60 | 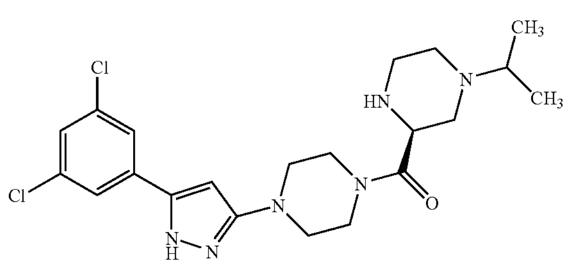 [SMILES: CC(C)N1CCN[C@H](C(=O)N2CCN(c3cc(-c4cc(Cl)cc(Cl)c4)[nH]n3)CC2)C1] | A1 | m/z(+) 451/53/55 (2 Cl) |

-continued

| Ex. # | structure | Synthetic route | Characterization (ESI-MS) |
|---|---|---|---|
| 61 | 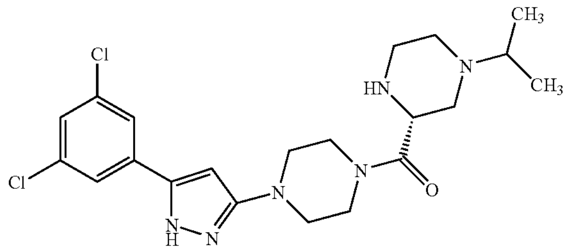 [SMILES: CC(C)N1CCN[C@@H](C(=O)N2CCN(c3cc(-c4cc(Cl)cc(Cl)c4)[nH]n3)CC2)C1] | A1 | m/z(+) 451/53/55 (2 Cl) |
| 62 | 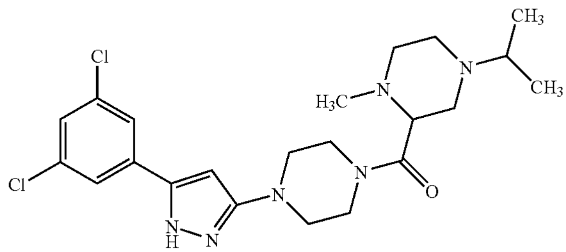 [SMILES: CC(C)N1CCN(C)C(C(=O)N2CCN(c3cc(-c4cc(Cl)cc(Cl)c4)[nH]n3)CC2)C1] | A1 | m/z(+) 465/67/69 (2 Cl) |
| 63 | 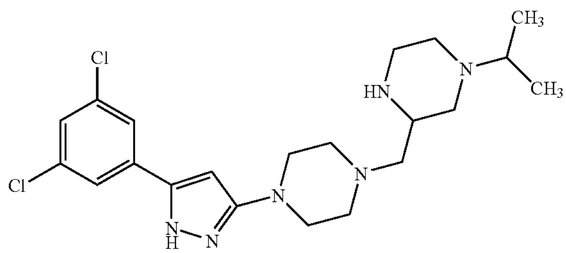 [SMILES: CC(C)N1CCNC(CN2CCN(c3cc(-c4cc(Cl)cc(Cl)c4)[nH]n3)CC2)C1] | A1 | m/z(+) 437/39/41 (2 Cl) |
| 64 | 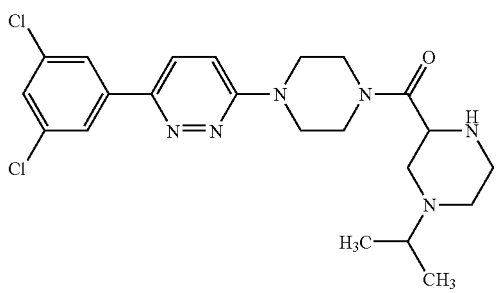 [SMILES: CC(C)N1CCNC(C(=O)N2CCN(c3ccc(-c4cc(Cl)cc(Cl)c4)nn3)CC2)C1] | B1 | m/z(+) 463/65/67 (2 Cl) |
| 65 | 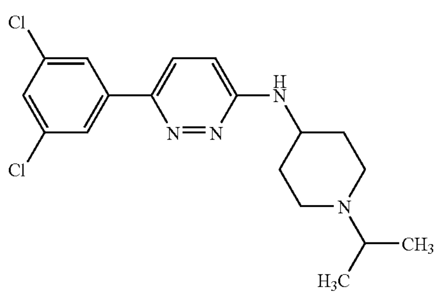 [SMILES: CC(C)N1CCC(Nc2ccc(-c3cc(Cl)cc(Cl)c3)nn2)CC1] | B1 | m/z(+) 365/67/69 (2 Cl) |
| 66 | 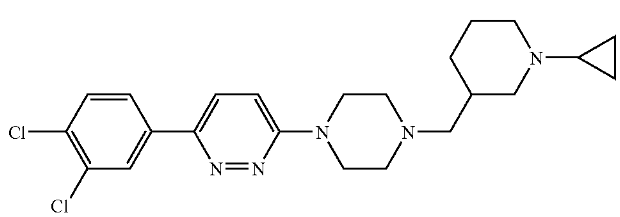 [SMILES: Clc1ccc(-c2ccc(N3CCN(CC4CCCN(C5CC5)C4)CC3)nn2)cc1Cl] | B1 | m/z(+) 446/48/50 (2 Cl) |

-continued

| Ex. # | structure | Synthetic route | Characterization (ESI-MS) |
|---|---|---|---|
| 67 | [4-isopropylphenyl-pyridazine-piperazine-(N-methylpiperidin-3-yl)methyl] | B1 | m/z(+) 394 |
| 68 | [2,3-dichlorophenyl-pyridazine-piperazine-(N-methylpiperidin-3-yl)methyl] | B1 | m/z(+) 420/22/24 (2 Cl) |
| 69 | [2,5-dichlorophenyl-pyridazine-piperazine-(N-methylpiperidin-3-yl)methyl] | B1 | m/z(+) 420/22/24 (2 Cl) |
| 70 | [2,3-dimethylphenyl-pyridazine-piperazine-(N-methylpiperidin-3-yl)methyl] | B1 | m/z(+) 380.6 |
| 71 | [2,5-dimethylphenyl-pyridazine-piperazine-(N-methylpiperidin-3-yl)methyl] | B1 | m/z(+) 380.6 |
| 72 | [3-isopropylphenyl-pyridazine-piperazine-(N-methylpiperidin-3-yl)methyl] | B1 | m/z(+) 394 |
| 73 | [3,4-dimethylphenyl-pyridazine-piperazine-(N-methylpiperidin-3-yl)methyl] | B1 | m/z(+) 380 |

-continued
| Ex. # | structure | Synthetic route | Characterization (ESI-MS) |
|---|---|---|---|
| 74 | 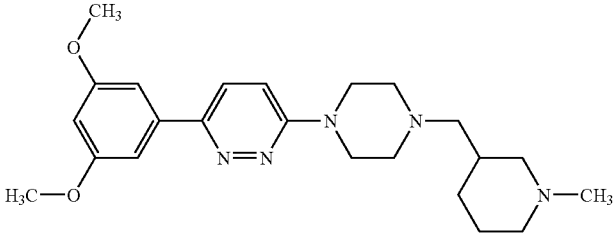 | B1 | m/z(+) 412.3 |
| 75 | 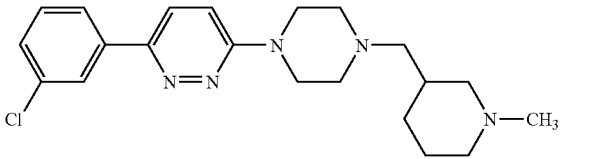 [SMILES: CN1CCCC(CN2CCN(c3ccc(-c4cccc(Cl)c4)nn3)CC2)C1] | B1 | m/z(+) 386/88 (Cl) |
| 76 | 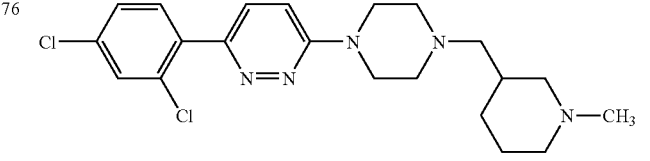 | B1 | m/z(+) 420/22/24 (2Cl) |
| 77 | 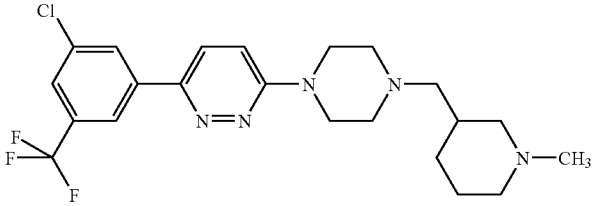 [SMILES: CN1CCCC(CN2CCN(c3ccc(-c4cc(Cl)cc(C(F)(F)F)c4)nn3)CC2)C1] | B1 | m/z(+) 454/56 (Cl) |
| 78 | 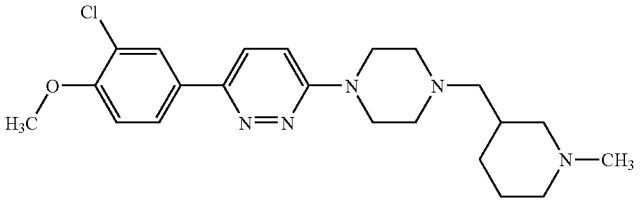 | B1 | m/z(+) 416/18 (Cl) |
| 79 | 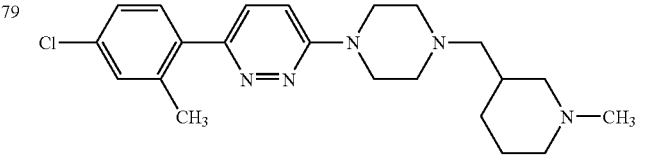 | B1 | m/z(+) 400/02 (Cl) |
| 80 | 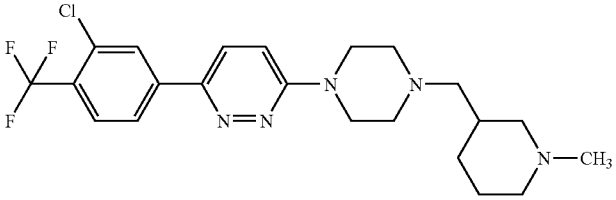 [SMILES: CN1CCCC(CN2CCN(c3ccc(-c4ccc(C(F)(F)F)c(Cl)c4)nn3)CC2)C1] | B1 | m/z(+) 454/56 (Cl) |

-continued
| Ex. # | structure | Synthetic route | Characterization (ESI-MS) |
|---|---|---|---|
| 81 | 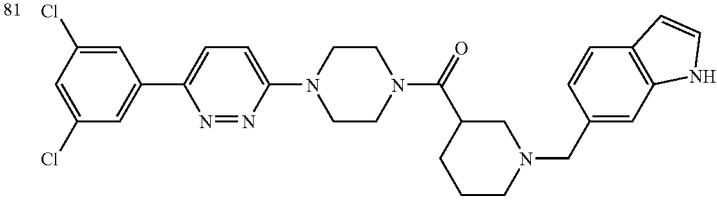 | B1 | m/z(+) 549/51/53 (2Cl) |
| 82 | 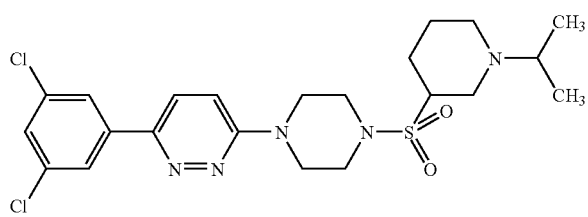 [SMILES: CC(C)N1CCCC(S(=O)(=O)N2CCN(c3ccc(-c4cc(Cl)cc(Cl)c4)nn3)CC2)C1] | B1 | m/z(+) 498/500/02 (2Cl) |
| 83 | 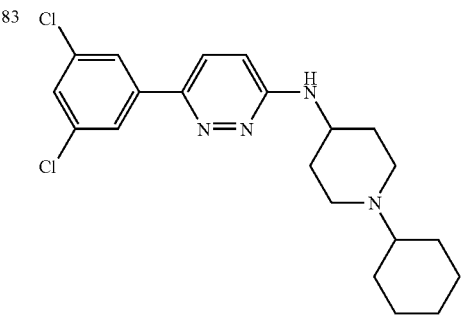 | B1 | m/z(+) 405/07/09 (2Cl) |
| 84 | 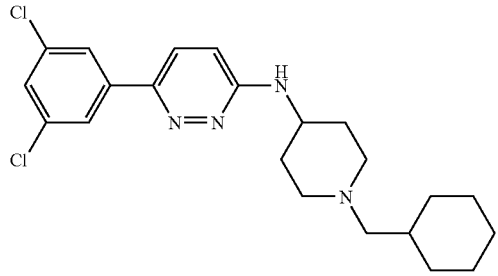 [SMILES: Clc1cc(Cl)cc(-c2ccc(NC3CCN(CC4CCCCC4)CC3)nn2)c1] | B1 | m/z(+) 419/21/23 (2Cl) |
| 85 | 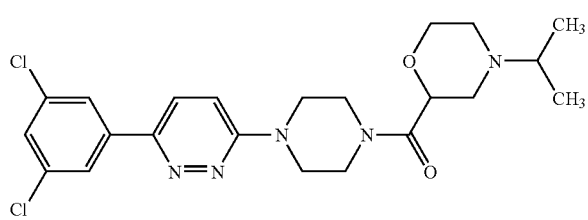 [SMILES: CC(C)N1CCOC(C(=O)N2CCN(c3ccc(-c4cc(Cl)cc(Cl)c4)nn3)CC2)C1] | B1 | m/z(+) 464/66/68 (2Cl) |
| 86 | 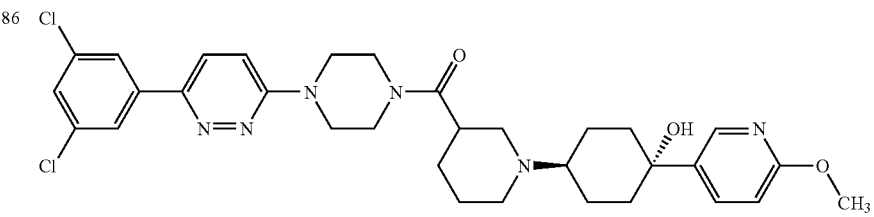 | B1 | m/z(+) 625/27/29 (2Cl) |

-continued

| Ex. # | structure | Synthetic route | Characterization (ESI-MS) |
|---|---|---|---|
| 87 | 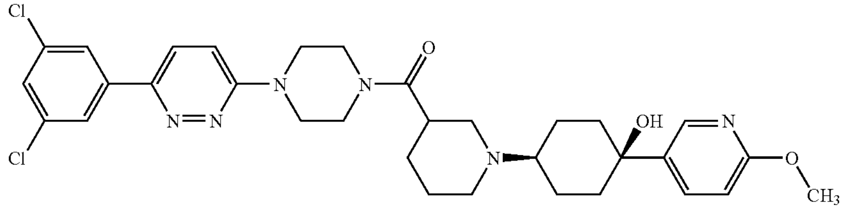 [SMILES: COc1ccc([C@]2(O)CC[C@H](N3CCCC(C(=O)N4CCN(c5ccc(-c6cc(Cl)cc(Cl)c6)nn5)CC4)C3)CC2)cn1] | B1 | m/z(+) 625/27/29 (2Cl) |
| 88 | 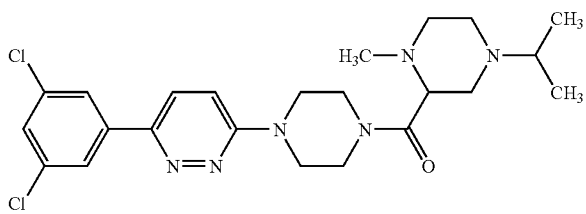 [SMILES: CC(C)N1CCN(C)C(C(=O)N2CCN(c3ccc(-c4cc(Cl)cc(Cl)c4)nn3)CC2)C1] | B1 | m/z(+) 477/79/81 (2Cl) |
| 89 | 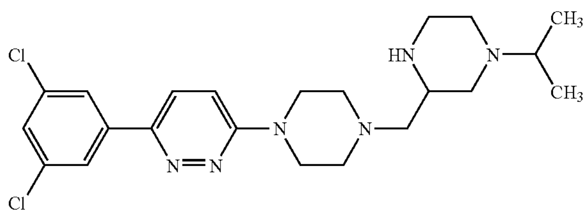 [SMILES: CC(C)N1CCNC(CN2CCN(c3ccc(-c4cc(Cl)cc(Cl)c4)nn3)CC2)C1] | B1 | m/z(+) 449/51/53 (2Cl) |
| 90 | 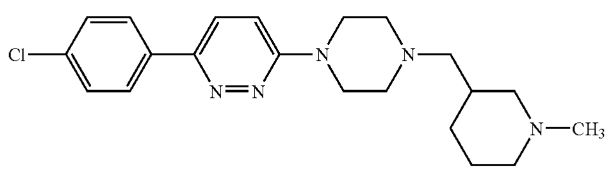 | B1 | m/z(+) 386.4 |
| 91 | 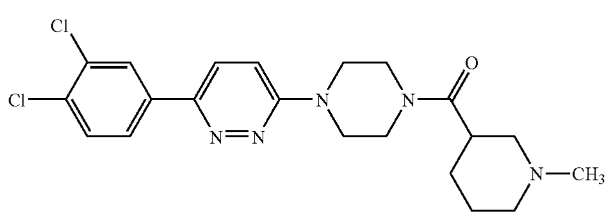 [SMILES: CN1CCCC(C(=O)N2CCN(c3ccc(-c4ccc(Cl)c(Cl)c4)nn3)CC2)C1] | B1 | |
| 92 | 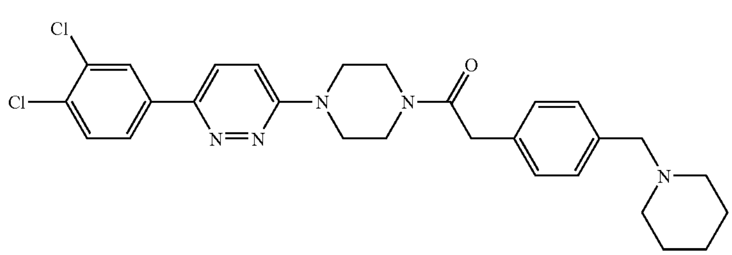 [SMILES: O=C(Cc1ccc(CN2CCCCC2)cc1)N1CCN(c2ccc(-c3ccc(Cl)c(Cl)c3)nn2)CC1] | B1 | |
| 93 | 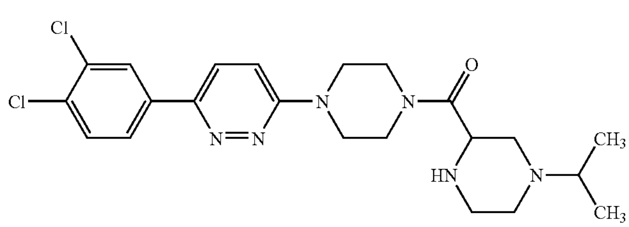 [SMILES: CC(C)N1CCNC(C(=O)N2CCN(c3ccc(-c4ccc(Cl)c(Cl)c4)nn3)CC2)C1] | B1 | |

In some instances the above table lists individual enantiomers as examples. This does not mean that the other enantiomer(s) are excluded from the scope of the present invention.

Therapeutic Applications

The above exemplary substances have been tested for binding to CCR2 using a binding assay as outlined herein below:

Cell culture:

THP-1 cells (human acute monocytic leukaemia cells) were cultured under standardized conditions at 37° C. and 5% CO2 in a humidified incubator. THP-1 cells were cultivated in RPMI 1640 medium (Gibco 21875) containing 1% MEM-NEAA (Gibso 11140) 2 mM L-glutamine, 1.5 g/L sodium bicarbonate, 4.5 g/L glucose, 10 mM HEPES and 1.0 mM sodium pyruvate, 90%; 10% fetal calf serum (FCS Gibco 10500-064).

Membranes were prepared from THP-1 cells. THP-1 cells were centrifuged at 300×g at 4° C. for 10 mM. The cell pellet was resuspendet in Phosphate Buffer Saline (PBS, including 10 µM Pefabloc and a protease inhibitor mix 'complete', Boehringer Mannheim (1 tablet/50 ml)), to a concentration of 80 cells/ ml. The membrane preparation was performed by disrupting the cells by nitrogen decomposition (at 50 bar, for 1 h) in a "Nitrogen Bombe" (Parr Instrument). Cell debris was removed by centrifugation (800×g at 4° C., 1 mM). The supernatant was centrifuged at 80000×g, 4° C. for 30 mM to sediment the cell membranes. Usually 50 mg of protein (Bradford assay) were yielded from 1×10E9 cells. The membranes were resuspendet in 25 mM HEPES, 25 mM MgCl$_2$, 1 mM CaCl$_2$, 10% Glycerine for storage in aliquots at –80° C. in 25 mM HEPES, 25 mM MgCl$_2$, 1 mM CaCl$_2$, 10% Glycerine and stored at –80° C.

Receptor membrane binding assay:

Perkin Elmer NEX 332 Jod 125 MCP-1, Stock: 2200 Ci/mmol solved in 2000 µl assay buffer, stored at –20° C. THP-1 membrane were adjusted with 25 mM HEPES, pH 7.2; 5 mM MgCl2; 0.5 mM CaCl$_2$; 0.2% BSA assay buffer to a concentration of 2.5 µg/15 µl. Amersham Biosciences PVT-WGA Beads (RPNQ0001) were adjusted with assay buffer to a concentration of 0.24 mg/30 µl. For preparation of the membrane-bead-suspension membranes and beads were incubated for 30 mM at RT under rotation (60 rpm) with a ratio of 1:2. Test compounds dissolved in 100% DMSO to a concentration of 10 mM and are further diluted with 100% DMSO to 1 mM. All additional compound dilutions were obtained with assay buffer, final 1% DMSO. Compounds, membrane-bead-suspension and [125I]MCP-1 (ca. 25000 cpm/10 µl) were incubated. Bound radioactivity was determined by scintillation counter after 8 h. Determination of affinity of test compounds (dissociation constant Ki) is calculated by iterative fitting of experimental data using the "easy sys" program, which is based on law of mass action (Schittkowski K. (1994), Numerische Mathematik, Vol. 68, 129-142).

All of the above-referenced examples have been found to have an activity in this assay of 50 µM or less.

Based on the ability of the substances described by formula (I) to effectively bind to CCR2a range of therapeutic applications can be envisaged. The present invention provides a method for modulating or treating at least one MCP-1 related disease, in a cell, tissue, organ, animal, or patient, as known in the art or as described herein, using at least one CCR2 antagonist of the present invention. The present invention also provides a method for modulating or treating at least one MCP-1 related disease, in a cell, tissue, organ, animal, or patient including, but not limited to, at least one of malignant disease, metabolic disease, an immune or inflammatory related disease, a cardiovascular disease, an infectious disease, or a neurologic disease. Such conditions are selected from, but not limited to, diseases or conditions mediated by cell adhesion and/or angiogenesis. Such diseases or conditions include an immune disorder or disease, a cardiovascular disorder or disease, an infectious, malignant, and/or neurologic disorder or disease, or other known or specified MCP-1 related conditions. In particular, the CCR2 antagonists are useful for the treatment of diseases that involve angiogenesis such as disease of the eye and neoplastic disease, tissue remodeling such as restenosis, and proliferation of certain cells types particularly epithelial and squamous cell carcinomas. Particular indications include use in the treatment of atherosclerosis, restenosis, cancer metastasis, rheumatoid arthritis, diabetic retinopathy and macular degeneration. The antagonists may also be useful in the treatment of various fibrotic diseases such as idiopathic pulmonary fibrosis, diabetic nephropathy, hepatitis, and cirrhosis. Thus, the present invention provides a method for modulating or treating at least one CCR2 related disease, in a cell, tissue, organ, animal, or patient, as known in the art or as described herein, using at least one CCR2 antagonist of the present invention. Particular indications are discussed below:

Pulmonary Diseases

The present invention also provides a method for modulating or treating at least one malignant disease in a cell, tissue, organ, animal or patient, including, but not limited to, at least one of: pneumonia; lung abscess; occupational lung diseases caused be agents in the form or dusts, gases, or mists; asthma, bronchiolitis fibrosa obliterans, respiratory failure, hypersensitivity diseases of the lungs including hypersensitivity pneumonitis (extrinsic allergic alveolitis), allergic bronchopulmonary aspergillosis, and drug reactions; adult respiratory distress syndrome (ARDS), Goodpasture's Syndrome, chronic obstructive airway disorders (COPD), idiopathic interstitial lung diseases such as idiopathic pulmonary fibrosis and sarcoidosis, desquamative interstitial pneumonia, acute interstitial pneumonia, respiratory bronchiolitis-associated interstitial lung disease, idiopathic bronchiolitis obliterans with organizing pneumonia, lymphocytic interstitial pneumonitis, Langerhans' cell granulomatosis, idiopathic pulmonary hemosiderosis; acute bronchitis, pulmonary alveolar, proteinosis, bronchiectasis, pleural disorders, atelectasis, cystic fibrosis, and tumors of the lung, and pulmonary embolism.

Malignant Diseases

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, renal cell carcinoma?; breast cancer, nasopharyngeal carcinoma, malignant histiocytosis, paraneoplastic syndrome/hypercalcemia of malignancy, solid tumors, adenocarcinomas, squamous cell carcinomas, sarcomas, malignant melanoma, particularly metastatic melanoma, hemangioma, metastatic disease, cancer related bone resorption, cancer related bone pain, and the like.

Immune Related Diseases

The present invention also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitisluveitisloptic neuritis, idiopathic pulmonary fibrosis, systemic vasculitis/wegener's granulomatosis, sarcoidosis, orchitislvasectomy reversal procedures, allergiclatopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, traumalhemo-~hage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic diseases, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type IU hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal garnrnopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, OKT3 therapy, anti-CD3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998,2000), each entirely incorporated by reference.

Cardiovascular Diseases

The present invention also provides a method for modulating or treating at least one cardiovascular disease in a cell, tissue, organ, animal, or patient, including, but not limited to, at least one of cardiac 25 stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythrnias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one CCR2 antagonist to a cell, tissue, organ, animal or patient in need of such modulation, treatment or therapy.

Neurologic Diseases

The present invention also provides a method for modulating or treating at least one neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supra-nucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetaliproprotemia, ataxia, telangiectasia, and mitochondrial multisystem disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16Ih Edition, Merck & Company, Rahway, N.J. (1992).

Fibrotic Conditions

In addition to the above described conditions and diseases, the present invention also provides a method for modulating or treating fibrotic conditions of various etiologies such as liver fibrosis (including but not limited to alcohol-induced cirrhosis, viral-induced cirrhosis, autoimmune-induced hepatitis); lung fibrosis (including but not limited to scleroderma, idiopathic pulmonary fibrosis); kidney fibrosis (including but not limited to scleroderma, diabetic nephritis, glomerular pehpritis, lupus nephritis); dermal fibrosis (including but not limited to scleroderma, hypertrophic and keloid scarring, burns); myelofibrosis; Neurofibromatosis; fibroma; intestinal fibrosis; and fibrotic adhesions resulting from surgical procedures.

The present invention also provides a method for modulating or treating at least one wound, trauma or tissue injury or chronic condition resulting from or related thereto, in a cell, tissue, organ, animal or patient, including, but not limited to, at least one of: bodily injury or a trauma associated with surgery including thoracic, abdominal, cranial, or oral surgery; or wherein the wound is selected from the group consisting of aseptic wounds, contused wounds, incised wounds, lacerated wounds, non-penetrating wounds, open wounds, penetrating wounds, perforating wounds, puncture wounds, septic wounds, infarctions and subcutaneous wounds; or wherein the wound is selected from the group consisting of ischemic ulcers, pressure sores, fistulae, severe bites, thermal burns and donor site wounds; or wherein the wound is anaphthous wound, a traumatic wound or a herpes associated wound. Donor site wounds are wounds which e.g. occur in connection with removal of hard tissue from one part of the body to another part of the body e.g. in connection with transplantation. The wounds resulting from such operations are very painful and an improved healing is therefore most valuable. Wound fibrosis is also amenable to CCR2 antagonist therapy as the first cells to invade the wound area are neutrophils followed by monocytes which are activated by macrophages. Macrophages are believed to be essential for efficient wound healing in that they also are responsible for phagocytosis of pathogenic organisms and a clearing up of tissue debris. Furthermore, they release numerous factors involved in subsequent events of the healing process. The macrophages attract fibroblasts which start the production of collagen. Almost all tissue repair processes include the early connective tissue formation, a stimulation of this and the subsequent processes improve tissue healing, however, overproduction of connective tissue and collegen can lead to a fibrotic tissue characterized as inelastic and hypoxic. The CCR2 antagonist of the invention can be used in methods for modulating, treating or preventing such sequelae of wound healing. The present antibodies of the present invention may also be used in methods for modulating or treating at least one symptom of chronic rejection of a transplanted organ, tissue or cell, such as a cardiac transplant.

Other Therapeutic Uses of CCR2 Antagonists

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infectionfHIV neuropathy, meningitis, hepatitis (A, B or C, or the like), septic arthritis, peritonitis, pneumonia, epiglottitis, *E. coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium* intracellulare, *pneumocystis carinii* pneumonia, pelvic inflammatory disease, orchitislepidydimitis, *legionella*, lyme disease, influenza a, epstein-barr virus, vital-associated hemaphagocytic syndrome, vital encephalitisiaseptic meningitis, and the like.

Any method of the present invention can comprise administering an effective amount of a composition or pharmaceutical composition comprising at least one CCR2 antagonist to a cell, tissue, organ, animal or patient in need of such modulation, treatment or therapy. Such a method can optionally further at least one selected from at least one TNFantagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NS-), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod (dexamethasone), an anabolic steroid (testosterone), a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin (rituximab), an immunosuppressive (e.g., basilixirnab, cyclosporine, daclizumab), a growth hormone, a hormone antagonist, a reproductive hormone antagonist (flutamide, nilutamide), a hormone release modulator (leuprolide, goserelin), a hormone replacement drug, an estrogen receptor modulator (tamoxifen), a retinoid (tretinoin), a topoisomerase inhibitor (etoposide, irinotecan), a cytoxin (doxorubicin), a mydriatic, a cycloplegic, an alkylating agent (carboplatin), a nitrogen mustard (melphalen, chlorabucil), a nitrosourea (carmustine, estramustine) an antimetabolite (methotrexate, cytarabine, fluorouracil), a mitotic inhibitor (vincristine, taxol), a radiopharmaceutical (Iodine13 1-tositumomab), a radiosensitizer (misonidazole, tirapazamine) an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine (interferon alpha-2, IL2) or a cytokine antagonist (infliximab). Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Particular combinations for treatment of neoplastic diseases comprise co-administration or combination therapy by administering, before concurrently, and/or after, an antineplastic agent such as an alkylating agent, a nitrogen mustard, a nitrosurea, an antibiotic, an anti-metabolite, a hormonal agonist or antagonist, an immunomodulator, and the like. For use in metastatic melanoma and other neoplastic diseases, a preferred combination is to co-administer the antagonist with dacarbazine, interferon alpha, interleukin-2, temozolomide, cisplatin, vinblastine, Imatinib Mesylate, carmustine, paclitaxel and the like. For metastatic melanoma, dacarbazine is preferred.

Combinations

The compounds of formula 1 may be used on their own or in conjunction with other active substances of formula 1 according to the invention. If desired the compounds of formula 1 may also be used in combination with other pharmacologically active substances. It is preferable to use for this purpose active substances selected for example from among betamimetics, anticholinergics, corticosteroids, other PDE4-inhibitors, LTD4-antagonists, EGFR-inhibitors, MRP4-inhibitors, dopamine agonists, H1-antihistamines, PAF-antagonists and PI3-kinase inhibitors, CXCR1 antagonists, CXCR2 antagonists, CCR1 antagonists, CCR3 antagonists, 5-LO antagonists, p38 MAP kinase inhibitors, FLAP antagonists, PI3 kinase inhibitors, ENaC inhibitorsm, SYK inhibitors or double, triple or higher combinations thereof, such as for example combinations of compounds of formula 1 with one or two compounds selected from among betamimetics, corticosteroids, PDE4-inhibitors, EGFR-inhibitors and LTD4-antagonists,
anticholinergics, betamimetics, corticosteroids, PDE4-inhibitors, EGFR-inhibitors and LTD4-antagonists,
PDE4-inhibitors, corticosteroids, EGFR-inhibitors and LTD4-antagonists
EGFR-inhibitors, PDE4-inhibitors and LTD4-antagonists
EGFR-inhibitors and LTD4-antagonists
CCR3 antagonists, iNOS-inhibitors (inducible nitric oxide synthase-inhibitors), (6R)-L-erythro-5,6,7,8-tetrahydrobiopterin (hereinafter referred to as "BH4") and the derivatives thereof as mentioned in WO 2006/120176 and SYK-inhibitors (spleen tyrosine kinase-inhibitors)
anticholinergics, betamimetics, corticosteroids, PDE4-inhibitors and MRP4-inhibitors.

The invention also encompasses combinations of three active substances, each selected from one of the above-mentioned categories of compounds.

The betamimetics used are preferably compounds selected from among albuterol, bambuterol, bitolterol, broxaterol, carbuterol, clenbuterol, fenoterol, formoterol, arformoterol, zinterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenol, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzyl-sulphonamide, 5-[2-(5,6-diethyl-indan-2-ylamino)-1-hydroxyethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H—S-hydroxy-3-oxo-4H-1,4-benzoxazin-8-yl]-2-[3-(4-N,N-dimethylaminophenyl)-2-methyl-2-propylamino]ethanol, 1-[2H—S-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H—S-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino) ethanol, 6-hydroxy-8-{1-hydroxy-2-[2-(4-methoxyphenyl)-1,1-dimethyl-ethylamino]-ethyl}-4H-benzo[1,4] oxazin-3-one, 6-hydroxy-8-{1-hydroxy-2-[2-(4-phenoxyacetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxy-carbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Preferably the beta mimetics are selected from among bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H—S-hydroxy-3-oxo-4H-1,4-benzoxazin-8-yl]-2-[3-(4-N,N-dimethylaminophenyl)-2-methyl-2-propylamino]ethanol, 1-[2H—S-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H—S-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino) ethanol, 6-hydroxy-8-{1-hydroxy-2-[2-(4-methoxyphenyl)-1,1-dimethyl-ethylamino]-ethyl}-4H-benzo[1,4] oxazin-3-one, 6-hydroxy-8-{1-hydroxy-2-[2-(4-phenoxyacetate ethyl)-1,1-dimethyl-ethylamino]-ethyl}-4H-benzo [1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1.1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1- dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxycarbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Particularly preferred betamimetics are selected from among fenoterol, formoterol, salmeterol, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 1-[3-(4-methoxybenzyl-amino)-4-hydroxyphenyl]-2-[4-(1-benzimidazolyl)-2-methyl-2-butylamino]ethanol, 1-[2H—S-hydroxy-3-oxo-4H-1,4-benzoxazin-8-yl]-2-[3-(4-N,N-dimethylaminophenyl)-2-methyl-2-propylamino]ethanol, 1-[2H—S-hydroxy-3-oxo-4H-1,4-benzoxazin-8-yl]-2-[3-(4-methoxyphenyl)-2-methyl-2-propylamino]ethanol, 1-[2H—S-hydroxy-3-oxo-4H-1,4-benzoxazin-8-yl]-2-[3-(4-n-butyloxyphenyl)-2-methyl-2-propylamino]ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1.1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, enantiomers, diastereomers thereof and optionally in the form of the pharmacologically acceptable acid addition salts, solvates or hydrates thereof.

Of these betamimetics those which are particularly preferred according to the invention are formoterol, salmeterol, 3-(4-{6-[2-hydroxy-2-(4-hydroxy-3-hydroxymethyl-phenyl)-ethylamino]-hexyloxy}-butyl)-benzenesulphonamide, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1.1-dimethyl-ethylamino]-ethyl}-4H-benzo[1,4] oxazin-3-one, 8-{2-[2-(4-ethyl-phenyl)-1,1-dimethyl-ethylamino]-1-hydroxy-ethyl}-6-hydroxy-4H-benzo[1,4] oxazin-3-one, 8-{2-[2-(4-ethoxy-phenyl)-1,1-dimethyl-ethylamino]-1-hydroxy-ethyl}-6-hydroxy-4H-benzo[1,4] oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 5-[2-(5,6-diethyl-indan-2-ylamino)-1-hydroxy-ethyl]-8-hydroxy-1H-quinolin-2-one, optionally in the form of the racemates, enantiomers, diastereomers thereof and optionally in the form of the pharmacologically acceptable acid addition salts, solvates or hydrates thereof.

According to the invention the acid addition salts of the betamimetics are preferably selected from among hydrochloride, hydrobromide, hydriodide, hydrosulphate, hydrophosphate, hydromethanesulphonate, hydronitrate, hydromaleate, hydroacetate, hydrobenzoate, hydrocitrate, hydrofumarate, hydrotartrate, hydroxalate, hydrosuccinate, hydrobenzoate and hydro-p-toluenesulphonat, preferably hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among the tiotropium salts, oxitropium salts, flutropium salts, ipratropium salts, glycopyrronium salts, trospium salts, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, -scopine 3,3'-difluorobenzilate methobromide, tropenol 9-hydroxy-fluorene-9-carboxylate-methobromide, tropenol 9-fluoro-fluorene-9-carboxylate -methobromide, scopine 9-hydroxy-fluoren-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, methyl -cyclopropyltropine 4,4'-difluorobenzilate methobromide, tropenol 9-hydroxy-xanthene-9-carboxylate -methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide, scopine 9-hydroxymethyl-xanthene-9-carboxylate methobromide, optionally in the form of the solvates or hydrates thereof.

In the above-mentioned salts the cations tiotropium, oxitropium, flutropium, ipratropium, glycopyrronium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among prednisolone, prednisone, butixocortpropionate, flunisolide, beclomethasone, triamcinolone, budesonide, fluticasone, mometasone, ciclesonide, rofleponide, dexamethasone, betamethasone, deflazacort, RPR-106541, NS-126, (S)-fluoromethyl 6,9-difluoro-17-[(2-furanylcarbonyl)oxy]-11-hydroxy-16-methyl-3-oxo-androsta-1, 4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferred is the steroid selected from among flunisolide, beclomethasone, triamcinolone, budesonide, fluticasone, mometasone, ciclesonide, rofleponide, dexamethasone, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferred is the steroid selected from among budesonide, fluticasone, mometasone, ciclesonide and (S)-fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates thereof.

Other PDE4 inhibitors which may be used are preferably compounds selected from among enprofyllin, theophyllin, roflumilast, ariflo (cilomilast), tofimilast, pumafentrin, lirimilast, arofyllin, atizoram, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370, N-(3,5-dichloro-1-oxo-pyridin-4-yl)-4-difluoromethoxy-3-cyclopropyl-methoxybenzamide, $(-)_p$-[(4aR*,10b S*)-9-ethoxy-1,2,3,4,4a,10b-hexahydro -8-methoxy-2-methylbenzo[s][1,6] naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexane-1-one, cis[4-cyano-4-(3-cyclopropylmethoxy-4-difluoromethoxyphenyl) cyclohexan-1-ol], (R)-(+)-ethyl[4-(3-cyclopentyloxy-4-methoxyphenyl)pyrrolidin-2-ylidene]acetate, (S)-(−)-ethyl [4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

Particularly preferably the PDE4-inhibitor is selected from among enprofyllin, roflumilast, ariflo (cilomilast), arofyllin, atizoram, AWD-12-281 (GW-842470), T-440, T-2585, PD-168787, V-11294A, CI-1018, CDC-801, D-22888, YM-58997, Z-15370, N-(3,5-dichloro-1-oxo-pyridin-4-yl)-4-difluoromethoxy-3-cyclopropylmethoxybenzamide, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl) cyclohexan-1-one, cis[4-cyano-4-(3-cyclopropylmethoxy-4-difluoromethoxyphenyl)cyclohexan-1-ol], 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

Particularly preferably the PDE4-inhibitor is selected from among roflumilast, ariflo (cilomilast), arofyllin, AWD-12-281 (GW-842470), 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], atizoram, Z-15370, 9-cyclopentyl-5,6-dihydro-7-ethyl-3-(2-thienyl)-9H-pyrazolo[3,4-c]-1, 2,4-triazolo[4,3-a]pyridine and 9-cyclopentyl-5,6-dihydro-7-ethyl-3-(tert-butyl)-9H-pyrazolo[3,4-c]-1,2,4-triazolo[4, 3-a]pyridine, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2.3-dichloro thieno[3,2-b]pyridin-5-yl)-(E)-ethenyl)phenyl)-3-(2-(1-hydroxy-1-methylethyl) phenyl)propyl)thio)methyl)cyclopropane-acetic acid and [2-[[2-(4-tert-butyl-2-thiazolyl)-5-benzofuranyl]oxymethyl] phenyl]acetic acid, optionally in the form of the racemates, enantiomers or diastereomers, optionally in the form of the pharmacologically acceptable acid addition salts and optionally in the form of the salts and derivatives, solvates and/or hydrates thereof.

Preferably the LTD4-antagonist is selected from among montelukast, pranlukast, zafirlukast, MCC-847 (ZD-3523), MN-001, MEN-91507 (LM-1507), VUF-5078, VUF-K-8707 and L-733321, optionally in the form of the racemates, enantiomers or diastereomers, optionally in the form of the pharmacologically acceptable acid addition salts and optionally in the form of the salts and derivatives, solvates and/or hydrates thereof.

Particularly preferably the LTD4-antagonist is selected from among montelukast, pranlukast, zafirlukast, MCC-847 (ZD-3523), MN-001 and MEN-91507 (LM-1507), optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

The EGFR-inhibitors used are preferably compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidin, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methane sulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5.5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxyethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2.6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(5)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, Cetuximab, Trastuzumab, ABX-EGF and Mab ICR-62, optionally in the form of the racemates, enantiomers or diastereomers thereof, optionally in the form of the pharmacologically acceptable acid addition salts, the solvates and/or hydrates thereof.

Preferred EGFR inhibitors are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2- methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methane sulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5.5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydrofuran-4-yloxy)-7-(2-methoxy-ethoxy)-quinazoline, 4-[(3-chloro-4-fluoro-phenyl)amino]-6-{trans-4[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynylphenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2.6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl) amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and Cetuximab, optionally in the form of the racemates, enantiomers or diastereomers thereof, optionally in the form of the pharmacologically acceptable acid addition salts, the solvates and/or hydrates thereof.

It is particularly preferable within the scope of the present invention to use those EGFR-inhibitors which are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5.5-dimethyl-2-oxo-morpholin-4-yl)-1-oxo-2-buten-1-yl] amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7-(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxyquinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxy-ethyl)carbonyl]-piperidin-4-yloxy}-7-methoxy-quinazoline, optionally in the form of the racemates, enantiomers or diastereomers thereof, optionally in the form of the pharmacologically acceptable acid addition salts, the solvates and/or hydrates thereof.

Particularly preferred EGFR-inhibitors according to the invention are the compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluoro -phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-ethynyl-phenyl)amino]-6,7-bis-(2-methoxy-ethoxy)-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4(5.5-dimethyl-2-oxo-morpholin-4-yl)-1-oxo-2-buten-1-yl]amino}-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline and 4-[(3-chloro-4-fluoro-phenyl)amino]-6-(1-cyano-piperidin-4-yloxy)-7-methoxy-quinazoline optionally in the form of the racemates, enantiomers or diastereomers thereof, optionally in the form of the pharmacologically acceptable acid addition salts, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among 4-(2-chlorophenyl)-9-methyl-2-[3(4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4] diazepines.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-β-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, clycolithocholic acid sulphate, ibuprofen, indomethacin, indoprofen, ketoprofen, lithocholic acid sulphate, methotrexate, MK571 ((E)-3-[[[3-[2-(7-chloro-2-quinolinyl)ethenyl]phenyl]-[[3-dimethylamino)-3-oxopropyl]thio]methyl]thio]-propanoic acid), α-naphthyl-β-D-glucuronide, nitrobenzyl mercaptopurine riboside, probenecid, PSC833, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

Preferably the invention relates to the use of MRP4-inhibitors for preparing a pharmaceutical composition for the treatment of respiratory complaints, containing the PDE4B-inhibitors and MRP4-inhibitors, the MRP4-inhibitors preferably being selected from among N-acetyl-dinitrophenyl-cysteine, dehydroepiandrosterone 3-sulphate, dilazep, dinitrophenyl-S-glutathione, estradiol 3,17-disulphate, flurbiprofen, glycocholate, glycolithocholic acid sulphate, ibuprofen, indomethacin, indoprofen, lithocholic acid sulphate, MK571, PSC833, sildenafil, taurochenodeoxycholate, taurocholate, taurolithocholate, taurolithocholic acid sulphate, trequinsin and zaprinast, dipyridamole, optionally in the form of the racemates, enantiomers, diastereomers and the pharmacologically acceptable acid addition salts and hydrates thereof.

The invention relates more preferably to the use of MRP4-inhibitors for preparing a pharmaceutical composition for treating respiratory complaints, containing the PDE4B-inhibitors and MRP4-inhibitors according to the invention, the MRP4-inhibitors preferably being selected from among dehydroepiandrosterone 3-sulphate, estradiol 3,17-disulphate, flurbiprofen, indomethacin, indoprofen, MK571, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydro succinates, hydrobenzoates and hydro-p-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the PDE4B-inhibitors, MRP4-inhibitors and another active substance according to the invention, such as, for example, an anticholinergic, a steroid, an LTD4-antagonist or a betamimetic, and the preparation thereof and the use thereof for treating respiratory complaints.

The iNOS-inhibitors used are preferably compounds selected from among: S-(2-aminoethyl)isothiourea, aminoguanidine, 2-aminomethylpyridine, AMT, L-canavanine, 2-iminopiperidine, S-isopropylisothiourea, S-methylisothiourea, S-ethylisothiourea, S-methylthiocitrulline, S-ethylthiocitrulline, L-NA (N$^\omega$-nitro-L-arginine), L-NAME (N$^\omega$-nitro-L-arginine methylester), L-NMMA (N$^G$-monomethyl-L-arginine), L-NIO (N$^\omega$-iminoethyl-L-ornithine), L-NIL (N$^\omega$-iminoethyl-lysine), (S)-6-acetimidoylamino-2-aminohexanoic acid (1H-tetrazol-5-yl)-amide (SC-51) (*J. Med. Chem.* 2002, 45, 1686-1689), 1400W, (S)-4-(2-acetimidoylamino-ethylsulphanyl)-2-amino-butyric acid (GW274150) (*Bioorg. Med. Chem. Lett.* 2000, 10, 597-600), 2-[2-(4-methoxy-pyridin-2-yl)-ethyl]-3H-imidazo[4,5-b]pyridine (BYK191023) (*Mol. Pharmacol.* 2006, 69, 328-337), 2-((R)-3-amino-1-phenyl-propoxy)-4-chloro-5-fluorobenzonitrile (WO 01/62704), 2-((1R,3S)-3-amino-4-hydroxy-1-thiazol-5-yl-butylsulphanyl)-6-trifluoromethyl-nicotinonitrile (WO 2004/041794), 2-((1R,3S)-3-amino-4-hydroxy-1-thiazol-5-yl-butylsulphanyl)-4-chloro-benzonitrile (WO 2004/041794), 2-((1R,3S)-3-amino-4-hydroxy-1-thiazol-5-yl-butylsulphanyl)-5-chloro-benzonitrile (WO 2004/041794), (2S,4R)-2-amino-4-(2-chloro-5-trifluoromethyl-phenylsulphanyl)-4-thiazol-5-yl-butan-1-ol (WO 2004/041794), 2-((1R,3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamines such as e.g. AR-C102222 (*J. Med. Chem.* 2003, 46, 913-916), (1S.5S.6R)-7-chloro-5-methyl-2-aza-bicyclo[4.1.0]hept-2-en-3-ylamine (ONO-1714) (*Biochem. Biophys. Res. Commun.* 2000, 270, 663-667), (4R, 5R)-5-ethyl-4-methyl-thiazolidin-2-ylideneamine (*Bioorg. Med. Chem.* 2004, 12, 4101), (4R,5R)-5-ethyl-4-methyl-selenazolidin-2-ylideneamine (*Bioorg. Med. Chem. Lett.* 2005, 15, 1361), 4-aminotetrahydrobiopterine (*Curr. Drug Metabol.* 2002, 3, 119-121), (E)-3-(4-chloro-phenyl)-N-(1-{2-oxo-2-[4-(6-trifluoromethyl-pyrimidin-4-yloxy)-piperidin-1-yl]-ethylcarbamoyl}-2-pyridin-2-yl-ethyl)-acrylamide (FR260330) (*Eur. J. Pharmacol.* 2005, 509, 71-76), 3-(2,4-difluoro-phenyl)-6-[2-(4-imidazol-1-ylmethyl-phenoxy)-ethoxy]-2-phenyl-pyridine (PPA250) (*J. Pharmacol. Exp. Ther.* 2002, 303, 52-57), methyl 3-{[benzo[1.3]dioxol-5-yl-methyl)-carbamoyl]-methyl}-4-(2-imidazol-1-yl-pyrimidin-4-yl)-piperazin-1-carboxylate (BBS-1) (*Drugs Future* 2004, 29, 45-52), (R)-1-(2-imidazol-1-yl-6-methyl-pyrimidin-4-yl)-pyrrolidine-2-carboxylic acid (2-benzo[1.3]dioxol-5-yl-ethyl)-amide (BBS-2) (Drugs Future 2004, 29, 45-52) and the pharmaceutical salts, prodrugs or solvates thereof.

Other iNOS-inhibitors which may be used within the scope of the present invention are antisense oligonucleotides, particularly antisense oligonucleotides that bind iNOS-coding nucleic acids. For example, WO 01/52902 describes antisense oligonucleotides, particularly antisense-oligonucleotides, which bind iNOS-coding nucleic acids, for modulating the expression of iNOS. Those iNOS-antisense-oligonucleotides as described particularly in WO 01/52902 may therefore also be combined with the PDE4-inhibitors of the present invention on the basis of their similar activity to the iNOS inhibitors.

Compounds which may be used as SYK-inhibitors are preferably compounds selected from among: 2-[(2-aminoethyl)amino]-4-[(3-bromophenyl)amino]-5-pyrimidinecarboxamide;

2-[[7-(3,4-dimethoxyphenyl)imidazo[1,2-c]pyrimidin-5-yl]amino]-3-pyridinecarboxamide;

6-[[5-fluoro-2-[3,4,5-trimethoxyphenyl)amino]-4-pyrimidinyl]amino]-2,2-dimethyl-2H-pyrido[3,2-b]-1,4-oxazin-3 (4H)-one;

N-[3-bromo-7-(4-methoxyphenyl)-1,6-naphthyridin-5-yl]-1,3-propanediamine 7-(4-methoxyphenyl)-N-methyl-1,6-naphthyridin-5-amine;

N-[7-(4-methoxyphenyl)-1,6-naphthyridin-5-yl]-1,3-propanediamine;

N-[7-(2-thienyl)-1,6-naphthyridin-5-yl-1,3-propanediamine;

N-[7-[4-(dimethylamino)phenyl]-1,6-naphthyridin-5-yl]-1,2-ethanediamine;

N-[7-(4-methoxyphenyl)-2-(trifluoromethyl)-1,6-naphthyridin-5-yl]-1,3-propanediamine;

N-[7-(4-methoxyphenyl)-3-phenyl-1,6-naphthyridin-5-yl]-1,3-propanediamine;

N-(7-phenyl-1,6-naphthyridin-5-yl)-1,3-propanediamine;

N-[7-(3-fluorophenyl)-1,6-naphthyridin-5-yl]-1,3-propanediamine;

N-[7-(3-chlorophenyl)-1,6-naphthyridin-5-yl]-1,3-propanediamine;

N-[7-[3-(trifluoromethoxy)phenyl]-1,6-naphthyridin-5-yl]-1,3-propanediamine;
N-[7-(4-fluorophenyl)-1,6-naphthyridin-5-yl]-1,3-propanediamine;
N-[7-(4-fluorophenyl)-1,6-naphthyridin-5-yl]-1,3-propanediamine;
N-[7-(4-chlorophenyl)-1,6-naphthyridin-5-yl]-1,3-propanediamine;
N-[7-(4'-methyl[1,1'-biphenyl]-4-yl)-1,6-naphthyridin-1,3-propanediamine;
N-[7-[4-(dimethylamino)phenyl]-1,6-naphthyridin-5-yl]-1,3-propanediamine;
N-[7-[4-(diethylamino)phenyl]-1,6-naphthyridin-5-yl]-1,3-propanediamine;
N-[7-[4-(4-morpholinyl)phenyl]-1,6-naphthyridin-5-yl]-1,3-propanediamine;
N-[7-[4-[[2-(dimethylamino)ethyl]methylamino]phenyl]-1,6-naphthyridin-5-yl]-1,3-propanediamine;
N-[7-(4-bromophenyl)-1,6-naphthyridin-5-yl]-1,3-propanediamine;
N-[7-(4-methylphenyl)-1,6-naphthyridin-5-yl]-1,3-propanediamine;
N-[7-[4-(methylthio)phenyl]-1,6-naphthyridin-5-yl]-1,3-propanediamine;
N-[7-[4-(1-methylethyl)phenyl]-1,6-naphthyridin-5-yl]-1,3-propanediamine;
7-[4-(dimethylamino)phenyl]-N-methyl-1,6-naphthyridin-5-amine;
7-[4-(dimethylamino)phenyl]-N,N-dimethyl-1,6-naphthyridin-5-amine;
N-[7-[4-(dimethylamino)phenyl]-1,6-naphthyridin-5-yl]-1,4-butanediamine;
N-[7-[4-(dimethylamino)phenyl]-1,6-naphthyridin-5-yl]-1,5-pentanediamine;
3-[[7-[4-(dimethylamino)phenyl]-1,6-naphthyridin-5-yl]oxy]-1-propanol;
4-[5-(4-aminobutoxy)-1,6-naphthyridin-7-yl]-N,N-dimethyl-benzenamine;
4-[[7-[4-(dimethylamino)phenyl]-1,6-naphthyridin-5-yl]amino]-1-butanol;
N-[7-[4-(dimethylamino)phenyl]-1,6-naphthyridin-5-yl]-N-methyl-1,3-propanediamine;
N-[7-[4-(dimethylamino)phenyl]-1,6-naphthyridin-5-yl]-N'-methyl-1,3-propanediamine;
N-[7-[4-(dimethylamino)phenyl]-1,6-naphthyridin-5-yl]-N,N'-dimethyl-1,3-propanediamine;
1-amino-3-[[7-[4-(dimethylamino)phenyl]-1,6-naphthyridin-5-yl]amino]-2-propanol;
N-[7-[4-(dimethylamino)phenyl]-1,6-naphthyridin-5-yl]-2,2-dimethyl-1,3-propanediamine;
7-[4-(dimethylamino)phenyl]-N-(3-pyridinylmethyl)-1,6-naphthyridin-5-amine;
N-[(2-aminophenyl)methyl]-7-[4-(dimethylamino)phenyl]-1,6-naphthyridin-5-amine;
N-[7-[6-(dimethylamino)[1,1'-biphenyl]-3-yl]-1,6-naphthyridin-5-yl]-1,3-propanediamine;
N-[7-[3-chloro-4-(diethylamino)phenyl]-1,6-naphthyridin-5-yl]-1,3-propanediamine;
N-[7-[4-(dimethylamino)-3-methoxyphenyl]-1,6-naphthyridin-5-yl]-1,3-propanediamine;
N-[7-[4-(diethylamino)phenyl]-3-methyl-1,6-naphthyridin-5-yl]-1,3-propanediamine;
N-[7-(3'-fluoro[1,1'-biphenyl]-3-yl)-1,6-naphthyridin-5-yl]-1,2-ethanediamine;
N-[7-(4-methoxyphenyl)-1,6-naphthyridin-5-yl]-1,6-naphthyridine-1,3-propanediamine;
N,N'-bis(3-aminopropyl)-7-(4-methoxyphenyl)-2,5-diamine;
N-[7-(4-methoxyphenyl)-2-(phenylmethoxy)-1,6-naphthyridin-5-yl]-1,6-naphthyridine-1,3-propanediamine;
N5-(3-aminopropyl)-7-(4-methoxyphenyl)-$N^2$-(phenylmethyl)-2,5-diamine;
N-[7-(2-naphthalenyl)-1,6-naphthyridin-5-yl]-1,3-propanediamine;
N-[7-(2'-fluoro[1,1'-biphenyl]-4-yl)-1,6-naphthyridin-5-yl]-1,3-propanediamine;
N-[7-(3,4,5-trimethoxyphenyl)-1,6-naphthyridin-5-yl]-1,3-propanediamine;
N-[7-(3,4-dimethylphenyl)-1,6-naphthyridin-5-yl]-1,3-propanediamine;
1-amino-3-[[7-(2-naphthalenyl)-1,6-naphthyridin-5-yl]amino]-2-propanol;
1-amino-3-[[7-(2'-fluoro[1,1'-biphenyl]-4-yl)-1,6-naphthyridin-5-yl]amino]-2-propanol;
1-amino-3-[[7-(4'-methoxy[1,1'-biphenyl]-4-yl)-1,6-naphthyridin-5-yl]amino]-2-propanol;
1-amino-3-[[7-(3,4,5-trimethoxyphenyl)-1,6-naphthyridin-5-yl]amino]-2-propanol;
1-amino-3-[[7-(4-bromophenyl)-1,6-naphthyridin-5-yl]amino]-2-propanol;
N-[7-(4'-methoxy[1,1'-biphenyl]-4-yl)-1,6-naphthyridin-5-yl]-2,2-dimethyl-1,3-propanediamine;
1-[[7-[4-(dimethylamino)phenyl]-1,6-naphthyridin-5-yl]amino]-2-propanol;
2-[[2-[[7-[4-(dimethylamino)phenyl]-1,6-naphthyridin-5-yl]amino]ethyl]thio]-ethanol;
7-[4-(dimethylamino)phenyl]-N-(3-methyl-5-isoxazolyl)-1,6-naphthyridin-5-amine;
7-[4-(dimethylamino)phenyl]-N-4-pyrimidinyl-1,6-naphthyridin-5-amine;
N-[7-[4-(dimethylamino)phenyl]-1,6-naphthyridin-5-yl]-1,3-cyclohexanediamine;
N,N-dimethyl-4-[5-(1-piperazinyl)-1,6-naphthyridin-7-yl]-benzenamine;
4-[5-(2-methoxyethoxy)-1,6-naphthyridin-7-yl]-N,N-dimethyl-benzenamine;
1-[7-[4-(dimethylamino)phenyl]-1,6-naphthyridin-5-yl]-4-piperidinol;
1-[7-[4-(dimethylamino)phenyl]-1,6-naphthyridin-5-yl]-3-pyrrolidinol;
7-[4-(dimethylamino)phenyl]-N-(2-furanylmethyl)-1,6-naphthyridin-5-amine;
7-[4-(dimethylamino)phenyl]-N-[3-(1H-imidazol-1-yl)propyl]-1,6-naphthyridin-5-amine;
1-[7-[4-(dimethylamino)phenyl]-1,6-naphthyridin-5-yl]-4-piperidinecarboxamide;
1-[3-[[7-[4-(dimethylamino)phenyl]-1,6-naphthyridin-5-yl]amino]propyl]-2-pyrrolidinone;
N-[3'-[5-[(3-aminopropyl)amino]-1,6-naphthyridin-7-yl][1,1'-biphenyl]-3-yl]-acetamide;
N-[7-(4'-fluoro[1,1'-biphenyl]-4-yl)-1,6-naphthyridin-5-yl]-1,3-propanediamine;
N-[4'-[5-[(3-aminopropyl)amino]-1,6-naphthyridin-7-yl][1,1'-biphenyl]-3-yl]-acetamide;
N-[7-[4-(1,3-benzodioxol-5-yl)phenyl]-1,6-naphthyridin-5-yl]-1,3-propanediamine;
N-[7-[4-(2-thienyl)phenyl]-1,6-naphthyridin-5-yl]-1,3-propanediamine;
N-[7-[4-fluoro-3-(trifluoromethyl)phenyl]-1,6-naphthyridin-5-yl]-1,3-propanediamine;
N-[7-[4-(3-pyridinyl)phenyl]-1,6-naphthyridin-5-yl]-1,3-propanediamine;

N-[7-(1,3-benzodioxol-5-yl)-1,6-naphthyridin-5-yl]-1,3-propanediamine;
N-[7-(6-methoxy-2-naphthalenyl)-1,6-naphthyridin-5-yl]-1,3-propanediamine;
7-[4-(dimethylamino)phenyl]-N-(4-pyridinylmethyl)-1,6-naphthyridin-5-amine;
3-[[7-[4-(dimethylamino)phenyl]-1,6-naphthyridin-5-yl]methylamino]-propanenitrile;
7-[4-(dimethylamino)phenyl]-N-[1-(phenylmethyl)-4-piperidinyl]-1,6-naphthyridin-5-amine;
N-[7-[4-(dimethylamino)phenyl]-1,6-naphthyridin-5-yl]-1,2-cyclohexanediamine, (1R,2S)-rel-.
N-[7-[4-(dimethylamino)phenyl]-1,6-naphthyridin-5-yl]-1,2-benzenedimethanamine;
N-[7-[4-(diethylamino)phenyl]-1,6-naphthyridin-5-yl]-1,4-butanediamine;
N-[7-[3',5'-bis(trifluoromethyl)[1,1'-biphenyl]-4-yl]-1,6-naphthyridin-5-yl].3-propanediamine;
N-[7-(3'-methoxy[1,1'-biphenyl]-4-yl)-1,6-naphthyridin-5-yl]-1,3-propanediamine;
N-[7-(3'-fluoro[1,1'-biphenyl]-4-yl)-1,6-naphthyridin-5-yl]-1,3-propanediamine;
4-[[7-[4-(dimethylamino)phenyl]-1,6-naphthyridin-5-yl]oxy]-1-butanol;
N-[7-[4-(dimethylamino)phenyl]-1,6-naphthyridin-5-yl]-1,4-cyclohexanediamine;
7-[4-(dimethylamino)phenyl]-N-(2.2.6.6-tetramethyl-4-piperidinyl)-1,6-naphthyridin-5-amine;
N-[7-[3-bromo-4-(dimethylamino)phenyl]-1,6-naphthyridin-5-yl]-1,3-propanediamine;
N-[7-(1-methyl-1H-indol-5-yl)-1,6-naphthyridin-5-yl]-1,3-propanediamine;
N-[7-[3-(trifluoromethyl)phenyl]-1,6-naphthyridin-5-yl]-1,3-propanediamine;
N-[7-[4-(trifluoromethyl)phenyl]-1,6-naphthyridin-5-yl]-1,3-propanediamine;
N-[7-(3-bromo-4-methoxyphenyl)-1,6-naphthyridin-5-yl]-1,3-propanediamine;
N-[7-[4-[[3-(dimethylamino)propyl]methylamino]phenyl]-1,6-naphthyridin-5-yl]-1,4-cyclohexanediamine;
N-[7-[4-[[2-(dimethylamino)ethyl]methylamino]phenyl]-1,6-naphthyridin-5-yl]-1,4-cyclohexanediamine;
N-[7-[4-(dimethylamino)-3-methoxyphenyl]-1,6-naphthyridin-5-yl]-1,4-cyclohexanediamine;
N-[7-[4-(4-morpholinyl)phenyl]-1,6-naphthyridin-5-yl]-1,4-cyclohexanediamine;
N-[7-[3-bromo-4-(4-morpholinyl)phenyl]-1,6-naphthyridin-5-yl]-1,4-cyclohexanediamine;
4-[[7-[4-[[2-(dimethylamino)ethyl]methylamino]phenyl]-1,6-naphthyridin-5-yl]oxy]-cyclohexanol;
N-[7-[3-bromo-4-(4-morpholinyl)phenyl]-1,6-naphthyridin-5-yl]-1,3-propanediamine;
N,N-dimethyl-4-[5-(4-methyl-1-piperazinyl)-1,6-naphthyridin-7-yl]-benzenamine;
4-[[7-[4-[[3-(dimethylamino)propyl]methylamino]phenyl]-1,6-naphthyridin-5-yl]oxy]-cyclohexanol;
N-[7-[4-[[2-(dimethylamino)ethyl]methylamino]phenyl]-1,6-naphthyridin-5-yl]-1,4-butanediamine;
1,1-dimethylethyl [3-[[5-[(3-aminopropyl)amino]-7-(4-methoxyphenyl)-1,6-naphthyridin-2-yl]amino]propyl]-carbamate.

Pharmaceutical Formulations

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised in that they contain one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. For the treatment forms described above, ready-to-use packs of a medicament for the treatment of respiratory complaints are provided, containing an enclosed description including for example the words respiratory disease, COPD or asthma, a pteridine and one or more combination partners selected from those described above.

EXPERIMENTAL

The amines which are used as substituents for pyrazoles and/or pyridazines are synthesized according to route A or route B.

Pyrazoles

General Methods:

Part of the amines used in Route A are synthesized according to route B.

Route A1
Preparation of Example 10:

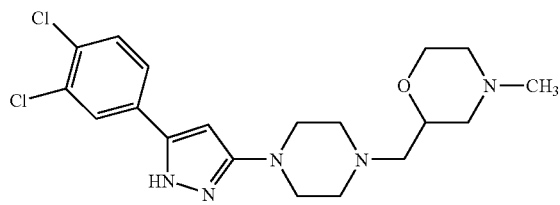 [SMILES: CN1CCOC(CN2CCN(c3cc(-c4ccc(Cl)c(Cl)c4)[nH]n3)CC2)C1]

4-Methyl-2-(piperazin-1-ylmethyl)morpholine (120 mg) is added to a solution of 1-(3,4-dichlorophenyl)-3,3-bis(methylthio)prop-2-en-1-one (75 mg) in ethanol (2 ml) and heated to 70° C. over night. Hydrazine-hydrate (37 µl) is added to the reaction mixture and the mixture is stirred over night at 70° C. The crude product is purified using reverse phase HPLC (Chromolith C18) eluting with a gradient of 10-90% acetonitrile in water containing 0.1% formic acid to give compound 10 (50 mg). m/z(+) 410/412/414 (M+H$^+$).

The N-Methylpiperazine used in the above procedure to synthesize 1, 3, 9 is commercially available and was purchased from Acros, 1,4'-bipiperidine used to synthesize 2 was purchased from Aldrich.

α-Ketoketene-S,S-diacetals are prepared by reaction of an acetophenone with carbon disulfide and subsequent methylation (D. Borrmann, Houben-Weyl, "Methoden der Organischen Chemie", Band VII/4, 1968, Georg Thieme Verlag, Stuttgart, 421):

1-(3,4-dichlorophenyl)-3,3-bis(methylthio)prop-2-en-1-one

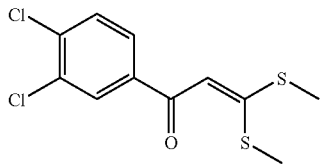 [SMILES: CSC(=CC(=O)c1ccc(Cl)c(Cl)c1)SC]

To a solution of 1-(3,4-dichlorophenyl)ethanone (1 g) in tert-butanol (38.5 g) is added KOtBu (1.2 g) and carbon dioxide (0.32 ml) and the mixture is stirred for 3 hours. After addition of iodomethane (0.66 ml), the reaction mixture is stirred over night. After removal of the solvent, the residue is dissolved in CH$_2$Cl$_2$ and washed with water. The organic layer is dried (Na$_2$SO$_4$) and filtered, and the solvent is removed under reduced pressure. The residue is dissolved in DMF and purified using reverse phase HPLC (Varian C18 Microsorb) eluting with a gradient of 10-100% acetonitrile in water containing 0.2% trifluoroacetic acid to give 1-(3,4-dichlorophenyl)-3,3-bis(methylthio)prop-2-en-1-one (320 mg). m/z(+) 293/295/297 (M+H$^+$).

The 1-(3,4-dichlorophenyl)ethanone used in the above procedure is commercially available and was purchased from Aldrich. The 1-(4-chlorophenyl)ethanone used to synthesize 8, 9 was purchased from Aldrich, 1-(3,5-dichlorophenyl) ethanone used to synthesize 13 was purchased from ABCR, 1-(4-bromophenyl)ethanone used to synthesize 1, 14 was purchased from Fluka.

4-methyl-2-(piperazin-1-ylmethyl)morpholine

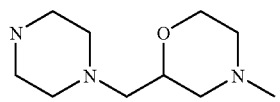

2-((4-benzylpiperazin-1-yl)methyl)-4-methylmorpholine (346 mg) is dissolved in ethanol (10 ml). Palladium on carbon (100 mg) is added and the mixture is stirred for 5 hours at 50° C. under an atmosphere of hydrogen (50 psi). The catalyst is removed by filtration and the filtrate concentrated under reduced pressure to give 4-methyl-2-(piperazin-1-ylmethyl) morpholine (234 mg). m/z(+) 200 (M+H$^+$).

2-((4-benzylpiperazin-1-yl)methyl)-4-methylmorpholine

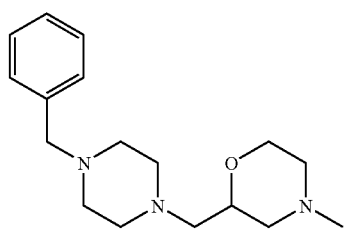 [SMILES: CN1CCOC(CN2CCN(Cc3ccccc3)CC2)C1]

Sodium triacetoxyborohydride (715 mg) is added to a mixture of 2-((4-benzylpiperazin-1-yl)methyl)morpholine*3 TFA (990 mg), an aqueous solution of formaldehyde (37%, 195 µl), acetic acid (245 µl) and THF (830 ml), and the mixture is stirred over night. An aqueous solution of potassium carbonate (15%) is added and the mixture stirred for 15 min. The organic layer is separated and the aqueous layer is extracted with CH$_2$Cl$_2$. The combined organic layers are washed with satd. aqueous NH$_4$Cl (2×), dried (Na$_2$SO$_4$) and filtered, and the solvent is removed under reduced pressure to give 24(4-benzylpiperazin-1-yl)methyl)-4-methylmorpholine (346 mg) m/z(+) 290 (M+H$^+$).

2-((4-benzylpiperazin-1-yl)methyl)morpholine

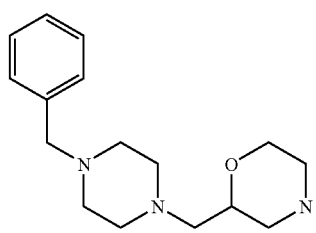 [SMILES: c1ccc(CN2CCN(CC3CNCCO3)CC2)cc1]

To a solution of tert-butyl 2-((4-benzylpiperazin-1-yl)methyl)morpholine-4-carboxylate (600 mg) in CH$_2$Cl$_2$ (10 ml) is added trifluoroacetic acid (1.8 ml), and the mixture is stirred over night. The solvent is removed under reduced pressure to give 2-((4-benzylpiperazin-1-yl)methyl)morpholine*3 TFA (990 mg).

tert-butyl 2-((4-benzylpiperazin-1-yl)methyl)morpholine-4-carboxylate

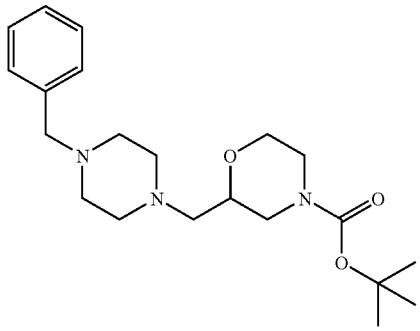 [SMILES: CC(C)(C)OC(=O)N1CCOC(CN2CCN(Cc3ccccc3)CC2)C1]

tert-Butyl 2-(hydroxymethyl)morpholine-4-carboxylate (400 mg) and Dess-Martin periodinane (781 mg) are stirred for 2 hours in CH$_2$Cl$_2$ (15 ml). Satd. aqueous NaHCO$_3$ (30 ml) is added and the mixture stirred for 45 min. The layers are separated, dried (Na$_2$SO$_4$), filtered, and the solvent is removed under reduced pressure. Sodium triacetoxyborohydride (829 mg) is added to a mixture of 1-benzylpiperazine (297 µl), tert-butyl 2-formylmorpholine-4-carboxylate (400 mg) and acetic acid (282 µl) in THF (30 ml). The mixture is stirred over night. An aqueous solution of potassium carbonate (15%) is added and the mixture stirred for 30 min. The organic layer is separated and the aqueous layer is extracted with CH$_2$Cl$_2$. The combined organic layers are washed with satd. aqueous NH$_4$Cl (2×), dried (Na$_2$SO$_4$) and filtered, and the solvent is removed under reduced pressure to give tert-butyl 2-((4-benzylpiperazin-1-yl)methyl)morpholine-4-carboxylate (600 mg). m/z(+) 376 (M+H$^+$).

The tert-butyl 2-(hydroxymethyl)morpholine-4-carboxylate used in the above procedure is commercially available and was purchased from ABCR. 1-Benzylpiperazine is commercially available and was purchased from Aldrich.

Examples 1-4, 6-9, 13-14 are prepared in an manner analogous to example 10.

4-benzyl-2-(piperazin-1-ylmethyl)morpholine

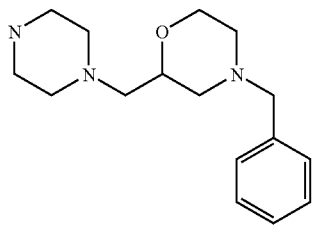 [SMILES: c1ccc(CN2CCOC(CN3CCNCC3)C2)cc1]

To a solution of tert-butyl 4-((4-benzylmorpholin-2-yl)methyl)piperazine-1-carboxylate (165 mg) in CH$_2$Cl$_2$ (5 ml) is added trifluoroacetic acid (1.0 ml), and the mixture is stirred over night. The solvent is removed under reduced pressure. The residue is dissolved in CH$_2$Cl$_2$ and washed with an aqueous solution of potassium carbonate (20%), dried (Na$_2$SO$_4$) and filtered, and the solvent is removed under reduced pressure to give 4-benzyl-2-(piperazin-1-ylmethyl)morpholine (119 mg). m/z(+) 276 (M+H$^+$).

4-Benzyl-2-(piperazin-1-ylmethyl)morpholine is used to synthesize example 7.

tert-butyl 4-((4-benzylmorpholin-2-yl)methyl)piperazine-1-carboxylate

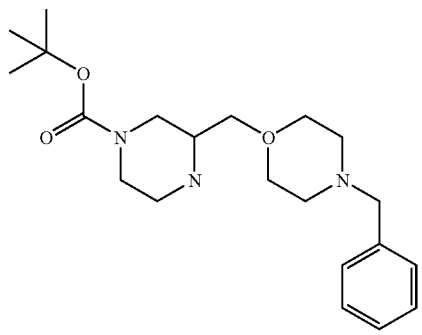

(4-Benzylmorpholin-2-yl)methanol (200 mg) and Dess-Martin periodinane (409 mg) are stirred for 2 hours in CH$_2$Cl$_2$ (15 ml). Satd. aqueous NaHCO$_3$ (50 ml) is added and the mixture stirred for 45 min. The layers are separated, dried (Na$_2$SO$_4$), filtered, and the solvent is removed under reduced pressure. Sodium triacetoxyborohydride (448 mg) is added to a mixture of tert-butyl piperazine-1-carboxylate (150 mg), 4-benzylmorpholine-2-carbaldehyde (220 mg) and acetic acid (111 µl) in THF (10 ml). The mixture is stirred over night. An aqueous solution of potassium carbonate (15%) is added and the mixture stirred for 30 min. The organic layer is separated and the aqueous layer is extracted with CH$_2$Cl$_2$. The combined organic layers are washed with an aqueous solution of potassium carbonate (20%), dried (Na$_2$SO$_4$) and filtered, and the solvent is removed under reduced pressure to give tert-butyl 4-((4-benzylmorpholin-2-yl)methyl)piperazine-1-carboxylate (165 mg).

The (4-benzylmorpholin-2-yl)methanol used in the above procedure is commercially available and was purchased from ABCR, tert-butyl piperazine-1-carboxylate is commercially available and was purchased from Aldrich.

Route A2
Preparation of Example 12:

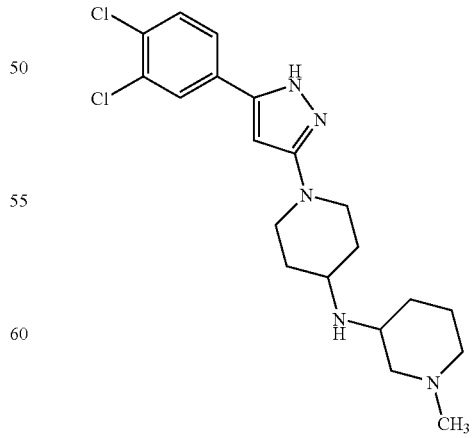

To a solution of 1-(5-(3,4-dichlorophenyl)-1H-pyrazol-3-yl)piperidin-4-one (100 mg) and 1-methylpiperidin-3- amine*2HCl (91 mg) in THF (5 ml) is added HOAc until pH=4-5 is reached. Sodium triacetoxyborohydride (103 mg) is added, and the mixture is stirred over night. The solvent is removed under reduced pressure. The residue is dissolved in CH$_2$Cl$_2$, and the organic layer is washed with aqueous citric acid (20%), satd. aqueous NaHCO$_3$, water, and then dried (Na$_2$SO$_4$) and filtered, and the solvent is removed under reduced pressure. The crude product is purified using reverse phase HPLC (Varian C18 Microsorb) eluting with a gradient of 10-100% acetonitrile in water containing 0.2% trifluoroacetic acid to give 12 (17 mg). m/z(+) 408/410/412 (M+H$^+$).

The 1-methylpiperidin-3-amine*2HCl used in the above procedure is commercially available and was purchased from Chess. The 2-(pyrrolidin-1-yl)ethanamine used to synthesize 11 and 3-methylcyclohexanamine used to synthesize 5 are commercially available and were purchased from Aldrich.

1-(5-(3,4-dichlorophenyl)-1H-pyrazol-3-yl)piperidin-4-one

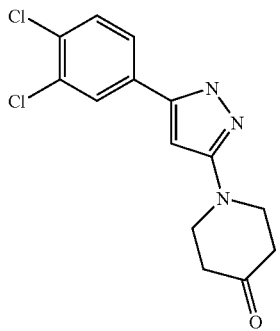 [SMILES: O=C1CCN(c2cc(-c3ccc(Cl)c(Cl)c3)[nH]n2)CC1]

To a solution of 8-(5-(3,4-dichlorophenyl)-1H-pyrazol-3-yl)-1,4-dioxa-8-azaspiro[4.5]decane (500 mg) in 1,4-dioxane (5 ml) is added conc. HCl (4 ml), and the mixture is stirred for 2 hours at 50° C. The solvent is removed under reduced pressure. The residue is dissolved in CH$_2$Cl$_2$ and washed with satd. aqueous NaHCO$_3$ (2×), dried (Na$_2$SO$_4$) and filtered, and the solvent is removed under reduced pressure to give 1-(5-(3,4-dichlorophenyl)-1H-pyrazol-3-yl)piperidin-4-one (400 mg). m/z(+) 310/312/314 (M+H$^+$).

8-(5-(3,4-dichlorophenyl)-1H-pyrazol-3-yl)-1,4-dioxa-8-azaspiro[4.5]decane

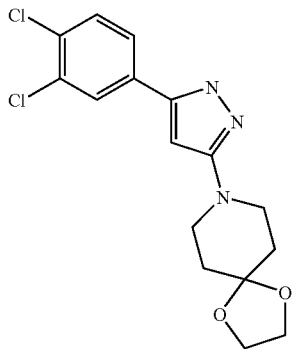 [SMILES: Clc1ccc(-c2cc(N3CCC4(CC3)OCCO4)n[nH]2)cc1Cl]

1,4-dioxa-8-azaspiro[4.5]decane (2.2 ml) is added to a solution of 1-(3,4-dichlorophenyl)-3,3-bis(methylthio)prop-2-en-1-one (2.0 g) in ethanol (70 ml) and heated to 80° C. over night. Hydrazine-hydrate (1 ml) is added to the reaction mixture and the mixture is stirred over night at 80° C. The solvent is removed under reduced pressure. The crude product is purified using reverse phase HPLC (Varian C18 Microsorb) eluting with a gradient of 10-100% acetonitrile in water containing 0.2% trifluoroacetic acid to give 8-(5-(3,4-dichlorophenyl)-1H-pyrazol-3-yl)-1,4-dioxa-8-azaspiro[4.5]decane (550 mg). m/z(+) 354/356/358 (M+H$^+$).

The 1,4-dioxa-8-azaspiro[4.5]decane used in the above procedure is commercially available and was purchased from Acros.

Pyridazines

General Methods:

Part of the amines used in Route B are synthesized according to route A.

Route B1

Preparation of Example 19

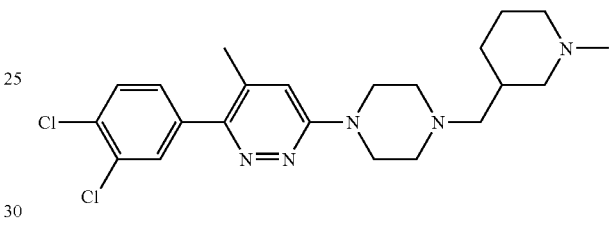

NEt$_3$ (46 µl) is added to a solution of 3-chloro-6-(3,4-dichlorophenyl)-5-methylpyridazine (60 mg) and 1-((1-methylpiperidin-3-yl)methyl)piperazine (60 mg) in CH$_3$CN (1 ml). The reaction mixture is heated for 45 min at 180° C. in the microwave. The crude product is purified using reverse phase HPLC (Chromolith C18) eluting with a gradient of 10-90% acetonitrile in water containing 0.1% formic acid to give compound 19 (82 mg). m/z(+) 434/436/438 (M+H$^+$).

The 1-((1-methylpiperidin-3-yl)methyl)piperazine used in the above procedure is commercially available and was purchased from Chess.

The 4-isopropyl-2-(piperazin-1-ylmethyl)morpholine used to synthesize 16, 21 is prepared according to synthetic route A1. The N,N-dimethyl-1-(piperidin-3-yl)methanamine used to synthesize 28 is commercially available and was purchased from Matrix. The 1-(2-(pyrrolidin-1-yl)ethyl)piperazine used to synthesize 25, 1-(3-(piperidin-1-yl)propyl)piperazine used to synthesize 27, N,N-dimethyl-2-(piperazin-1-yl)ethanamine used to synthesize 30 and N,N-dimethyl-3-(piperazin-1-yl)propan-1-amine used to synthesize 31 are commercially available and were purchased from Emkachem. The 4-(2-(piperazin-1-yl)ethyl)morpholine used to synthesize 26 is commercially available and was purchased from Acros. The N',N',N"-trimethyl-N"-(piperidin-4-yl)ethane-1,2-diamine used to synthesize 33 was purchased from Chembridge. The 1-(2-(piperidin-1-yl)ethyl)piperazine used to synthesize 47 was purchased from Emka. The 1-methylpiperidin-4-amine used to synthesize 53 is commercially available and was purchased from ABCR. The N,N-dimethylcyclohexane-1,4-diamine used to synthesize 54 is commercially available and was purchased from AB Chem.

3-chloro-6-(3,4-dichlorophenyl)-5-methylpyridazine

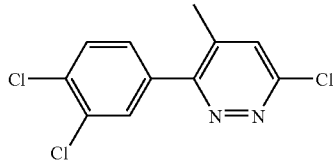

6-(3,4-dichlorophenyl)-5-methylpyridazin-3(2H)-one (500 mg) is added stepwise to phosphoryl trichloride (1.8 ml). The reaction mixture is heated to 100° C. for 1 hour, then cooled to room temperature and poured onto ice water. The formed precipitate is separated, washed with water and dried to give 3-chloro-6-(3,4-dichlorophenyl)-5-methylpyridazine (509 mg).

6-(3,4-dichlorophenyl)-5-methylpyridazin-3(2H)-one

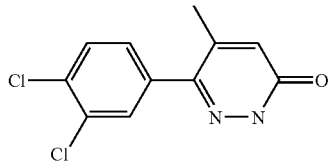 [SMILES: Cc1cc(=O)[nH]nc1-c1ccc(Cl)c(Cl)c1]

A mixture of 1-(3,4-dichlorophenyl)propan-1-one (1.0 g), glyoxylic acid monohydrate (453 mg) and acetic acid (1.5 ml) is heated to 95° C. over night, and then cooled to room temperature. Water (12 ml) and conc. $NH_3$ (7.5 ml) is added to the reaction mixture until pH=10 is reached. The mixture is washed with $CH_2Cl_2$ (3×). Hydrazine-hydrate (244 µl) is added to the aqueous layer and the mixture heated under reflux over night. The mixture is cooled to room temperature. The precipitate is separated, washed with water and dried to give 6-(3,4-dichlorophenyl)-5-methylpyridazin-3(2H)-one (510 mg). m/z(+) 255/257/259 (M+H+). 1-(3,4-dichlorophenyl)propan-1-one used in the above procedure is commercially available and was purchased from Aldrich.

6-(3,4-dichlorophenyl)pyridazin-3(2H)-one is synthesized using the same reaction conditions starting from 1-(3,4-dichlorophenyl)ethanone.

The 1-(3,4-dichlorophenyl)ethanone used to synthesize 16-17, 23-28, 30-48, 50-54 and 1-(3-(trifluoromethyl)phenyl)ethanone used to synthesize 22 are commercially available and were purchased from Aldrich. The 1-(3,5-dichlorophenyl)ethanone used to synthesize 20, 29 and 1-(3-fluoro-5-(trifluoromethyl)phenyl)ethanone used to synthesize 49 were purchased from ABCR. The 1-(3,5-bis(trifluoromethyl)phenyl)ethanone used to synthesize 18 was purchased from Lancaster.

N-(3-morpholinopropyl)piperidine-4-carboxamide

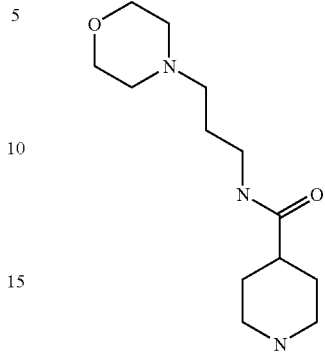

Trifluoroacetic acid (4.4 ml) is added to a solution of tert-butyl 4-(3-morpholinopropylcarbamoyl)piperidine-1-carboxylate (2.3 g) in $CH_2Cl_2$ (30 ml), and the mixture is stirred over night. The solvent is removed under reduced pressure to give crude N-(3-morpholinopropyl)piperidine-4-carboxamide (1.55 g).

The crude product is used without purification in the next step to give 23.

tert-butyl 4-(3-morpholinopropylcarbamoyl)piperidine-1-carboxylate

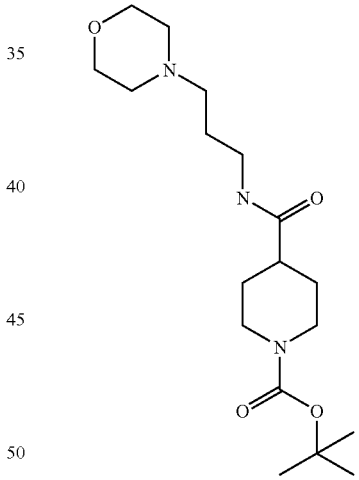

$NEt_3$ (1.8 ml) is added to a solution of 1-(tert-butoxycarbonyl)piperidine-4-carboxylic acid (1.5 g) in DMF (40 ml) and the mixture is stirred for 10 min. TBTU (3.15 g) is added, and after additional 10 min the 3-morpholinopropan-1-amine (0.98 ml) is added. The reaction mixture is stirred over night and the solvent is removed under reduced pressure. The residue is dissolved in EtOAc and washed with satd. aqueous $NaHCO_3$, aqueous citric acid (10%) and brine, dried ($MgSO_4$) and filtered, and the solvent is removed under reduced pressure to give crude tert-butyl 4-(3-morpholinopropylcarbamoyl)piperidine-1-carboxylate (2.3 g). The crude product is used without purification in the next step.

The 1-(tert-butoxycarbonyl)piperidine-4-carboxylic acid used in the above procedure is commercially available and was purchased from Fluka. The 3-morpholinopropan-1- amine used in the above procedure is commercially available and was purchased from Aldrich.

N,N-dimethyl-2-(4-(piperazin-1-yl)cyclohexyl)ethanamine

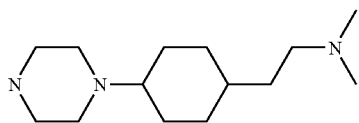 [SMILES: CN(C)CCC1CCC(N2CCNCC2)CC1]

2-(4-(4-benzylpiperazin-1-yl)cyclohexyl)-N,N-dimethylethanamine (660 mg) is dissolved in ethanol (20 ml). Palladium on carbon (100 mg) is added and the mixture is stirred for 16 hours at 50° C. under an atmosphere of hydrogen (50 psi). The catalyst is removed by filtration and the filtrate concentrated under reduced pressure to give N,N-dimethyl-2-(4-(piperazin-1-yl)cyclohexyl)ethanamine (412 mg). m/z (+) 240 (M+H$^+$).

2-(4-(4-benzylpiperazin-1-yl)cyclohexyl)-N,N-dimethylethanamine

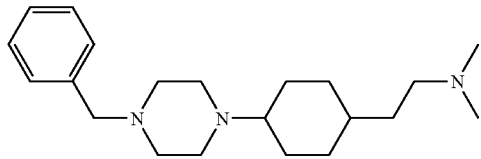 [SMILES: CN(C)CCC1CCC(N2CCN(Cc3ccccc3)CC2)CC1]

2-(4-(4-benzylpiperazin-1-yl)cyclohexyl)-N,N-dimethylacetamide (800 mg) is dissolved in THF (20 ml) and cooled to 0° C. 2 M LiAlH$_4$ in THF (2.3 ml) is added. The reaction mixture is warmed to room temperature and stirred for 1 hour. The reaction is quenched by slow addition of satd. aqueous K$_2$CO$_3$ (50 ml), then a potassium sodium tartrate solution (20 ml) is added. The mixture is diluted with EtOAc and the layers are separated. The aqueous layer is extracted with EtOAc (2×). The combined organic layers are dried (Na$_2$SO$_4$), filtered, and the solvent is removed under reduced pressure to give 2-(4-(4-benzylpiperazin-1-yl)cyclohexyl)-N,N-dimethylethanamine (660 mg). m/z(+) 330 (M+H$^+$).

2-(4-(4-benzylpiperazin-1-yl)cyclohexyl)-N,N-dimethylacetamide

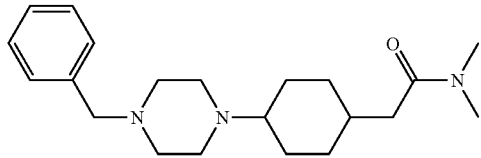 [SMILES: CN(C)C(=O)CC1CCC(N2CCN(Cc3ccccc3)CC2)CC1]

Sodium triacetoxyborohydride (1.5 g) is added to a mixture of 1-benzylpiperazine (714 µl), N,N-dimethyl-2-(4-oxocyclohexyl)acetamide (820 mg) and acetic acid (680 µl) in THF (50 ml). The mixture is stirred over night. An aqueous solution of potassium carbonate (20%) is added and the mixture stirred for 30 min. The organic layer is separated and the aqueous layer is extracted with EtOAc. The combined organic layers are washed with satd. aqueous NH$_4$Cl (2×), dried (Na$_2$SO$_4$) and filtered, and the solvent is removed under reduced pressure. The crude product is purified using reverse phase HPLC (Varian C18 Microsorb) eluting with a gradient of 10-100% acetonitrile in water containing 0.2% trifluoroacetic acid to give 2-(4-(4-benzylpiperazin-1-yl)cyclohexyl)-N,N-dimethylacetamide (800 mg). m/z(+) 344 (M+H$^+$). The 2-(pyrrolidin-1-yl)ethanamine and the tert-butyl 4-oxopiperidine-1-carboxylate used to synthesize 34 were purchased from Aldrich. The tert-butyl 3-oxocyclohexylcarbamate used to synthesize 50 was purchased from AB Chem. The 1-benzyl-1,4-diazepane used to synthesize 52 was purchased from Lancaster.

N,N-dimethyl-2-(4-oxocyclohexyl)acetamide

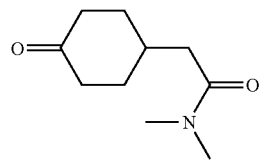

p-Toluenesulfonic acid (84 mg) is added to a solution of N,N-dimethyl-2-(1,4-dioxaspiro[4.5]decan-8-yl)acetamide (500 mg) in acetone (10 ml) and the mixture is heated under reflux for 3 hours. The solvent is removed under reduced pressure. The residue is dissolved in CH$_2$Cl$_2$ and washed with water. The organic layer is dried (Na$_2$SO$_4$) and filtered, and the solvent is removed under reduced pressure to give N,N-dimethyl-2-(4-oxocyclohexyl)acetamide (400 mg).

N,N-dimethyl-2-(1,4-dioxaspiro[4.5]decan-8-yl)acetamide

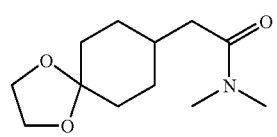 [SMILES: CN(C)C(=O)CC1CCC2(CC1)OCCO2]

NEt$_3$ (2.0 ml) and TBTU (2.56 g) are added to a solution of 2-(1,4-dioxaspiro[4.5]decan-8-yl)acetic acid (1.45 g; see J. Med. Chem. 1998, 41(5), 760) in DMF (50 ml) and the mixture is stirred for 30 min. 2 M Dimethylamine in THF (7.24 ml) is added. The reaction mixture is stirred for one hour and the solvent is removed under reduced pressure. The residue is dissolved in EtOAc and washed with water and aqueous citric acid (10%, 2×). The organic layer is dried (Na$_2$SO$_4$) and filtered, and the solvent is removed under reduced pressure. The crude product is purified using reverse phase HPLC (Varian C18 Microsorb) eluting with a gradient of 10-100% acetonitrile in water containing 0.2% trifluoroacetic acid to give N,N-dimethyl-2-(1,4-dioxaspiro[4.5]decan-8-yl)acetamide (400 mg) and N,N-dimethyl-2-(4-oxocyclohexyl)acetamide (420 mg).

4-(4-benzylpiperazin-1-yl)cyclohexanecarboxylic acid

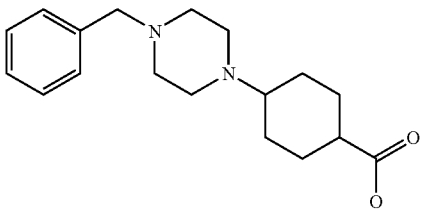 [SMILES: O=C(O)C1CCC(N2CCN(Cc3ccccc3)CC2)CC1]

1 M NaOH (23 ml) is added to a solution of ethyl 4-(4-benzylpiperazin-1-yl)cyclohexanecarboxylate (2.56 g) in Methanol (30 ml). The mixture is stirred for 2 days and the solvent is removed under reduced pressure. The crude product is purified using reverse phase HPLC (Varian C18 Microsorb) eluting with a gradient of 10-100% acetonitrile in water containing 0.2% trifluoroacetic acid to give 4-(4-benzylpiperazin-1-yl)cyclohexanecarboxylic acid: (2.33 g). m/z (+) 303 (M+H$^+$).

The ethyl 4-oxocyclohexanecarboxylate used to synthesize 51 was purchased from Aldrich.

tert-butyl 4-(3-(diethylamino)propyl)piperazine-1-carboxylate

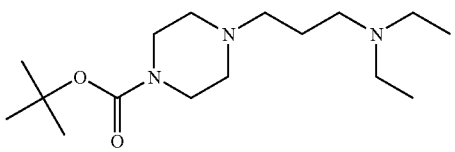 [SMILES: CCN(CC)CCCN1CCN(C(=O)OC(C)(C)C)CC1]

3-Chloro-N,N-diethylpropan-1-amine (1.6 g) is added to a mixture of tert-butyl piperazine-1-carboxylate (2.0 g) and NEt$_3$ (1.5 ml) in methanol (30 ml). The mixture is stirred for 6 hours at 70° C. and cooled to room temperature. The solvent is removed under reduced pressure. Satd. aqueous NaHCO$_3$ is added to the crude product and the aqueous layer is extracted with EtOAc (3×). The combined organic layers are dried (Na$_2$SO$_4$) and filtered, and the solvent is removed under reduced pressure to give tert-butyl 4-(3-(diethylamino)propyl)piperazine-1-carboxylate (2.48 g). m/z(+) 300 (M+H$^+$).

The 3-chloro-N,N-diethylpropan-1-amine used in the above procedure is commercially available and was purchased from Narchem.

Route B2
Preparation of Example 32:

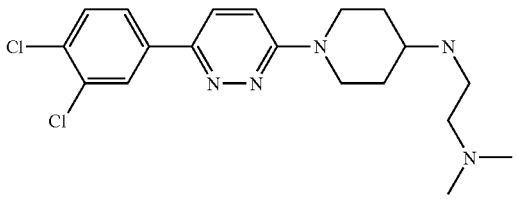 [SMILES: CN(C)CCNC1CCN(c2ccc(-c3ccc(Cl)c(Cl)c3)nn2)CC1]

A solution of N,N-dimethylethane-1,2-diamine (10.9 mg) in MeOH/HOAc (100 µl, 10/1) is added to a mixture of 1-(6-(3,4-dichlorophenyl)pyridazin-3-yl)piperidin-4-one (20 mg) in MeOH/HOAc (100 µl, 10/1) and THF (200 µl), and the mixture is stirred for 15 min. 2-Picoline borane complex (6.6 mg) in MeOH/HOAc (100 µl, 10/1) is added and the mixture is stirred over night. A mixture of DMF and water (400 µl, 1/1) is added. The mixture is stirred for 1 hour and then acidified with TFA (50%). The crude product is purified using reverse phase HPLC (Waters, Sunfire RP18) eluting with a gradient of 10-90% acetonitrile in water containing 0.1% trifluoroacetic acid to give compound 32 (22 mg). m/z (+) 394/396/398 (M+H$^+$).

The 2-(piperidin-1-yl)ethanamine used to synthesize 35 and the 1-benzylpyrrolidin-3-amine used to synthesize 40 were purchased from Aldrich. The 2-(azepan-1-yl)ethanamine used to synthesize 36 was purchased from Chemcollect. The tert-butyl pyrrolidin-3-ylcarbamate used to synthesize 37 was purchased from TCI. The (S)- and (R)-tert-butyl pyrrolidin-3-ylcarbamate used to synthesize 38 and 39 and the tert-butyl 3-aminopiperidine-1-carboxylate used to synthesize 41 were purchased from ABCR. The 1-ethylpiperidin-3-amine used to synthesize 43 was purchased from Matrix. The 1-propylpiperidin-3-amine used to synthesize 44 and the (1-methylpiperidin-4-yl)methanamine used to synthesize 46 were purchased from Chembridge.

1-(6-(3,4-dichlorophenyl)pyridazin-3-yl)piperidin-4-one

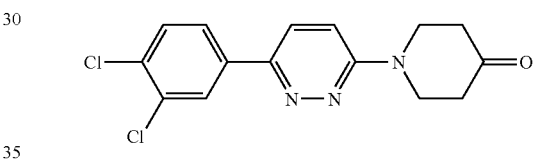

M HCl (10 ml) is added to a mixture of 8-(6-(3,4-dichlorophenyl)pyridazin-3-yl)-1,4-dioxa-8-azaspiro[4.5]decane (500 mg) in water (5 ml). The mixture is stirred for 1 hour at 60° C., cooled to room temperature, diluted with water and neutralized with 4 N NaOH. The aqueous layer is extracted with EtOAc (3×). The combined organic layers are washed with brine, dried (Na$_2$SO$_4$) and filtered, and the solvent is removed under reduced pressure to give 1-(6-(3,4-dichlorophenyl)pyridazin-3-yl)piperidin-4-one (370 mg). m/z(+) 322/324/326 (M+H$^+$).

8-(6-(3,4-dichlorophenyl)pyridazin-3-yl)-1,4-dioxa-8-azaspiro[4.5]decane

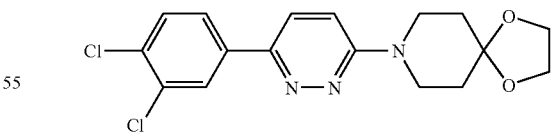

A mixture of 3-chloro-6-(3,4-dichlorophenyl)pyridazine (500 mg, see route B1 for preparation) and 1,4-dioxa-8-azaspiro[4.5]decane (2.47 ml) is heated for 30 min at 100° C. in the microwave. Water (75 ml) is added. The precipitate is separated, washed with water and dried (500 mg). m/z(+) 366/368/370 (M+H$^+$).

The 1,4-dioxa-8-azaspiro[4.5]decane used in the above procedure is commercially available and was purchased from Janssen.

ABBREVIATIONS

Ac acetyl
Bu butyl
Conc. concentrated
DMF N,N-dimethylformamide
ESI electrospray ionization
Et ethyl
Me methyl
Min minute
MS mass spectrometry
m/z mass-to-charge ratio
Satd. saturated
t tertiary
TBTU 0-(Benzotriazol-1-yl)-1,1,3,3-tetramethyluronium tetrafluoroborate
TFA trifluoroacetic acid
THF tetrahydrofuran

The invention claimed is:

1. A compound of general formula (I),

A-L-D-L'-E-G  (I)

wherein
A is a group selected from
$C_{1-4}$alkyl or
piperidinyl, optionally substituted by one or more —$C_1$-$C_4$-alkyl, or -cyclopropyl or
morpholinyl, optionally substituted by one or more —$C_{1-4}$-alkyl, -cyclohexyl,or -benzyl; or
pyrrolidinyl, optionally substituted by one or more —$C_1$-$C_4$-alkyl,-cyclopentyl,or -benzyl; or
piperazinyl, optionally substituted by one or more —$C_{1-4}$-alkyl; or
azepanyl, optionally substituted by one or more —$C_{1-4}$-alkyl,
L is a linker selected from
a single bond, or
M, with M being —$C_{1-8}$-alkylene-, optionally being substituted by one or more =O groups,
D is

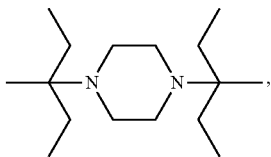

L' is
a single bond,
E is

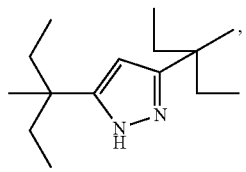 [SMILES: CCC(C)(CC)c1cc(C(C)(CC)CC)[nH]n1]

G is a
group selected from 4-bromo-phenyl, 3-chloro-phenyl, 4-chloro-phenyl, 3,4-dichloro-phenyl, 3,5-dichloro-phenyl, 2,3-dichloro-phenyl, 2,4-dichloro-phenyl, 2,5-dichloro-phenyl, 3,5-di-trifluoromethyl-phenyl, 3-trifluoromethyl-phenyl, 3-fluoro-5-trifluoromethyl-phenyl, 3-chloro-5-trifluoromethyl-phenyl, 3-chloro-4-trifluoromethyl-phenyl, 3-isopropyl-phenyl, 4-isopropyl-phenyl, 3,5-dimethoxy-phenyl, 3-chloro-4-methoxy-phenyl and 2-methyl-4-chloro-phenyl,
optionally in form of their individual optical isomers, mixtures of their individual optical isomers, or racemates, as well as in form of their acid addition salts with pharmacologically acceptable acids.

2. The compound according to claim 1, wherein
L is a linker selected from
a single bond, or $C_{1-3}$-alkylene-, optionally being substituted by one =O group,
optionally in form of their individual optical isomers, mixtures of their individual optical isomers, or racemates, as well as in form of their acid addition salts with pharmacologically acceptable acids.

3. The compound according to claim 1, wherein
A is a group selected from
methyl, piperidin-1-yl, piperidin-3-yl, 1-methyl-piperidin-2-yl, 1-methyl-piperidin-3-yl, 1-ethyl-piperidin-3-yl, 1-propyl-piperidin-3-yl, 1-i-propyl-piperidin-3-yl, 1-cyclopropyl-piperidin-3-yl, 1-methyl-piperidin-4-yl, morpholin-4-yl, 4-i-propyl-morpholin-2-yl, 4-cyclohexyl-morpholin-2-yl, 4-benzyl-morpholin-2-yl, 4-methyl-morpholin-2-yl, 4-methyl-morpholin-3-yl, pyrrolidin-1-yl, pyrrolidin-3-yl, 1-methyl-pyrrolidin-2-yl, 1-methyl-pyrrolidin-3-yl, 1-cyclopentyl-pyrrolidin-3-yl, 1-benzyl-pyrrolidin-3-yl, 1-methyl-piperazin-4-yl, 1-i-propyl-piperazin-3-yl, 1-i-propyl-4-methyl-piperazin-3-yl, azepan-1-yl, azepan-3-yl, 1-methyl-azepan-3-yl,
L is a linker selected from
a single bond and —$CH_2$—,
optionally in form of their individual optical isomers, mixtures of their individual optical isomers, or racemates, as well as in form of their acid addition salts with pharmacologically acceptable acids.

4. A compound selected from the group consisting of

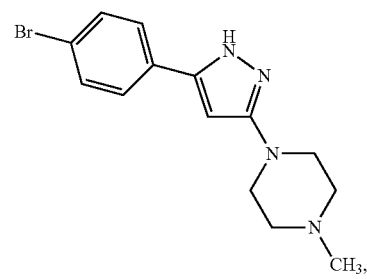

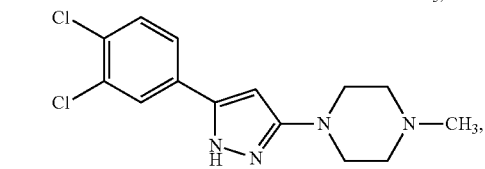

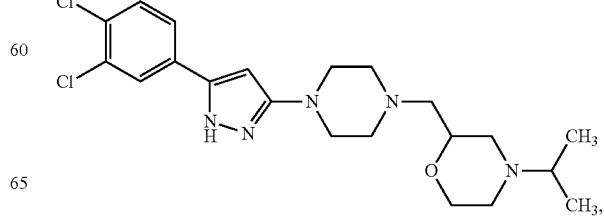

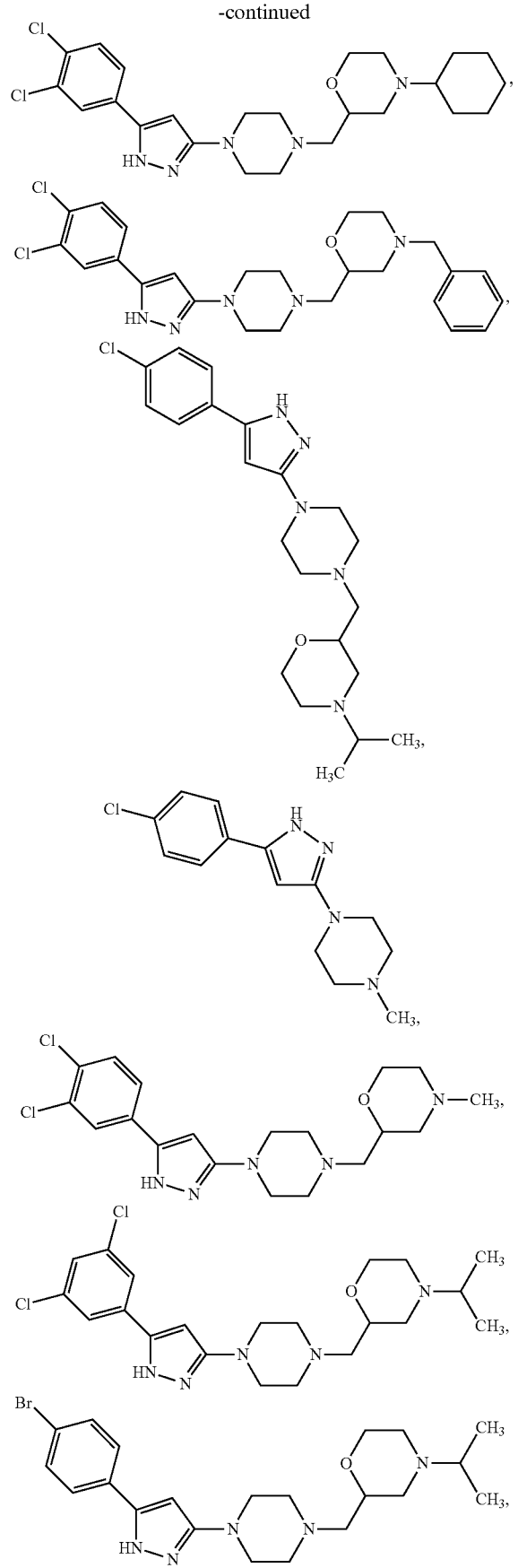
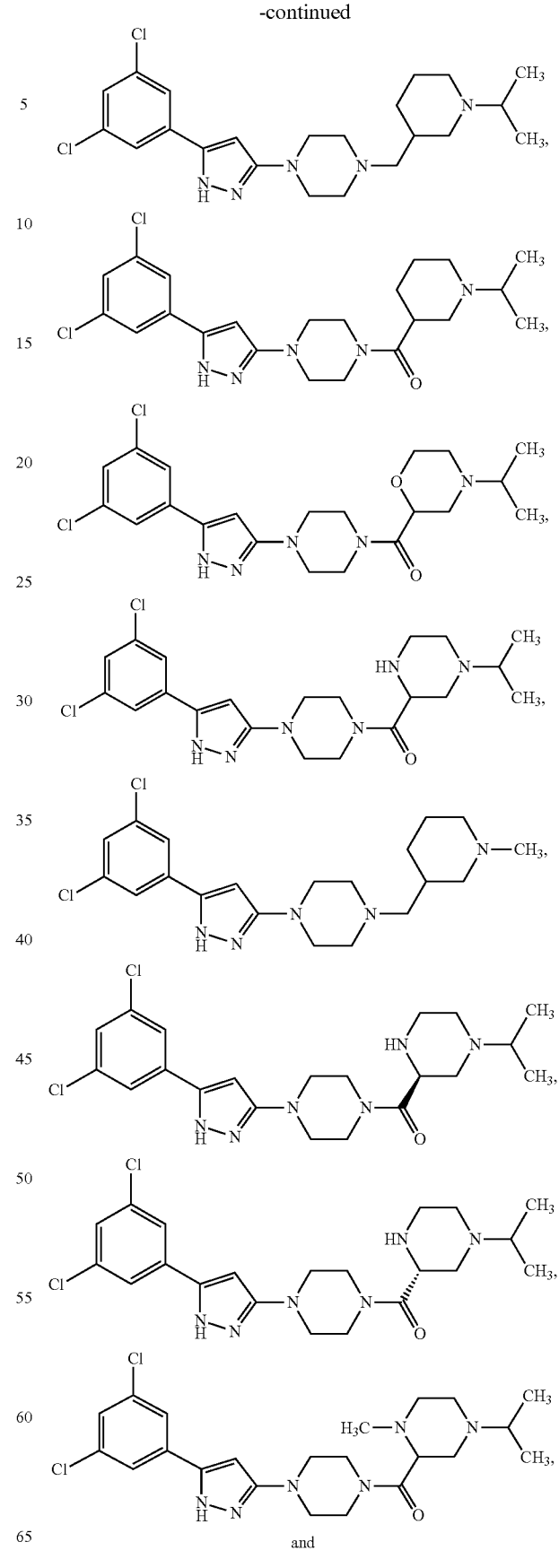

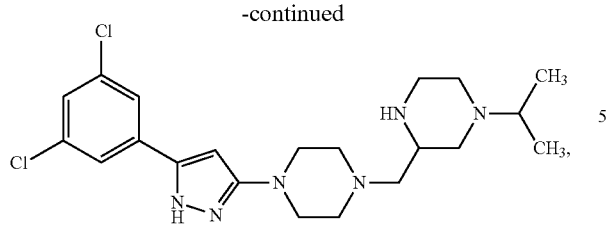
and their acid addition salts with pharmacologically acceptable acids.
* * * * *